United States Patent
Sikora et al.

(10) Patent No.: US 10,418,128 B2
(45) Date of Patent: Sep. 17, 2019

(54) SYSTEMS AND METHODS FOR ERROR CORRECTION IN DNA SEQUENCING

(71) Applicant: LIFE TECHNOLOGIES CORPORATION, Carlsbad, CA (US)

(72) Inventors: Marcin Sikora, Burlingame, CA (US); Alan Blanchard, Middleton, MA (US)

(73) Assignee: Life Technologies Corporation, Carlsbad, CA (US)

(*) Notice: Subject to any disclaimer, the term of this patent is extended or adjusted under 35 U.S.C. 154(b) by 757 days.

(21) Appl. No.: 14/951,964

(22) Filed: Nov. 25, 2015

(65) Prior Publication Data

US 2016/0188794 A1 Jun. 30, 2016

Related U.S. Application Data

(62) Division of application No. 12/910,751, filed on Oct. 22, 2010, now Pat. No. 9,234,239.

(60) Provisional application No. 61/254,545, filed on Oct. 23, 2009.

(51) Int. Cl.
| | |
|---|---|
| *G06F 19/20* | (2011.01) |
| *G16B 25/00* | (2019.01) |
| *G16B 30/00* | (2019.01) |
| *G16B 99/00* | (2019.01) |

(Continued)

(52) U.S. Cl.
CPC .......... *G16B 25/00* (2019.02); *C12Q 1/6869* (2013.01); *C12Q 1/6874* (2013.01); *G16B 30/00* (2019.02); *G16B 99/00* (2019.02)

(58) Field of Classification Search
CPC .......... C12Q 1/6874; C12Q 2521/501; C12Q 2565/102; C12Q 1/6869; G06F 19/10; G06F 19/20; G06F 19/22; G06F 17/30206; G06F 17/30949; G06F 16/1834; G06F 16/9014; H03M 13/1515; H03M 13/2918; H03M 13/2921; H03M 13/616; H03M 13/09; H03M 13/6569; H03M 13/6306;

(Continued)

(56) References Cited

U.S. PATENT DOCUMENTS

| | | |
|---|---|---|
| 2009/0062129 A1 | 3/2009 | McKernan et al. |
| 2011/0202280 A1 | 8/2011 | Sikora et al. |

FOREIGN PATENT DOCUMENTS

| | | | | |
|---|---|---|---|---|
| WO | 2000/040758 | 7/2000 | | |
| WO | 2005/040425 | 5/2005 | | |
| WO | WO200608132 | * | 1/2006 | ............ G06F 19/00 |

(Continued)

OTHER PUBLICATIONS

Anderson et al., "Sequential coding algorithms: a survey and cost analysis," *IEEE Transactions on Information Theory*, vol. 32, Issue 2, Feb. 1984, pp. 169-176.

(Continued)

*Primary Examiner* — Mary K Zeman

(57) ABSTRACT

Disclosed are systems and methods for polynucleotide sequencing where detection and correction of base calling errors can be achieved without reliance on a reference sequence. In certain embodiments, redundant information can be introduced during measurement so as to allow such detection of errors. Such redundant information and measurements can be facilitated by encoding of nucleotide sequence being measured. Various examples of such encoding, redundancy introduction, and decoding are provided.

13 Claims, 39 Drawing Sheets

Specification includes a Sequence Listing.

(51) Int. Cl.
*C12Q 1/6874* (2018.01)
*C12Q 1/6869* (2018.01)

(58) Field of Classification Search
CPC .. H03M 13/6561; H04L 1/0057; H04L 7/048; G16B 25/00; G16B 30/00; G16B 99/00
See application file for complete search history.

(56) References Cited

FOREIGN PATENT DOCUMENTS

| WO | 2006/084132 | 8/2006 |
|---|---|---|
| WO | 2009/046149 | 4/2009 |
| WO | 2009/076238 | 6/2009 |
| WO | 2009/097368 | 8/2009 |
| WO | 2011/050340 | 4/2011 |

OTHER PUBLICATIONS

Astier et al., "Toward Single Molecule DNA Sequencing: Direct Identification of Ribonucleoside and Deoxyribonucleoside 5'-Monophosphates by Using an Engineered Protein Nanopore Equipped with a Molecular Adapter," *J. Am. Chem. Soc.*, vol. 128, No. 5, 2006, pp. 1705-1710.
Bahl et al., "Optimal decoding of linear codes for minimizing symbol error rate," *IEEE Transactions on Information Theory*, Mar. 1974, pp. 284-287.
Clarke et al., "Continuous base identification for single-molecule nanopore DNA sequencing," *Nature Nanotechnology*, vol. 4, Apr. 2009, pp. 265-270.
Hagenauer et al., "A Viterbi algorithm with soft-decision outputs and its applications,"*Proceedings IEEE Global Telecommunications Conference and Exhibition 'Communications Technology for the 1990s and Beyond' (GLOBECOM)*, vol. 3, Nov. 1989, pp. 1680-1686.
Homer et al., "Local alignment of generalized k-base encoded DNA sequence," *BMC Bioinformatics*, vol. 11, No. 347, 2010, pp. 1-10.
Howorka et al., "Sequence-specific detection of individual DNA strands using engineered nanopores," *Nature Biotechnology*, vol. 19, 2001, pp. 636-639.
Kahng et al., "Evaluation of placement techniques for DNA probe array layout " *International Conference on Computer Aided Design*, San Jose, CA, Nov. 9-13, 2003, pp. 262-269.
Lieberman et al., "Processive Replication of Single DNA Molecules in a Nanopore Catalyzed by phi29 DNA Polymerase," *J. Am. Chem. Soc.* vol. 132, No. 50, 2010, pp. 17961-17972.
Mackay, "Information Theory, Inference, and Learning Algorithms," *Cambridge University Press*, Version 7.2, Mar. 28, 2005, pp. v-177.
May et al., "An error-correcting code framework for genetic sequence anlaysis," *Journal of the Franklin Institute*, vol. 341, 2004, pp. 89-109.
McKernan et al., "Sequence and structural variation in a human genome uncovered by short-read, massively parallel ligation sequencing using two-base encoding", *Genome Res*, vol. 19, No. 9, 2009, pp. 1527-1541.
Olasagasti et al., "Replication of individual DNA molecules under electronic control using a protein nanopore," *Nature Nanotechnology*, vol. 5, Nov. 2010, pp. 798-806.
PCT/US2010/053873, International Preliminary Report on Patentability dated Apr. 24, 2012, pp. 1-11.
PCT/US2010/053873, International Search Report dated Apr. 6, 2011, 6 pages.
Stoddart et al., "Multiple Base-Recognition Sites in a Biological Nanopore: Two Heads are Better than One," *Angewandte Chemie International Edition*, vol. 49, Issue 3, Jan. 12, 2010, pp. 556-559.
Stoddart et al., "Nucleobase recognition in ssDNA at the central constriction of the αhemolysin pore," *Nano Lett.*, vol. 10, No. 9, doi:10.1021/nl101955a, Sep. 8, 2010, pp. 3633-3637.
Stoddart et al., "Single-nucleotide discrimination in immobilized DNA oligonucleotides with a biological nanopore", *PNAS*, vol. 106, No. 19, May 12, 2009, pp. 7702-7707.
Viterbi, "Error bounds for convolutional codes and an asymptotically optimum decoding algorithm," *IEEE Transactions on Information Theory*, vol. 13, Issue 2, Apr. 1967, pp. 260-269.
Wallace et al., "Identification of epigenetic DNA modifications with a protein nanopore," *Chem. Commun.*, vol. 46, 2010, pp. 8195-8197.

\* cited by examiner

1. Prime and Ligate

2. Image

3. Cap Unextended Strands

4. Cleave off Fluor

5. Repeat steps 1-4 to Extend Sequence

6. Primer Reset

7. Repeat steps 1-5 with new primer

FIG. 20A

| Base 2 | | A | C | G | T |
|---|---|---|---|---|---|
| Base 1 | A | 0 | 1 | 2 | 3 |
| | C | 1 | 0 | 3 | 2 |
| | G | 2 | 3 | 0 | 1 |
| | T | 3 | 2 | 1 | 0 |

G = (1 1)
Color = Base1 + Base2

FIG. 20B

| Base 2 | | A | C | G | T |
|---|---|---|---|---|---|
| Base 1 | A | 0 | 1 | 2 | 3 |
| | C | 2 | 3 | 0 | 1 |
| | G | 3 | 2 | 1 | 0 |
| | T | 1 | 0 | 3 | 2 |

G = (1 2)
Color = Base1 + 2 × Base2

FIG. 20C

| Base 2 | | A | C | G | T |
|---|---|---|---|---|---|
| Base 1 | A | 0 | 1 | 2 | 3 |
| | C | 3 | 2 | 1 | 0 |
| | G | 1 | 0 | 3 | 2 |
| | T | 2 | 3 | 0 | 1 |

G = (1 3)
Color = Base1 + 3 × Base2

Lookup tables

| A | 0 |
| C | 1 |
| G | 2 |
| T | 3 |

| ○ | 0 |
| ○ | 1 |
| ○ | 2 |
| ◐ | 3 |

GF(4) Multiplication

| × | 0 | 1 | 2 | 3 |
|---|---|---|---|---|
| 0 | 0 | 0 | 0 | 0 |
| 1 | 0 | 1 | 2 | 3 |
| 2 | 0 | 2 | 3 | 1 |
| 3 | 0 | 3 | 1 | 2 |

GF(4) Addition

| + | 0 | 1 | 2 | 3 |
|---|---|---|---|---|
| 0 | 0 | 1 | 2 | 3 |
| 1 | 1 | 0 | 3 | 2 |
| 2 | 2 | 3 | 0 | 1 |
| 3 | 3 | 2 | 1 | 0 |

FIG. 21

Calculate
$P(B_i = A \mid \text{Measurements})$
$P(B_i = C \mid \text{Measurements})$
$P(B_i = G \mid \text{Measurements})$ for every base position $B_i$
$P(B_i = T \mid \text{Measurements})$ (T) $\alpha_0(T) = 1$
FIG. 35A
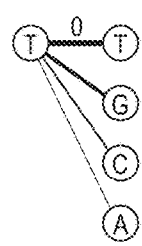 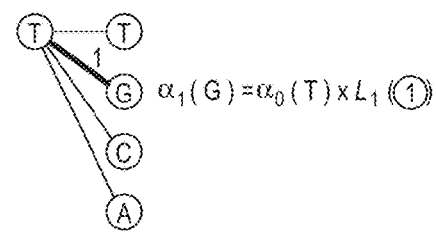
$\alpha_1(T) = \alpha_0(T) \times L_1(\text{\textcircled{0}})$
FIG. 35B
$\alpha_1(G) = \alpha_0(T) \times L_1(\text{\textcircled{1}})$
FIG. 35C
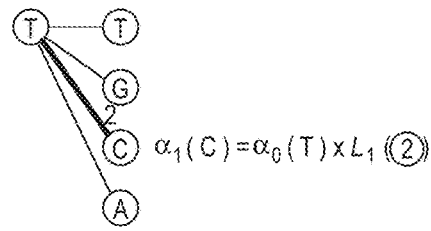 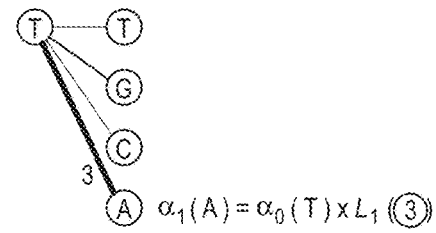
$\alpha_1(C) = \alpha_0(T) \times L_1(\text{\textcircled{2}})$
FIG. 35D
$\alpha_1(A) = \alpha_0(T) \times L_1(\text{\textcircled{3}})$
FIG. 35E $\beta_{35}(T) = 1$ $\beta_{35}(G) = 1$ $\beta_{35}(C) = 1$ $\beta_{35}(A) = 1$ $$\begin{aligned}\beta_{34}(T) =\ &\beta_{35}(T) \times L_{35}(0) \\ +\ &\beta_{35}(G) \times L_{35}(1) \\ +\ &\beta_{35}(C) \times L_{35}(2) \\ +\ &\beta_{35}(A) \times L_{35}(3)\end{aligned}$$

SEQUENCE LISTING

<160> NUMBER OF SEQ ID NOS: 14

<210> SEQ ID NO 1
<211> LENGTH: 10
<212> TYPE: DNA
<213> ORGANISM: Artificial Sequence
<220> FEATURE:
<223> OTHER INFORMATION: Exemplary sequence

<400> SEQUENCE: 1

-continued

```
agtctaaccg                                                             10

<210> SEQ ID NO 2
<211> LENGTH: 39
<212> TYPE: DNA
<213> ORGANISM: Artificial Sequence
<220> FEATURE:
<223> OTHER INFORMATION: Exemplary sequence

<400> SEQUENCE: 2
tcgtgtgctt ccgaagacta tcctgctaag tgttttcac                             39

<210> SEQ ID NO 3
<211> LENGTH: 35
<212> TYPE: DNA
<213> ORGANISM: Artificial Sequence
<220> FEATURE:
<223> OTHER INFORMATION: Exemplary sequence

<400> SEQUENCE: 3
gcacacgaag gcttctgata ggacgattca caaaa                                 35

<210> SEQ ID NO 4
<211> LENGTH: 35
<212> TYPE: DNA
<213> ORGANISM: Artificial Sequence
<220> FEATURE:
<223> OTHER INFORMATION: Exemplary sequence

<400> SEQUENCE: 4
agcacacgaa ggcttctgat aggacgattc acaaa                                 35

<210> SEQ ID NO 5
<211> LENGTH: 35
<212> TYPE: DNA
<213> ORGANISM: Artificial Sequence
<220> FEATURE:
<223> OTHER INFORMATION: Exemplary sequence

<400> SEQUENCE: 5
cacgaaggct tctgatagga cgattcacaa aagtg                                 35

<210> SEQ ID NO 6
<211> LENGTH: 35
<212> TYPE: DNA
<213> ORGANISM: Artificial Sequence
<220> FEATURE:
<223> OTHER INFORMATION: Exemplary sequence

<400> SEQUENCE: 6
acacgaaggc ttctgatagg acgattcaca aaagt                                 35

<210> SEQ ID NO 7
<211> LENGTH: 35
<212> TYPE: DNA
<213> ORGANISM: Artificial Sequence
<220> FEATURE:
<223> OTHER INFORMATION: Exemplary sequence

<400> SEQUENCE: 7
cacacgaagg cttctgatag gacgattcac aaaag                                 35

<210> SEQ ID NO 8
<211> LENGTH: 16
<212> TYPE: DNA
```

```
<213> ORGANISM: Artificial Sequence
<220> FEATURE:
<223> OTHER INFORMATION: Exemplary sequence

<400> SEQUENCE: 8
tcgtgtgctt ccgaag                                                      16

<210> SEQ ID NO 9
<211> LENGTH: 13
<212> TYPE: DNA
<213> ORGANISM: Artificial Sequence
<220> FEATURE:
<223> OTHER INFORMATION: Exemplary sequence

<400> SEQUENCE: 9
actgggtaac atg                                                         13

<210> SEQ ID NO 10
<211> LENGTH: 11
<212> TYPE: DNA
<213> ORGANISM: Artificial Sequence
<220> FEATURE:
<223> OTHER INFORMATION: Exemplary sequence

<400> SEQUENCE: 10
actgggtaac a                                                           11

<210> SEQ ID NO 11
<211> LENGTH: 11
<212> TYPE: DNA
<213> ORGANISM: Artificial Sequence
<220> FEATURE:
<223> OTHER INFORMATION: Exemplary sequence

<400> SEQUENCE: 11
tcgtgtgctt c                                                           11

<210> SEQ ID NO 12
<211> LENGTH: 26
<212> TYPE: DNA
<213> ORGANISM: Artificial Sequence
<220> FEATURE:
<223> OTHER INFORMATION: Exemplary sequence
<220> FEATURE:
<221> NAME/KEY: misc_feature
<222> LOCATION: (2)..(12)
<223> OTHER INFORMATION: n is a, c, g, or t
<220> FEATURE:
<221> NAME/KEY: misc_feature
<222> LOCATION: (14)..(26)
<223> OTHER INFORMATION: n is a, c, g, or t

<400> SEQUENCE: 12
tnnnnnnnnn nngnnnnnnn nnnnnn                                           26

<210> SEQ ID NO 13
<211> LENGTH: 26
<212> TYPE: DNA
<213> ORGANISM: Artificial Sequence
<220> FEATURE:
<223> OTHER INFORMATION: Exemplary sequence
<220> FEATURE:
<221> NAME/KEY: misc_feature
<222> LOCATION: (2)..(12)
<223> OTHER INFORMATION: n is a, c, g, or t
<220> FEATURE:
<221> NAME/KEY: misc_feature
<222> LOCATION: (14)..(26)
<223> OTHER INFORMATION: n is a, c, g, or t
```

```
<400> SEQUENCE: 13
tnnnnnnnnn nngnnnnnnn nnnnnn                                    26

<210> SEQ ID NO 14
<211> LENGTH: 26
<212> TYPE: DNA
<213> ORGANISM: Artificial Sequence
<220> FEATURE:
<223> OTHER INFORMATION: Exemplary sequence
<220> FEATURE:
<221> NAME/KEY: misc_feature
<222> LOCATION: (1)..(13)
<223> OTHER INFORMATION: n is a, c, g, or t
<220> FEATURE:
<221> NAME/KEY: misc_feature
<222> LOCATION: (15)..(25)
<223> OTHER INFORMATION: n is a, c, g, or t

<400> SEQUENCE: 14
nnnnnnnnnn nnngnnnnnn nnnnnt                                    26
```

SYSTEMS AND METHODS FOR ERROR CORRECTION IN DNA SEQUENCING

RELATED APPLICATION(S)

This application is a division of U.S. patent application Ser. No. 12/910,751, entitled "Systems and Methods for Error Correction in DNA Sequencing," filed on Oct. 22, 2010, which claims priority pursuant to 35 U.S.C. § 119(e) to U.S. Provisional Patent Application Ser. No. 61/254,545, entitled "Error Correcting Codes Used in Sequencing Ligation," filed on Oct. 23, 2009, the entirety of which is incorporated herein by reference.

SEQUENCE LISTING

This application contains a Sequence Listing, which has been submitted in ASCII format via EFS-Web in parent application U.S. patent application Ser. No. 12/910,751 on Mar. 23, 2015, and is hereby incorporated by reference in its entirety. Said ASCII copy was named LT00073_ST25.txt, was created on Mar. 20, 2015, and was 3,469 bytes in size.

FIELD

The present disclosure generally relates to the field of DNA sequencing including systems and methods for detection and correction of errors or ambiguities encountered in or associated with sequencing of DNA samples.

BACKGROUND

In certain DNA sequencing systems, identities of nucleotides of a sample can be determined by identifying complementary nucleotides that hybridize to or pair or otherwise match with nucleotides of the sample. One or more of such complementary nucleotides may be part of a probe or probe set that can be used to test or interrogate the sample nucleotide sequence.

Typically, probes include a detectable feature such as chemical or physical features that can be identified under suitable conditions. As an example, dyes that fluoresce or otherwise emit an optical signal under suitable conditions can be used as detectable features. By detecting the feature (e.g., the fluorescence of a dye), information about the probe, and thus the portion of the sample where the probe hybridizes, pairs, or matches can be obtained.

Errors and ambiguities can be introduced or otherwise occur at or during various stages of sequencing and sequencing-related operations and processes. In certain situations, it can be impossible to even know that an error has occurred or an ambiguity exists. While it may in some situations be possible to resolve ambiguity or distinguish an error from correct but unusual or unexpected sequence information such as single nucleotide polymorphism, determining whether the sequence information is ambiguous, correct, or erroneous can typically only be detected by comparison of the sequence information with a reference. Further, even if the putative sequencing error or ambiguity is identified as a true error or ambiguity, there is often no mechanism or capability to correct the error or ambiguity without having to repeat some or all of the measurements.

SUMMARY

The present disclosure relates generally to methods for determining sequence information for nucleic acid samples but can also have applicability to determination of sequence information for other biopolymers such as, for example peptides or proteins. The present disclosure also relates generally to the detection, identification, resolution, and/or correction of errors and ambiguities in sequence information.

Using nucleic acids as an example, without limitation, some embodiments configure a template polynucleotide so as to allow testing, observing, or interrogating of one or more nucleotides, the number of nucleotides represented by the shorthand "K." The value of "K" is not limited to any particular range. Methods can further include testing, observing, or interrogating one or more of the K nucleotides so as to yield measurements of one or more detectable characteristics, the number of detectable characteristics represented by the shorthand "M." The value of "M" is not limited to any particular range. Measurements can also include data representative of one or more of the K nucleotides and also include redundant data that can be used for error or ambiguity detection.

In some embodiments, redundancy can be achieved by, for example, having a quantity $N^M$ greater than a quantity $L^K$, with each of the K nucleotides being one of L types, and with each of the M detectable characteristics being one of N types. The values of "L" and "N" are not limited to any particular range. In some embodiments, the quantity L includes quantity of 4 corresponding to nucleotide types A, C, G, and T. In some embodiments, redundancy can be achieved by selecting the quantity N and/or by selecting the quantity M.

In some exemplary and non-limiting embodiments, the quantity M can be represented as $M=K*S/P$ where S represents a number of unique hybridization, pairing, matching, interrogation, or probing steps and P represents a number of variable factors associated with one of more of those steps. Redundancy can be achieved by selecting the quantity S and/or by selecting the quantity P.

The present disclosure also provides methods involving decoding or interpretation of measurements to assist in determining whether a measurement or set of measurements includes any errors or ambiguities. In some embodiments, the method can include performing an error correction or ambiguity resolution based on one or more detected errors or ambiguities and one or more redundant data points. The present disclosure provides error detection and/or correction or ambiguity detection and/or resolution that does not require a reference sequence.

BRIEF DESCRIPTION OF THE DRAWINGS

FIGS. 20A-20C are representations of three distinct di-base encoding schemes capable of being utilized with the presently disclosed system;

FIG. 21 is a representation of multiple rounds of ligation-based sequencing being performed with distinct probe sets, and includes SEQ ID NO: 2;

FIGS. 35A-35E are various representations of steps performed by an embodiment of an algorithm of the system;

These and other aspects, advantages, and novel features of the present teachings will become apparent upon reading the following detailed description and upon reference to the accompanying drawings. In the drawings, similar elements have similar reference numerals.

DETAILED DESCRIPTION

Figure 1A:
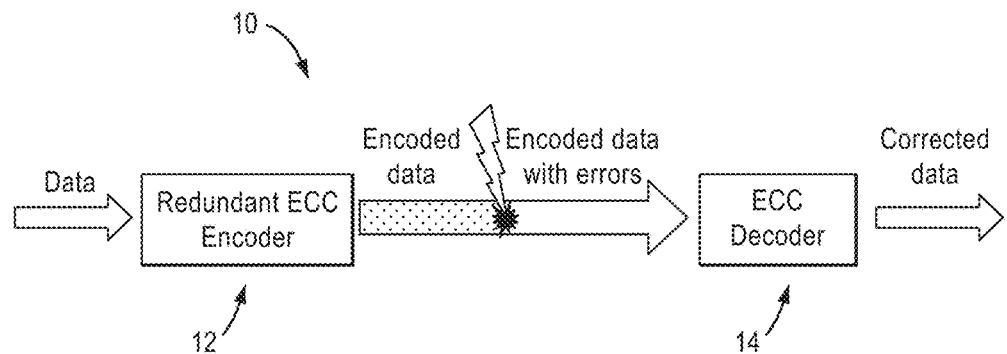
FIG. 1A is a block diagram of a preferred embodiment of the presently disclosed system.

Systems and methods of determining polymer sequence information, data analysis, error detection, error correction, ambiguity detection, and ambiguity resolution are provided herein. More specifically, the present disclosure provides systems and methods which detect and encode data while also introducing redundancy into the encoded data. Redundant data can be used for error detection and error correction or ambiguity detection and ambiguity resolution without necessarily having to repeat any data detection and/or measurement steps. This disclosure will generally use the phrases "error detection" and "error correction" and the like, but it will be understood that the disclosure and embodiments also relate to identification of ambiguities and resolution of ambiguities.

Error detection and correction can be performed in real-time, on-the-fly, downstream, or at a different time or place from data acquisition. While the presently disclosed encoding schemes and data correction mechanisms can be utilized and tailored towards a wide-range of fields, preferred embodiments are directed for purposes of exemplification herein towards polynucleotide sequencing applications. In reference-based sequencing, de novo sequencing, and other approaches, the present disclosure provides tools for acquiring and/or encoding nucleotide-related data in a manner which includes a degree of redundancy. Redundancy can assist in identifying and correcting errors or uncertainties during decoding or transformation of the data into sequence information.

The presently disclosed systems and methods can be utilized with virtually any type of polynucleotide sequencing system or method. For example, the encoding and error detection and correction schemes can be used with ligation-based systems, polymerase-based systems, hybridization-based systems, direct or indirect nucleotide identification systems, pyrosequencing, ion- or pH-based detection systems, electronic signature-based systems, etc. In a preferred embodiment, the systems and methods can be utilized with ligation-based DNA sequencing systems. In particular, the presently disclosed encoding schemes and accuracy enhancements tools can be utilized with systems such as the SOLiD DNA Sequencing System (Life Technologies, Carlsbad, Calif.). For purposes of this disclosure, various embodiments are exemplified for teaching purpose in connection with a ligation sequencing approach such as the aforementioned SOLiD system.

As discussed in greater detail below, the SOLiD DNA Sequencing System can be configured to perform multiple ligation rounds offset relative to one another such that each nucleotide is interrogated multiple times. During such interrogations, nucleotide specific signals are generated (e.g., fluorescent signals emitted by various nucleotide specific tags) wherein such signals can be considered the encoded data. That is, in some embodiments, nucleotides can be encoded into color data. Redundant data can be introduced to the encoded data by interrogating the data with distinct probe sets. For example, a ligation sequencing process can include multiple offset ligation rounds followed by at least one additional interrogation event with probes of a distinct probe set. That is, the system can perform an additional ligation round(s) configured to interrogate previously interrogated sites but further be configured to produce a distinct signal as compared to the signal generated during the first interrogation. Taken together, SOLiD's use of multiple ligation offsets and repeated interrogations with distinct probe sets has been shown to achieve base-call accuracy of 99.99%. Additional information regarding the SOLiD ligation sequencing system can be found in U.S. Patent Application Publication No. 2009/0062129, entitled "Reagents, Methods, and Libraries For Gel-Free Bead-Based Sequencing," the entirety of which being incorporated herein by reference.

FIG. 1A provides an overview of a preferred embodiment of the presently disclosed system 10. As shown, the system 10 can include a Redundant Error Correction Code ("ECC") Encoder 12 configured to encode data into encoded data. Again, the presently disclosed system can be utilized in various technologies and/or industries requiring such encryption techniques. In a preferred embodiment, the acquired data is related to, derived from, or otherwise representative of a nucleotide sequence. Those skilled in the art will appreciate that such data can be acquired and encoded by various mechanisms. For example, various sequencing platforms are known which dispose large amounts of polynucleotide samples across a substrate and seek to elucidate sequence information by various chemical, physical, and/or enzymatic reactions. For example, some platforms bind the samples to bead which are then immobilized on a substrate, some grow colonies of sample on the substrate, etc. Next, the samples can be hybridized with or otherwise integrated by a probe having (i) some specificity for one or more nucleotides or sequences of nucleotides and (ii) a tag (e.g., a fluorophore) wherein excitation of that tag can generate a signal indicative of the presence of the target. In some embodiments, the signal(s) generated can be collected as a data set, as a code, or can be converted into a code or other data form which can immediately or at some later time be transformed, interpreted, or decoded into information regarding base identification. As detailed herein, this data can be introduced to an ECC Decoder 14 configured to detect errors as well as correct such errors without having to repeat any earlier steps.

Errors can be introduced during data acquisition and encoding procedures in various manners. The explicit cause of such errors is often linked to the type of data being encoded. Taking ligation-based sequencing as an example, such systems can produce a clonal DNA sample either on a solid support (e.g., a bead) or as a colony directly on a substrate. A mixture of 4 probes can then be added to the sample wherein the 4 probes include, as a general non-limiting example: an A-specific probe, a T-specific probe, a C-specific probe, and a G-specific probe. As discussed in greater detail below, probes specific for various nucleotide combinations are provided herein which exhibit unexpected and superior accuracy results. The four probes are typically labeled with a tag capable of being distinguished from the tags of other members of the probe set. That is, the probes can be fluorescent probes, chemiluminescent probes, etc. In a preferred embodiment, fluorescent probes are utilized. For example, the four probes can be FAM, Cy3, TXR, and Cy5.

The sample is then excited 4 times in order to preferentially excite one of the tags during each of the 4 excitation procedures. For example, in the case of the fluorescent tags, a sample can be irradiated with an excitation source (e.g., a laser, an arc lap, an LED, etc.) specific or preferential for FAM, then specific or preferential for Cy3, then specific or preferential for TXR, and then specific or preferential for Cy5. The desired specificity or preferential collection of data from tags can also be accomplished in other ways, for example by illuminating with one or more excitation sources or wavelengths and filtering emissions from the sample. In an ideal world, the clonal sample would "light-up" only once and would be zero for the remaining 3 excitation steps. However, systems typically do not behave in an ideal manner and errors or ambiguity can be introduced. That is, some samples might not be purely clonal but rather have some amount of contamination. Further, sometimes probes can gather and/or hybridize imperfectly and thereby provide signals at incorrect locations and times. In view of these kinds of error-inducing situations, a singular or monolithic signal is not typically generated. Instead, a combination or mix of multiple signals is produced. In some embodiments, this mix can be considered a mix of 4 colors wherein each color is associated with one of the fluorescent tags. In such situations, each signal from each ligation cycle can be considered to give a set of 4 color likelihoods as opposed to an exact color read. These color likelihoods can form an initial element of the encoded data with some element of error introduced therein.

In view of above, acquiring, storing, and encoding large amounts of data into a code can increase the probability of encountering an error. Looking again the ligation-based DNA sequencing example, each ligation cycle of each round will generate 4 color-likelihoods for each cycle, which will then be repeated for some number of ligation rounds. These color-likelihoods will continue to generate the encoded data. However, the presently disclosed system is configured such that successive data encoding events (e.g., ligation cycles or ligation rounds) not only introduces potential error and/or ambiguities into the code but also introduces a degree of redundancy into the code which allows a ECC Decoder 14 to not only decipher the code but to do so in such a manner which allows for error/ambiguity detection and real-time correction/resolution. That is, the presently disclosed encoding schemes are capable of allowing the ECC Decoder 14 to not only detect when an error or ambiguity appears to have occurred but also to determine what the correct result should have been, or at least what was the most probable correct result. The Decoder 14 is further capable of evaluating the various likelihoods/probabilities to therefore determine a most probable result without any specific error correction step.

Figure 1B:
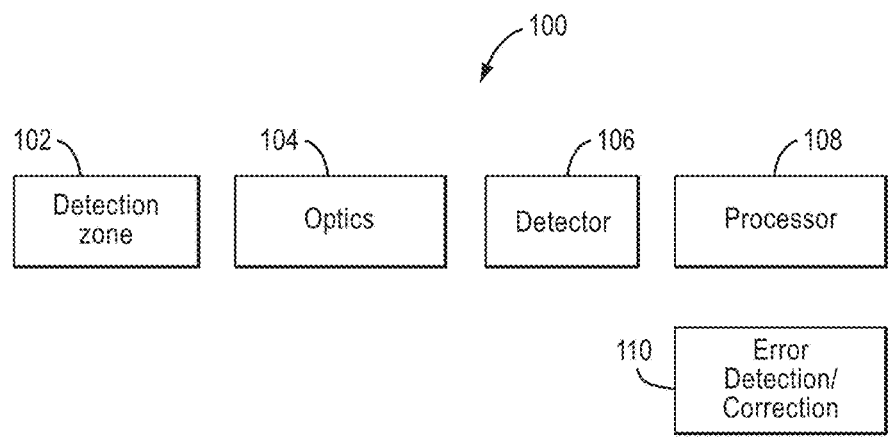
FIG. 1B is a block diagram of some embodiments of a DNA sequencing system having a component that allows detection and or correction of errors and/or ambiguities.

FIG. 1B shows a general block diagram of an embodiment of a sequencing system 100 having various components that can facilitate detection and identification of a sequence of nucleotides in a given sample. In some embodiments, the system 100 can include a detection zone 102 where the sample being sequenced is subjected to various reactions associated with the sequencing process. Such a detection zone can include, for example, a flow cell, various embodiments of which are disclosed in Assignee's co-pending U.S. patent application Ser. No. 12/873,190, filed on Aug. 31, 2010, entitled "Low-Volume Sequencing System and Method of Use," the entirety of which being incorporated herein by reference thereto. As will be understood by those skilled in the art, various such detection zone configurations are also possible and within the spirit and scope of the present disclosure.

The system 100 can also include an optics component 104 configured to form images of the detection zone, and such images can be formed via a detector 106. The system 100 can also include a processor 108 configured to control one or more functionalities associated with various components of the system 100. In certain embodiments, the processor 108 can be configured to perform one or more processes as described herein. In certain embodiments, the processor 108 can also be configured to control one or more operations (e.g., detection zone control, optics control, exposure control, detector control, signal acquisition, signal processing, analysis of data, etc.) associated with the sequencing system 100. Various embodiment of the optics component 104 are disclosed in Assignee's co-pending U.S. patent application Ser. No. 12/873,132, filed on Aug. 31, 2010, entitled "Fast-Indexing Filter Wheel and Method of Use," the entirety of which being incorporated herein by reference thereto.

In certain embodiments, the analysis of data may be performed by the processor 108. The processor 108 may further be configured to operate in conjunction with one or more other processors. The processor's components may include, but are not limited to, software or hardware components, modules such as software modules, object-oriented software components, class components and task components, processes methods, functions, attributes, procedures, subroutines, segments of program code, drivers, firmware, microcode, circuitry, data, databases, data structures, tables, arrays, and variables. Furthermore, the processor 108 may output a processed signal or analysis results to other devices or instrumentation where further processing may take place. The system 100 can also include a component 110 configured to detect and correct errors associated with sequencing processes. In certain embodiments, the error detection and correction component 110 can be configured to perform one or more of the features as described herein.

The above-described system can be utilized to generate encoded redundant data from a polynucleotide template. Redundancy allows for error correction by providing multiple and/or distinct measurements of data such that these multiple measurements can be compared against one another to determine if the measurements are correct. Redundancy can also require that multiple interrogations are required to determine a true value of data. In the context of DNA sequencing, redundancy can be introduced in various manners. For example, taking 3 successive nucleotides, the first and second nucleotides can be interrogated to give a first signal, and the second and third nucleotides can be interrogated to give a second signal. Thus, multiple interrogation events can be utilized to interrogate a single data point. Additionally, the system can interrogate the same group of nucleotides with distinct probes thereby generating distinct signals which are each indicative of the same data point (i.e., nucleotide). As detailed below, this approach can provide a powerful accuracy enhancing sequencing platform when combined with the use of carefully selected and constructed probe sets.

Figure 2A:
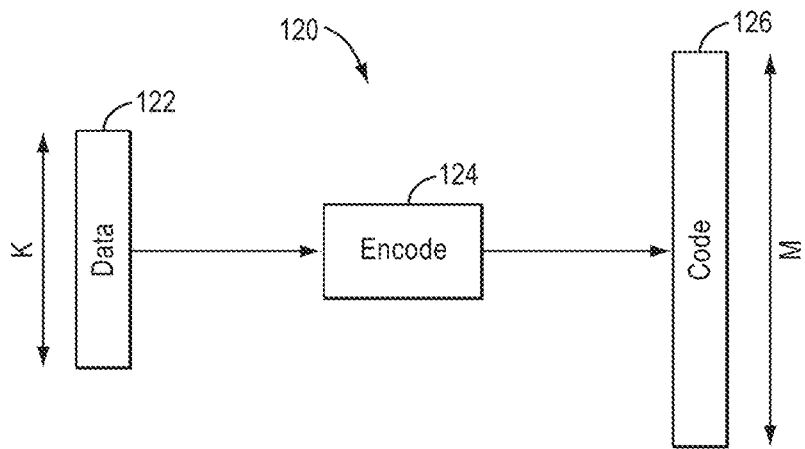
FIG. 2A is another block diagram of some embodiments wherein the error or ambiguity detection and correction component of FIG. 1B can include a feature where data associated with DNA sequencing can be encoded so as to introduce redundancy suitable for detection and correction of errors and/or ambiguities.

FIG. 2A shows a block diagram of a configuration 120 where redundancy can be introduced to a block of data 122 having a length K. The block of data 122 can represent, for example, a sequence of nucleotides in a DNA sample strand being analyzed. In such a context, the length K can represent number of bases (if a single strand) or base pairs (if a double strand) in the sample strand.

For the purpose of description, a unit (such as a base or base pair) in the length K may be referred to as a "digit", "symbol", or other term. Such terms are commonly associated with error correcting code ("ECC") terminology, however, as used herein, such terms are not necessarily limited by previously-cited definitions. Thus, as used herein, these terms may reflect multiple values (e.g., those values associated with the base sequences A, C, G, T). Therefore, the data 122 can be referred to as a K-digit data, and/or K-symbol data interchangeably without limiting or departing from the scope of the present disclosure. In the context of a sequence of bases, each symbol can represent one of four bases A, C, G, T.

As shown in FIG. 2A, the K-symbol data 122 is shown to be encoded by an encoding component 124 so as to yield a code 126 having a length M. Similar to data length K, a unit in the length M may also be referred to as a symbol or some other term commonly associated with ECC terminology. Thus, the code 124 can be referred to as an M-symbol code. In the context of certain fluorescence-based sequencing processes, each symbol can represent one of a number of fluorescence colors.

In general, redundancy introduced in the foregoing manner can result in information content of the code 126 being greater than information content of the data 122. Thus, redundancy can be considered to be introduced to the data 122 if $N^M > L^K$, where M (referred to as the length in FIG. 2A) represents the number of detectable characteristics (such as fluorescence colors) with each characteristic being one of N discrete values, and K (referred to as the length in FIG. 2A) represents the number of unknown characteristics with each characteristic being one of L discrete values. In the context of a sequence of bases (where each base can be one of four bases A, C, G, and T), L=4. In the context of a fluorescence-based detection context, an example 4-color configuration corresponds to N=4. As described herein, various configurations associated with sequencing operations can be selected so as to yield the redundancy condition $N^M > L^K$.

Figure 2B:
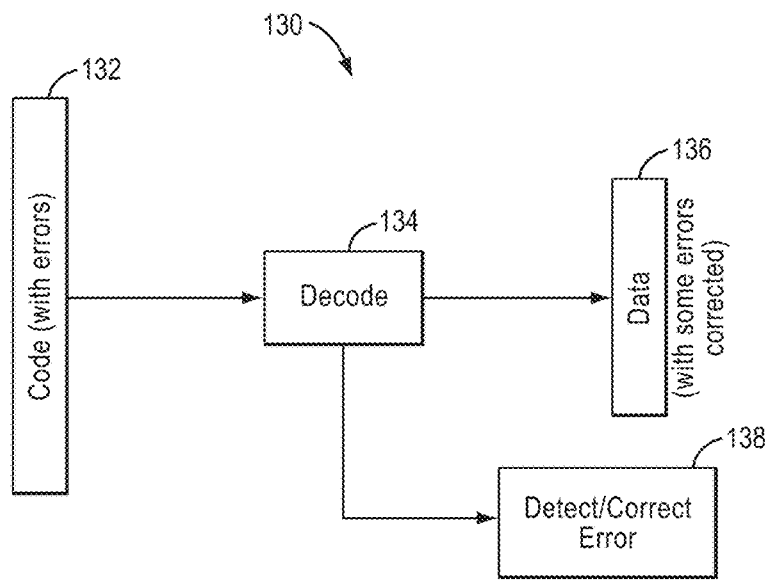
FIG. 2B is another block diagram of some embodiments wherein the error and/or ambiguity detection and correction component of FIG. 1B can include a feature where the coded measurements having the redundancy can be decoded so as to allow extraction of the data, as well as information for detection and correction of errors and/or ambiguities.

In certain embodiments, coded information having redundancy can be decoded so as to facilitate detection of sequencing errors and correction of such detected errors and/or detection and/or resolution of ambiguity (i.e., there does not necessarily include an error correction but rather a resolution of some uncertainty or ambiguity). FIG. 2B shows a block diagram of a configuration 130 where a code 132 having redundancy (e.g., generated by the encoder 124 of FIG. 2A) can be decoded by a decoding component 134. Such an operation can yield data 136 extracted from the code 132, as well as information (depicted as component 138) that facilitates detection and correction of an error that may have occurred between data 122 "before errors" and data 136 "after errors." It will be appreciated that "error detection" and "error correction" may be separated into discrete tasks or combined in a joint or serial manner. In various embodiments the decoder may be implemented to determine the Data that, if encoded using the Encoder, may yield a Code that is similar or most similar to the observed "Code with errors". As will be appreciated, such an approach may be used to achieve "error correction" without an explicit "error detection" step or routine recognizing that in various instances actual errors may take place in "Code"-space and not necessarily in "Data"-space.

Figure 2C:
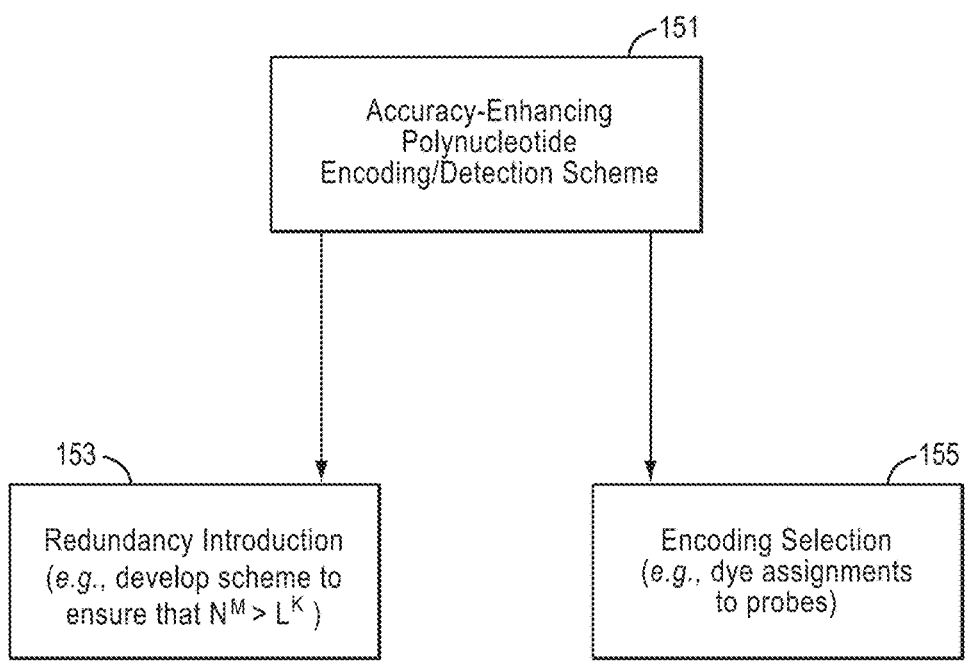
FIG. 2C is another representation of some embodiments of the presently disclosed accuracy-enhancing encoding/decoding scheme.

FIG. 2C provides another representation of the presently disclosed error-correction scheme wherein the introduction or redundancy and encoding selection are illustrated as distinct processes. That is, an accuracy-enhancing polynucleotide encoding/detection scheme 151 of the present disclosure can be considered to include a Redundancy Introduction Process 153 which can include, for example, transforming data into encoded redundant data where, for example $N^M > L^K$. The scheme 151 can also include Encoding Selection 155 which can include dye assignment to probes, etc. Those skilled in the art will appreciate that these distinct "Processes" are shown as such merely for explanatory purposes and various steps in the presently disclosed scheme can be considered to fall within either or both such blocks 153, 155.

Figure 3:
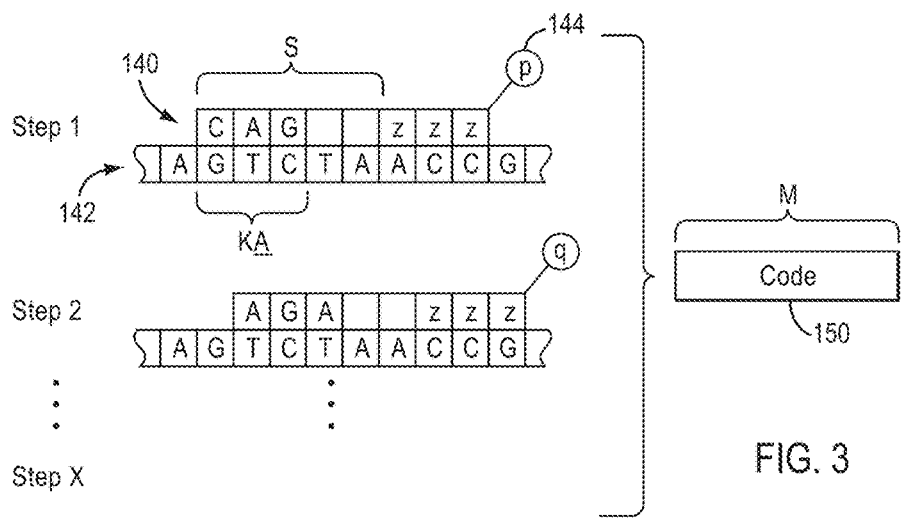
FIG. 3 is a representation of some embodiments where redundancy can be introduced to a measurement by interrogating a selected sequence of nucleotides a number of times at different offsets between the nucleotide sequence and interrogating probes, and includes SEQ ID NO: 1.

Redundancy can be introduced and incorporated with data in various manners. For example, FIG. 3 shows a sequencing situation where KA symbols of a polynucleotide template strand 142 are being interrogated by a probe 140. As shown, the probe 140 can be configured to include KA symbols that complement the KA symbols of the template strand 142. Thus, example nucleotide sequence GTC of the template 142 can hybridize with the complementary sequence CAG of the probe 140.

The example probe 140 can have one or more additional symbols so as to yield S symbols. In some embodiments, as shown in FIG. 3 and described in detail below, the probe 140 can also include additional bases, represented as "Z", which can be cleaved during processing. In certain embodiments, such S symbols can allow S rounds of interrogation where each interrogation round is performed at a selected offset of the probe 140 relative to the template strand 142. For example, a probe having the CAG sequence is shown to hybridize to the GTC sequence of the template strand in Step 1. In Step 2, another probe having an AGA sequence is shown to hybridize to a TCT sequence on the template strand, where the TCT sequence is offset from the GTC sequence of Step 1 by one nucleotide. Such offset interrogation can be performed at least S times.

In FIG. 3, the example probe 140 is shown to have detectable labels 144 indicated as "p" in Step 1 and "q" in Step 2, etc. In some embodiments, each of the labels 144 ("p," "q," etc.) can belong to a same group and have a unique assignment of, for example, a dye color based on the probe's nucleotide sequence. For example, the probe having the CAG sequence (Step 1) can be assigned with one of a number of dyes in a unique manner. Similarly, the probe having the AGA sequence (Step 2) can be assigned with one of the number of dyes in a unique manner.

In some embodiments, the probes 140 can also belong to two or more different groups, where each group has a unique dye assignment scheme for its labels. For example, a first group of probes can have a unique assignment of dye color for the probe sequence CAG of Step 1; and a second group of probes can have another unique assignment of dye color for the same probe sequence CAG of Step 1. As described herein, such different groups of probes can allow contribution of redundancy in certain situations. For example, if probes belonging to one group are utilized, redundancy can be represented by the number of rounds of offset interrogations (e.g., in FIG. 3, S rounds); and interrogation of a given offset more than once is simply repetitive and does not contribute to redundancy. However, if a given offset is interrogated again by a probe from a different group, then such an interrogation can contribute additional useful information for the purpose of redundancy.

Considered in another manner, the sequencing procedure may be likened to a pair of nested FOR-loops. The outer loop may be referred to as Primer Rounds, and the inner loop a Cycle. In the first primer round, first cycle, a probe (e.g., probe 140) may attach to nucleotides 1 through 5. In first primer round, second cycle (following cleavage of the "ZZZ" nucleotide sequence of probe 140), a probe may attach to nucleotides 6 through 10. Subsequent cycles within the same primer rounds may examine positions 11-15, 16-20, and so forth, until a reset is performed and a new primer round started (e.g., Step 2 in FIG. 3). At the second primer round, a probe may be attached at positions 2-6 at the first cycle, and 7-11, 12-16, 17-21, etc, at subsequent cycles. Similarly, Primer round 3 may examine positions 3-7, 8-12, etc, and Primer round 4 examine positions 4-8, 9-13, etc, with Primer round 5 examining positions 5-9, 10-14, etc. Referring to FIG. 3, the variable "X" can be considered to represent the number of Primer Rounds which may or may not equal "S". That is, as described in greater detail below, the total number of Primer Rounds can include at least one additional round performed with a distinct probe set.

In FIG. 3, X rounds of interrogation (which each include any number of "cycles") are depicted as yielding a code 150 having a length of M. As described herein, redundancy can be considered to be satisfied if $N^M > L^K$. In the context of sequencing operations such as that shown in FIG. 3, the quantity M (number of detectable characteristics) can be represented as $M = K*(X/S)$, where S represents the number of offsets (e.g., 5 in FIG. 3) and X represents the number of unique rounds (e.g., 5 in FIG. 3 due to 5 offsets). As described herein, the quantity X can include the number of offset measurements, as well as measurement(s) of a same offset using probes from different group(s). Thus, it will be appreciated that the number of primer rounds X need not necessarily be equal to the number of unique primer offsets S. As such, the value of X and S may be independently determined.

In FIG. 3, L=4 (corresponding to 4 types of bases); thus, redundancy can be achieved if $N^{K*(X/S)} > 4^K$. Values for N, X, and/or S can be selected so as to meet the redundancy requirement. For example, for a system that uses 4 types of dyes (N=4), redundancy can be achieved if $K*(X/S) > K$, or X>S. For a system that utilizes S offsets, the redundancy requirement of X>S can be achieved by, for example, performing S offset measurements plus one or more measurements (at one or more of the same offset values) using probes belonging to different group(s). Examples of such redundancy-introducing methods are described herein in greater detail.

In the context of L=4, the redundancy requirement of $N^{K*(X/S)} > 4^K$ can also be achieved by selecting an appropriate value for the number of dye types. For example, and as shown in a configuration 160 of FIG. 4A, if 5 types of dyes 164 (N=5) are provided for probes 162, the redundancy requirement becomes $5^{K*(X/S)} > 4^K$. Thus, even if only S rounds of unique measurements (X=S) are made, the redundancy requirement is met, since $5^{K*(S/S)} > 4^K$, or $5^K > 4^K$.

In certain embodiments, an effective value for N can be made relatively large by providing more than one dye per probe. Such an increase in N can allow one or more of the other parameters to be adjusted (e.g., reduced) accordingly, and yet satisfy the redundancy requirement.

Figure 4A:
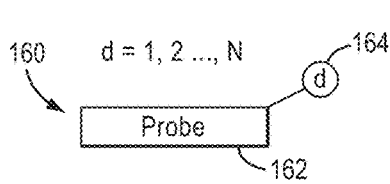
FIGS. 4A and 4B are representations of some embodiments where redundancy can be introduced to a measurement by configuring the probes with detectable dyes in various manners.
Figure 4B:
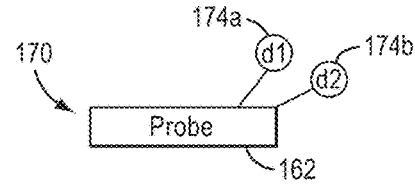

For example, FIG. 4B shows a configuration 170 of a probe 172 having two dyes d1 and d2 (174a, 174b). If each of the two dyes can be one of four types, the value for N can be represented as $2^4 - 1$ possible combinations of the two dyes unique combinations (for example, 11, 12, 13, 14, 22, 23, 24, 33, 34, 44 where 12, for example, may be optically indistinguishable from 21). With such a relatively large value for N, the quantity X (number of unique measurements) can be less than S (number of offsets) and yet satisfy the redundancy condition $N^{K*(X/S)} > L^K$, which can also be expressed as $K*(X/S)*\log N > K*\log L$, or $(X/S)*\log N > \log L$. Thus, for example, if X=3 for the S=5 configuration, the redundancy requirement is met, since $(3/5)*\log(15) > \log(4)$, or 0.71>0.60.

In another embodiment, a sequencing reaction may be performed on a collection of substantially identical or identical polynucleotide clones in parallel. In this case where there may be a relatively large number of clones, a relatively large number of identical probes anneal to them during one cycle, and it may be the joint fluorescence of these probes that may be being measured by the optics. In this context, it may be suggested that a particular probe sequence, "ACTGC", and dyes a,b,c,d, could simultaneously have a probe ACTGC-a and ACTGC-b in the mixture (as distinguished from multiple probe sets here both probes may be in a single set). With this, if a complementary polynucleotide is being sequenced, probe ACTGC-a may bind to roughly a half of the clones and ACTGC-b to the other half. It may then be observed that both colors a and b are found with half the intensity. For example, for an arbitrary probe sequence, one may select a single probe type with one of the four dyes, or a mix of two probes with different dyes (6 possibilities), or a mix of three probes (4 possibilities) or a mix of four probes with each dye—15 options altogether.

Figure 5:
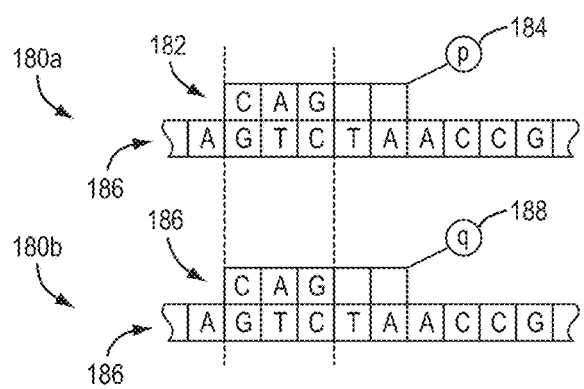
FIG. 5 is a representation of shows some embodiments where redundancy can be introduced to a measurement by interrogating the same portion of the nucleotide sequence two or more times using differently configured probes, and includes SEQ ID NO: 1.

Contribution to redundancy can also be made by interrogating same K symbols of bases more than once with different probes. FIG. 5 shows an example of such interrogations. In a first interrogation 180a, an example sequence GTC is shown to be interrogated by a first probe 182 having a dye "p" 184. The dye 184 can be one of a number of types (e.g., one of four types of dyes). In a second interrogation 180b, the same sequence GTC is shown to be interrogated by a second probe 186 having a dye "q" 188. The dye 188 can be one of a number of types (e.g., one of four types of dyes).

In certain embodiments, each of the dyes 184, 188 can be selected from four types of dyes (N=4). Thus, the probes 182, 186 may or may not have same dye. In certain embodiments, difference between the probes 182, 186 can be achieved due to a difference in how such dyes are assigned, even if the probes end up with same dye.

In certain embodiments, the first probe 182 can be part of a first group of probes, where each probe in the group is assigned a dye based on an assignment scheme unique to the first group. Similarly, the second probe 186 can be part of a second group of probes, where each probe in the group is assigned a dye based on an assignment scheme unique to the second group. Examples of such unique assignments are described herein in greater detail.

As described in reference to FIGS. 3-5, redundancy can be introduced by one or more different manners. For example, redundancy can be introduced by configuring the probes in certain manners. Redundancy can also be introduced by interrogating the template strand in certain manners.

Figure 6:
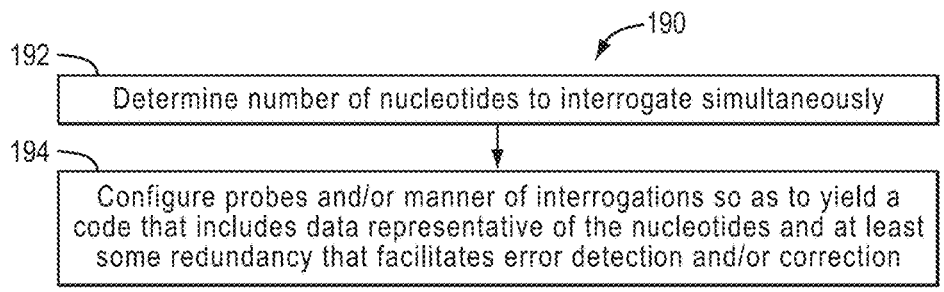
FIG. 6 is a flow-chart of some embodiments wherein a process can be implemented to configure interrogating probes and/or manner of interrogation so as to introduce redundancy.

FIG. 6 shows a process 190 that can be implemented to introduce redundancy to measurements. In a process block 192, a number of nucleotides to be interrogated can be determined. In certain embodiments, such number of nucleotides can be interrogated substantially simultaneously. In a process block 194, probes and/or manner of interrogations can be configured so as to yield a code that includes data representative of the number of nucleotides, and at least some redundancy that facilitates error detection and correction.

Figure 7:
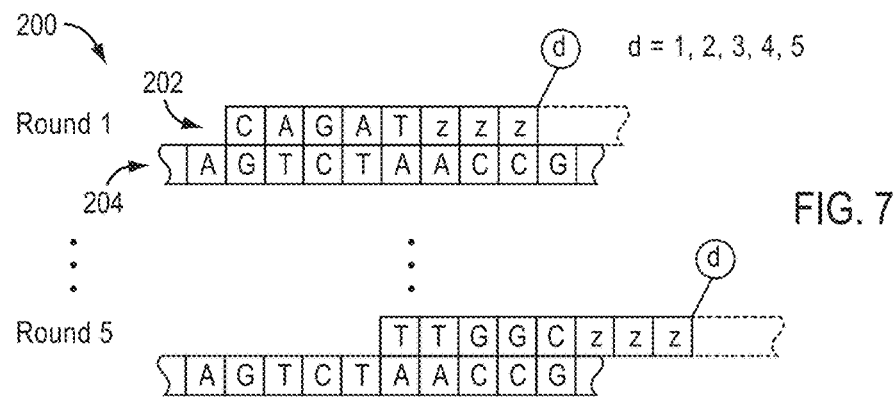
FIG. 7 is a representation of some embodiments where redundancy can be introduced to a measurement by configuring the probes with detectable dyes in various manners, and includes SEQ ID NO: 1.

FIGS. 7-12 provide additional examples of configurations and processes that can be implemented to introduce redundancy as described by way of examples in reference to FIGS. 4 and 5. More particularly, FIG. 7 shows a more specific example configuration 200 of the redundancy-introducing configuration of FIG. 4A. As shown, a template strand 204 is probed by probes 202 in five offset rounds. In Round 1, a probe having a sequence CAGAT is shown to hybridize to a 5-symbol sequence GTCTA on the template strand 204. In Round 2 (not shown), another probe having a sequence AGATT hybridizes to a shifted 5-symbol sequence TCTAA on the template 204. Additional rounds are performed on progressively shifted 5-symbol sequences, and in Round 5, a probe having a sequence complementary to the 5-symbol shifted template sequence is shown to be hybridized.

As shown in the example configuration of FIG. 7, each of the dyes assigned to the probes can be one of five types (d=1, 2, 3, 4, 5) such that N=5. As described herein, use of five types of dyes can satisfy the redundancy requirement even when each offset template sequence is interrogated only once.

Figure 8:
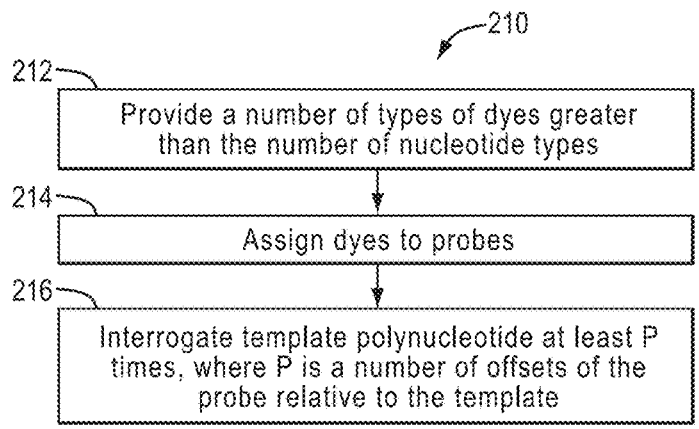
FIG. 8 is a flow-chart which shows a process that can be implemented to facilitate the example configuration of FIG. 7.

FIG. 8 shows a process 210 that can be implemented to facilitate the example configuration 200 of FIG. 7. In a process block 212, a number of types of dyes greater than the number of nucleotide types can be provided. In FIG. 7, the number of nucleotide types is four (L=4), and the number of types of dyes is 5 (N=5). In a process block 214, dyes can be assigned to probes having different K-symbol sequences. In a process block 216, a template strand can be interrogated at least P times, where P represents a number of offsets of the probe relative to the template. In FIG. 7, the template is interrogated five times at five different offsets.

In some respects, the aforementioned multi-dye example bears similarities to the dye-combinations in previous examples, and thus the formula $N^{K*(X/S)} > L^K$ applies. Another approach to analysis instead of introducing P, says that the number of primer rounds $X > S*(\log L)/(\log N)$. With S=5, N=5, L=4, this means X>4.3, which is satisfied for X=5. In various embodiments, this reflects an example of a special case in that with X<=5 one probe set may be used (multiple probe sets may be used when primer rounds reuse the same offset, and there are S=5 possible offsets). Additionally, if even more dyes are used, for example N=7, then X>5*log 4/log 7, i.e., X>3.5, and this may suggest that X=4 is redundant. Consequently, it will be appreciated that $S*(\log L)/(\log N)$ may reflect the lower bound on X.

Figure 9:
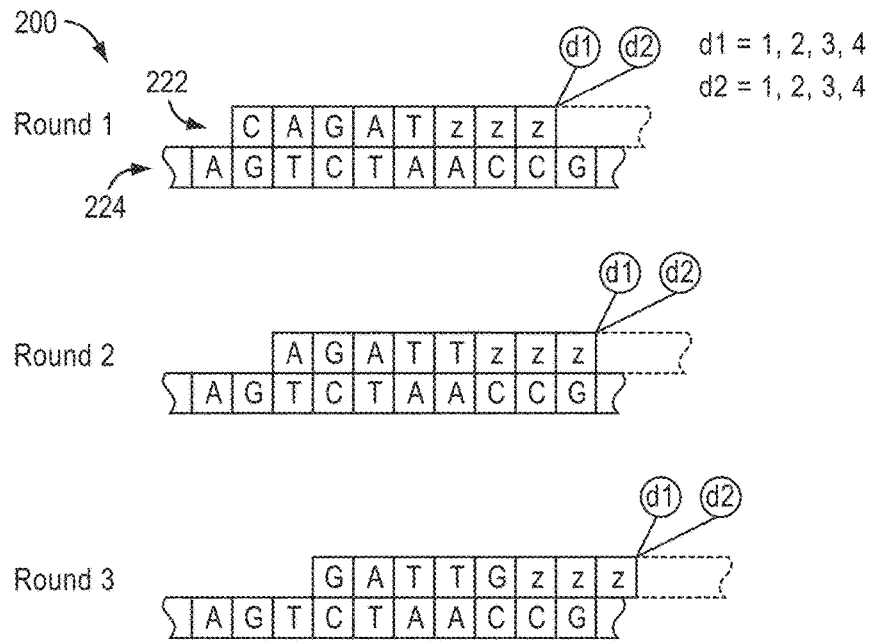
FIG. 9 is another representation of some embodiments where redundancy can be introduced to a measurement by configuring the probes with detectable dyes in various manners, and includes SEQ ID NO: 1.

FIG. 9 shows a more specific example configuration 220 of the redundancy-introducing configuration of FIG. 4B. As shown, a template strand 224 is shown to be probed by probes 222 in three offset rounds. In Round 1, a probe having a sequence CAGAT is shown to hybridize to a 5-symbol sequence GTCTA on the template strand 224. In Round 2, another probe having a sequence AGATT is shown to hybridize to a shifted 5-symbol sequence TCTAA on the template 224. In Round 3, another probe having a sequence GATTG is shown to hybridize to a shifted 5-symbol sequence CTAAC on the template 224.

As shown in the example configuration of FIG. 9, each of the probes is shown to have two dyes d1 and d2; and each of the two dyes d1 and d2 can be one of four types (d=1, 2, 3, 4) such that combined value for N is 15 as described in reference to FIG. 4B. As described herein, use of two dyes per probe can satisfy the redundancy requirement even when a K-symbol template sequence is interrogated at a number of offsets that is less than the probe's offset capacity S (e.g., S=5 in the example configuration 220 of FIG. 9).

Figure 10:
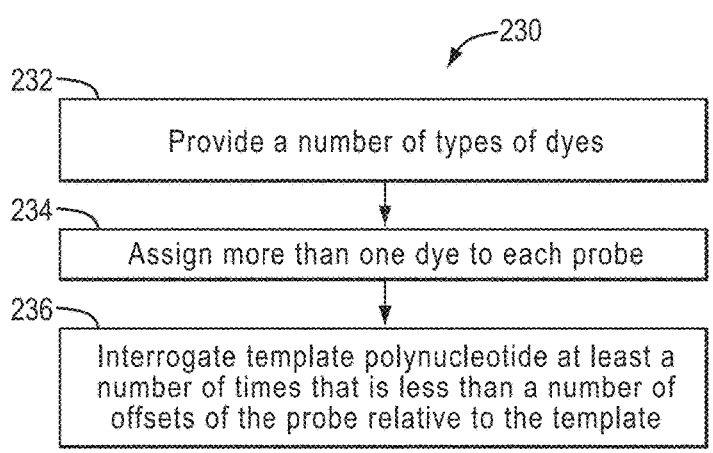
FIG. 10 is a flow-chart which shows a process that can be implemented to facilitate the example configuration of FIG. 9.

FIG. 10 shows a process 230 that can be implemented to facilitate the example configuration 220 of FIG. 9. In a process block 232, a number of types of dyes can be provided. In certain embodiments, the number of types of dyes can be at least as much as the number of types of nucleotides (L=4); thus, in FIG. 9, the number of types of dyes can be four. In a process block 234, more than one dye can be assigned to each of the probes having different K-symbol sequences. In FIG. 9, two dyes (each being one of four types) can be assigned to each of the probes so as to yield a combined value of 15 for the quantity N. In a process block 236, a template strand can be interrogated at least a number of times that is less than the probe's offset capacity. In FIG. 9, the probe's offset capacity S=5, and the template strand is interrogated only three times at different offsets.

Figure 11:
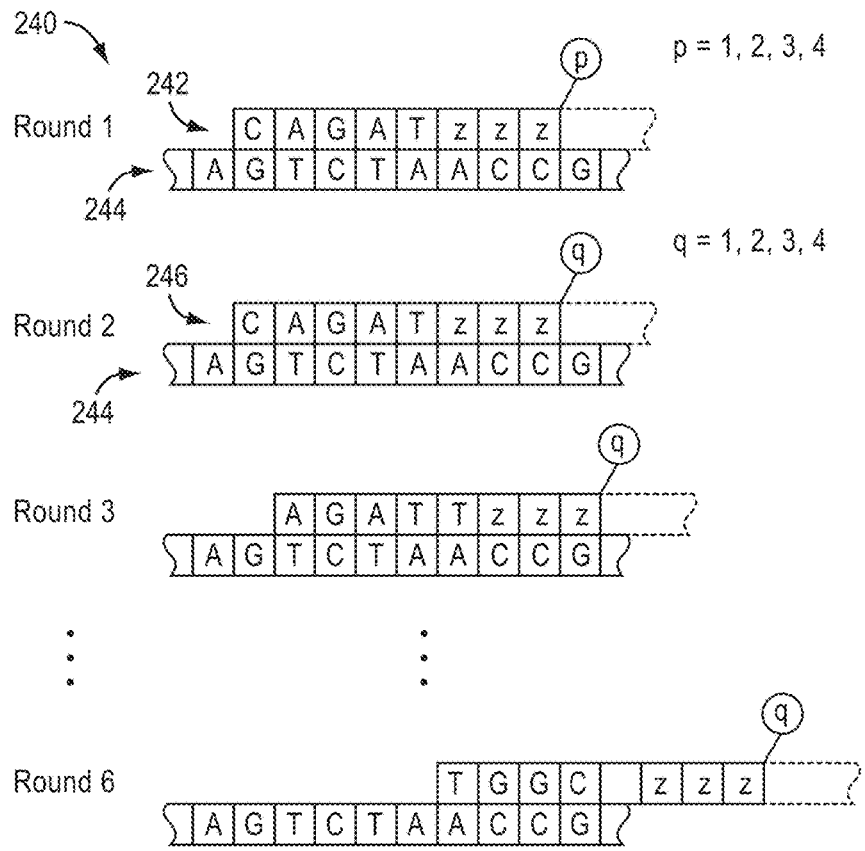
FIG. 11 is a representation of some embodiments where redundancy can be introduced to a measurement by interrogating the same portion of the nucleotide sequence two or more times using differently configured probes, and includes SEQ ID NO: 1.

FIG. 11 shows a more specific example configuration 240 of the redundancy-introducing configuration of FIG. 5. As shown, a template strand 244 is shown to be probed by probes belonging to different groups. For the purpose of description of FIG. 11, probes in a first group are indicated as "p," and probes in a second group are indicated as "q." In Round 1, a probe "p" having a sequence CAGAT is shown to hybridize to a 5-symbol sequence GTCTA on the template strand 244. In Round 2, a probe "q" having a sequence CAGAT is shown to hybridize to the same 5-symbol sequence GTCTA on the template strand 244. In Round 3, another probe "q" having a sequence AGATT is shown to hybridize to a shifted 5-symbol sequence TCTAA on the template 244. Additional rounds are performed on progressively shifted 5-symbol sequences, and in Round 5, a probe "q" having a sequence complementary to the 5-symbol shifted template sequence is shown to be hybridized.

In the example configuration of FIG. 11, six rounds of interrogation are performed by five offset rounds with probes "q" and one round with probe "p." It will be understood that other combinations of numbers of round(s) for each group of probes are also possible. Further, the offset location of the two-round measurements can also be different than the example shown in FIG. 11.

Figure 12:
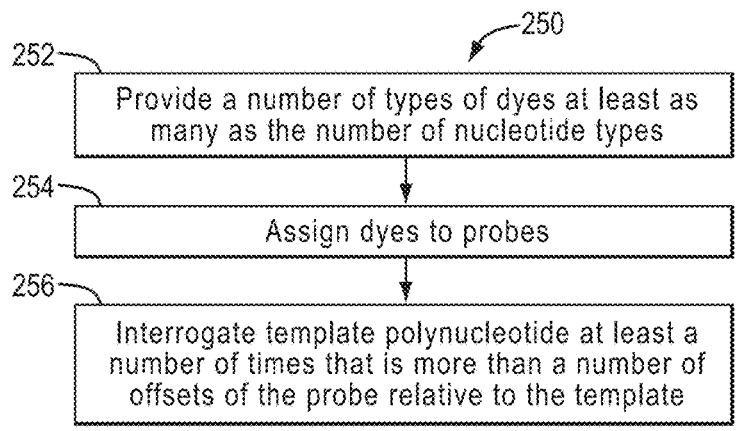
FIG. 12 is a flow-chart which shows a process that can be implemented to facilitate the example configuration of FIG. 11.

FIG. 12 shows a process 250 that can be implemented to facilitate the example configuration 240 of FIG. 11. In a process block 252, a number of types of dyes can be provided. In FIG. 11, the number of types of dyes is 4 (N=4) and same as the number of types of nucleotides (L=4). In a process block 254, dyes can be assigned to probes in two groups "p" and "q." Examples of such dye assignments are described herein in greater detail. In a process block 256, a template strand can be interrogated at least a number of times that is more than a number of offsets of the probe relative to the template. Such interrogation(s) beyond the probe's offset capacity can be provided by one or more additional groups of probes. In FIG. 12, there are two groups of probes ("p" and "q"), and probes of one group ("q") provide five rounds, and the sixth interrogation is provided by "p" probe.

Figure 13:
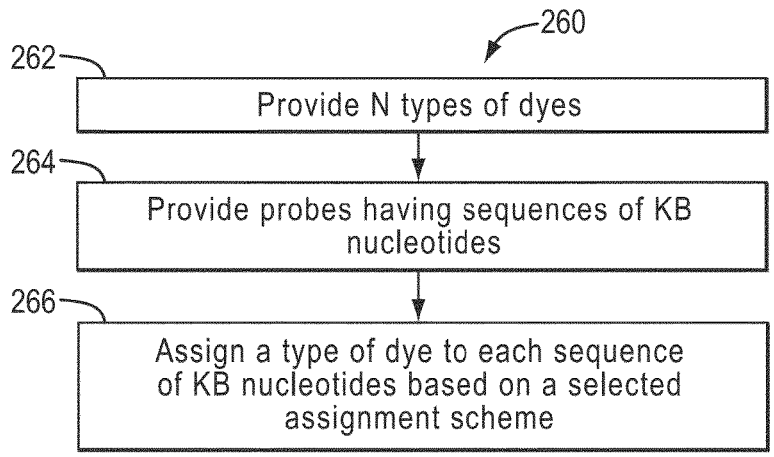
FIG. 13 is a flow-chart which shows a process that can be implemented to configure interrogating probes so as to introduce redundancy to measurements.
Figure 14:
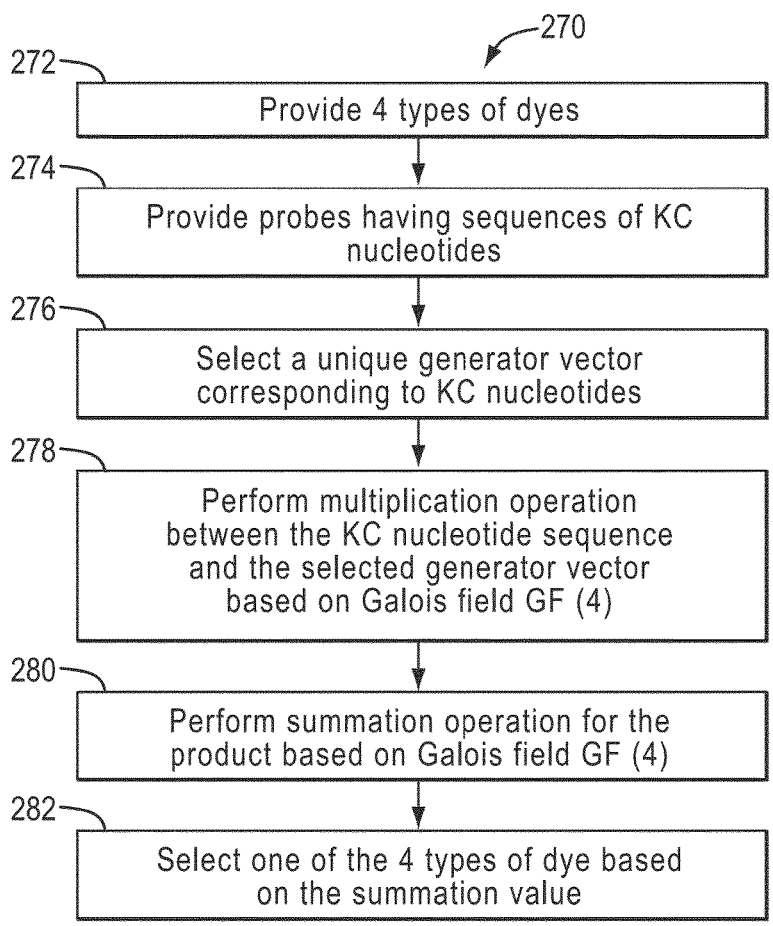
FIG. 14 is a flow-chart which shows a process that can be implemented to configure interrogating probes so as to introduce redundancy to measurements.

The presently disclosed encoding schemes utilize probes having uniquely assigned dyes which complement the redundancy to provide the ability to detect and correct errors. FIGS. 13-15 show non-limiting examples of how such unique dye assignments can be achieved. Although dyes are used as examples of detectable components, it will be understood that other types of detectable components having different detection properties can also be used. For example, detectable components can be based on emissions other than fluorescence. In another example, detectable components can be based on emission of electromagnetic radiation other than those generally in the visible range.

FIG. 13 shows a process 260 that can be implemented to assign dyes to probes. In a process block 262, N types of dyes can be provided. In a process block 264, probes having KB-symbol nucleotide sequences can be provided. In a process block 266, the process 260 provides one of the N types of dyes to each KB-symbol sequence based on a selected assignment scheme.

In certain embodiments, the process 260 can generate one group of probes, where each of the probes in the group undergo dye-assignment based on the same selected assignment scheme. In situations where one or more groups of probes are desired, a process similar to the process 260 can be performed using different assignment scheme(s).

FIG. 14 shows a process 270 that can be implemented as a more specific example of the process 260 of FIG. 13. More particularly, the process 270 can be configured to generate probes where four types of dyes are utilized. Thus, in a process block 272, four types of dyes can be provided. In a process block 274, probes having KC-symbol nucleotide sequences can be provided. In a process block 276, a unique generator vector corresponding to KC-symbols can be selected. Steps of process blocks 272, 274, and 276 can be performed once while the remaining steps (process blocks 278, 280, 282 can be performed separately for each probe). That is, in a process block 278, a multiplication operation between the KC-symbol sequence of a given probe and the selected generator vector can be performed. In certain embodiments, the generator vector can be based on a known Galois field GF(4). In a process block 280, a summation operation can be performed on the product resulting from the multiplication operation of the process block 278. In certain embodiments, such summation can be based on the Galois field GF(4). In a process block 282, one of the four types of dye can be selected based on the summation value.

Figure 15A:
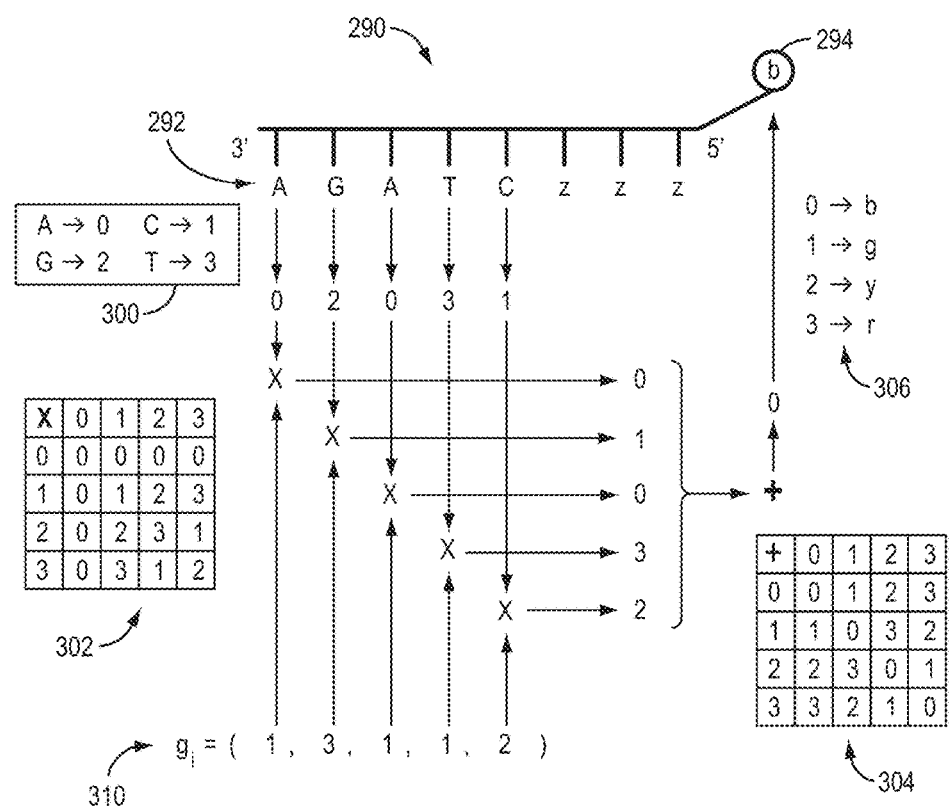
FIG. 15A is a representation of an embodiment of an interrogating probe that can be generated by an embodiment of the process of FIG. 14, where the probe can be configured to interrogate five nucleotides.
Figure 15B:
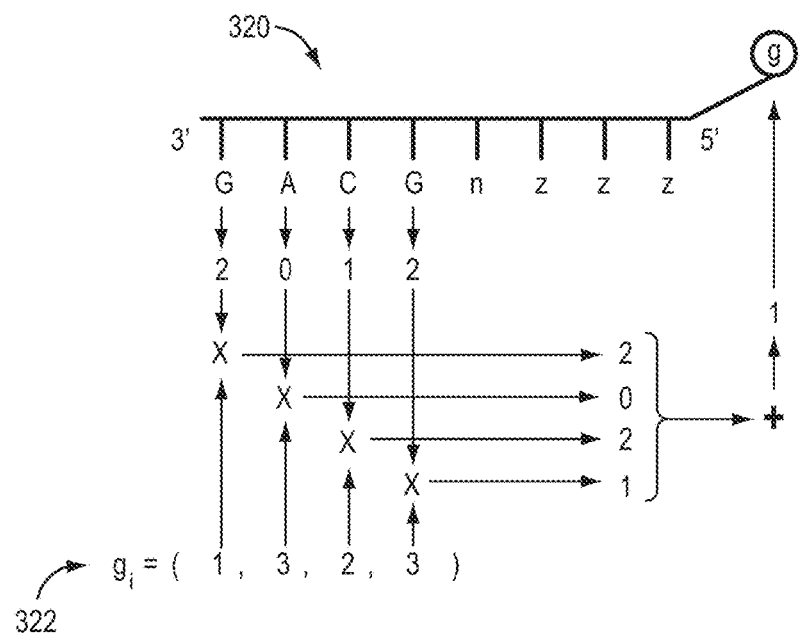
FIG. 15B is a representation of an embodiment of an interrogating probe where the probe can interrogate four nucleotides.
Figure 15C:
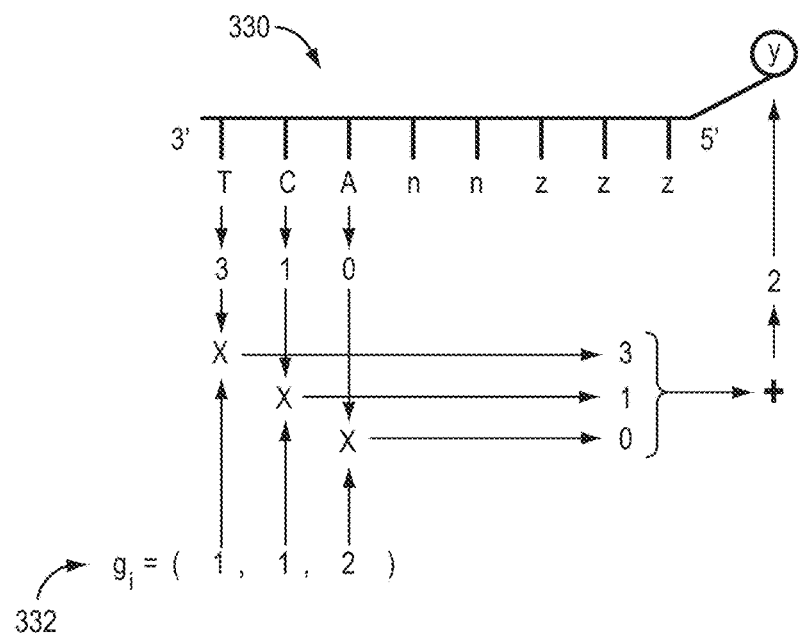
FIG. 15C is another representation of an embodiment of an interrogating probe where the probe can interrogate three nucleotides.

FIGS. 15A-15C show specific but non-limiting examples of dye assignments that can be achieved via the process 270 of FIG. 14. In FIG. 15A, a dye assignment configuration is shown for a probe 290 having 5-symbols of nucleotides 292. For the purpose of description, the probe 290 is depicted as having a 3' end and a 5' end, with a dye 294 disposed on the 5' end. Further, the probe 290 is depicted as being an octamer with the 5-symbols of nucleotides and three unused symbols of universal bases (depicted as "z"). Such a configuration allows use of the probe 290 in sequencing systems such as SOLiD. It will be understood, however, that various features such as 3' and 5' ends, particular position of the dye, octamer, and/or use of universal bases are not necessarily requirements for the purpose of encoding selection.

In FIG. 15A, an example 5-symbol sequence of AGATC is shown to be transformed to numerical representation 02031 based on map 300, where A is represented by 0, C by 1, G by 2, and T by 3. The 5-symbol numerical representation of the 5-symbol sequence is shown to be multiplied with a selected generator vector 310. The generator vector 310 is shown as $g_i=(1, 3, 1, 1, 2)$. Selection of such generator vectors is described herein in greater detail.

In certain embodiments, the multiplication of the 5-symbol numerical representation 02031 and the generator vector 13112 can be performed based on a rule such as a Galois field GF(4) multiplication table 302. Thus, multiplication of the first symbols (0 and 1) yields 0, multiplication of the second symbol (2 and 3) yields 1, and so on, so as to yield a product 01032.

In certain embodiments, members of the product 01032 can be summed based on a rule such as a Galois field GF(4) addition table 304. Thus, addition of symbols 1 and 2 (0 and 1) yields a sum of 1, and addition of that sum with symbol 3 (0) yields a sum of 1. Continuing, addition of 1 with symbol 4 (3) yields a sum of 2, and addition of 2 with symbol 5 (2) yields a sum of 0. Thus, the sum of the product 01032 is shown to be 0.

In certain embodiments, the resulting sum can be assigned to one of the four dye types. In the example shown in FIG. 15A, the four dye types are shown as four colors blue ("b"), green ("g"), yellow ("y"), and red ("r"). Thus, based on a color assignment map 306 (0 assigned to b, 1 to g, 2 to y, and 3 to r), the sum 0 is shown to result in a blue dye (294) being assigned to the probe having a sequence of AGATC.

FIG. 15B shows a similar dye color assignment scheme for a probe 320 having a 4-symbol sequence GACG based on an example generator vector 322. Base-to-number map, multiplication rule, summation rule, and number-to-color map can be similar to that described in reference to FIG. 15A.

In FIG. 15B, the fifth symbol is unused for the purpose of color assignment to the 4-symbol sequence; and is shown to be occupied by a degenerate base (depicted as "n"). Introduction of such a base into a probe such as the example octamer probe of FIG. 15B is generally known in the art.

In FIG. 15B, the example 4-symbol sequence GACG yields a summation value of 1. Thus based on the color assignment table (306 in FIG. 15A), a green dye is assigned to the probe 320.

FIG. 15C shows a similar dye color assignment scheme for a probe 330 having a 3-symbol sequence TCA based on an example generator vector 332. Base-to-number map, multiplication rule, summation rule, and number-to-color map can be similar to that described in reference to FIG. 15A. The example 3-symbol sequence TCA yields a summation value of 2; thus, a yellow dye is assigned to the probe 330.

In FIGS. 15A-15C, example generator vectors $g_i=(1, 3, 1, 1, 2)$, $g_i=(1, 3, 2, 3)$, and $g_i=(1, 1, 2)$ are used to multiply the numerical representations of 5-symbol, 4-symbol, and 3-symbol probe sequences. In certain embodiments, such generator vectors can be selected based on one or more factors that contribute to the robustness of the resulting encoding. For example, Hamming distance is a parameter that represents a distribution of encoded codes. If the encoding process results in the codes being "crowded" together (small Hamming distance), then decoding of such codes may be more susceptible to additional errors. Thus, having a relatively large Hamming distance among the codes can be beneficial.

Figure 16:
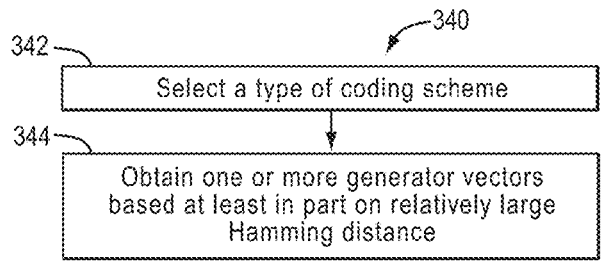
FIG. 16 is a flow-chart which shows an embodiment of a process that can be implemented to generate unique dye assignment schemes such as those shown by examples in FIGS. 15A-15C.

FIG. 16 shows a process 340 that can be implemented to select one or more generator vectors. In a process block 342, a type of coding scheme can be selected. Examples of such coding schemes are described herein in greater detail. In a process block 344, one or more generator vectors can be obtained based at least in part on relatively large Hamming distance among the codes generated by the generator vector(s).

In certain embodiments, performance of encoding operation and/or redundancy-introducing operation may not be readily apparent while selecting the generator vector(s). Thus, as shown in FIG. 17, a feedback system 350 can be implemented to facilitate evaluation of one or more performance parameters associated with, for example, generator vector(s).

In certain embodiments, the feedback system 350 can include a base sequence generator 352 configured to generate a sequence of bases to be measured. Such a sequence can be provided to an encoder 354 configured to generate codes having redundancy. Such encoding can include, for example, dye color assignments based on given generator vector(s) and/or redundancy-introductions.

Codes resulting from the encoder 354 can be provided to a modeling component 356. Such a component can be configured to simulate, for example, signal detection and processing, and dye color determination. Such simulated measurements can be provided to a decoder 358 where the measured colors can be decoded.

Figure 17:
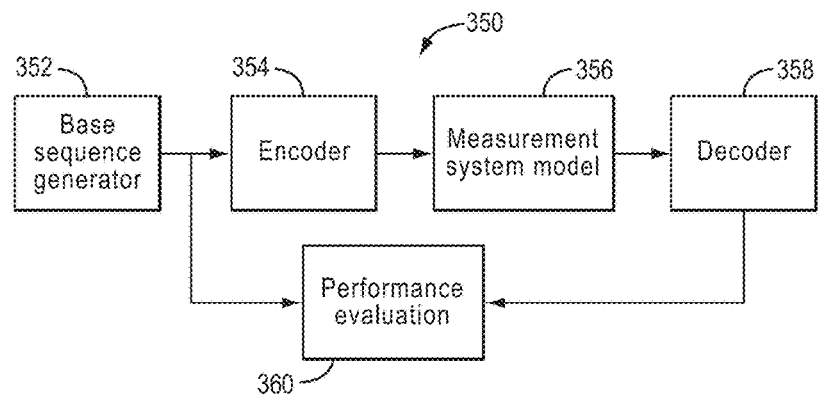
FIG. 17 is a block diagram of an embodiment of a system where performance of redundancy encoding can be implemented and evaluated.

As shown in FIG. 17, the decoded output data can be compared to the input data (from the base sequence generator 352) by a performance evaluation component 360. Such a component can evaluate how accurately the input data was preserved in the output. If any error is detected by the comparison, the performance evaluation component 360 can also evaluate how well such errors can be corrected.

Figure 18:
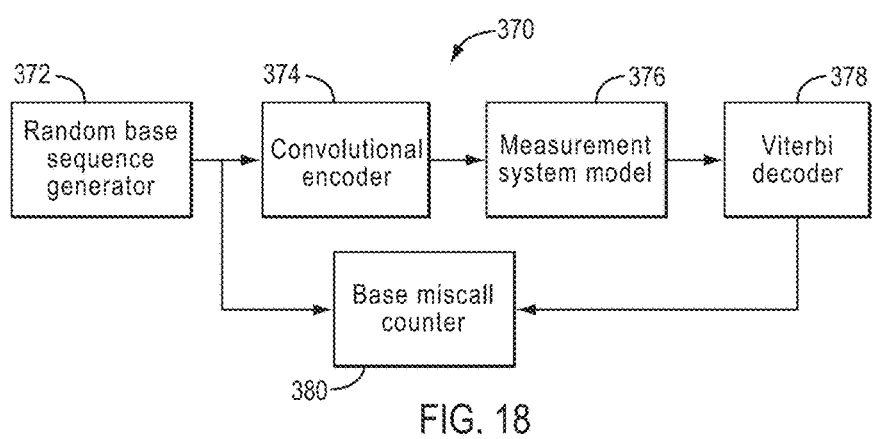
FIG. 18 is a block diagram of an embodiment of a system where performance of redundancy encoding can be implemented and evaluated.

FIG. 18 shows a more specific example configuration 370 of the feedback system 350 of FIG. 17. For example, the base sequence generator 352 of the system 350 can be a random or pseudo-random base sequence generator 372. In another example, the encoder 354 can be a convolutional encoder 376 known in the art; and the decoder 358 can be a Viterbi decoder known in the art. In yet another example, the performance evaluation component 360 can be a base mis-call counter 380.

As is known, convolutional code is a type of a linear coding scheme where mapping occurs for sliding windows of symbols. In the context of coding a sequence of bases, such a sliding window can be a K-symbol sequence in a template strand. For convolutional coding (and assuming a situation where four dye colors are being used), two generator vectors $g_1$ and $g_2$ and the resulting groups of probes can facilitate sufficient number of unique measurements to introduce redundancy. As described herein, one group of probes (having one of four colors) can provide S (e.g., 5) unique measurements via S offsets; and one or more additional unique measurements can be provided by a second group of probes (up to another S unique measurements).

As is also known, limiting the search for desirable generator vectors to two ($g_1$ and $g_2$) generally limits the number of unique codes to relatively small numbers. In the context of the Galois field GF(4) configuration (FIGS. 15A-15C), there are 256 unique 256 3-symbol generator vectors, 4,096 4-symbol generator vectors, and 65,536 5-symbol generator vectors.

Based on the foregoing, two generator vectors $g_1$ and $g_2$ having desirable performance attributes can be identified. As described in reference to FIG. 16, Hamming distance is a factor that can be important. However, other factors can be considered, since a number of generator vectors can yield similar large Hamming distances.

Table 1 lists example generator vectors that have been identified as providing desirable performance attributes (such as large Hamming distance) for different example measurement configurations:

TABLE 1

| Number of symbols (K) | Number of measurements | $g_1$ | $g_2$ | Hamming distance |
| --- | --- | --- | --- | --- |
| 3 | 6 | (1, 2, 1) | (1, 3, 1) | 3 |
| 4 | 6 | (1, 1, 1, 2) | (1, 2, 0, 1) | 4 |
| 5 | 6 | (1, 1, 2, 2, 1) | (1, 2, 0, 0, 1) | 4 |
| 5 | 7 | (1, 2, 3, 2, 1) | (1, 0, 3, 3, 3) | 5 |

As listed in Table 1, and in the context of 5-symbol configuration, performing seven rounds of measurements can increase the resulting Hamming distance (5) from the six-round case (Hamming distance=4). As described herein, Hamming distance can be an important factor, but not necessarily the only factor to be considered overall. For example, if the additional round (seventh round) is costly and time consuming, the increased Hamming distance provided by the extra round may not be beneficial.

For the example measurement configurations listed in Table 1, the coded probes have offset capacity of five symbols. Thus, five unique measurements can be achieved using one of the two generator vectors $g_1$ and $g_2$. To provide redundancy (when using one dye per probe and four colors), one or more additional unique measurements can be made using the other generator vector. For example, and as described in reference to FIG. 11, the other generator vector can be used for one additional measurement. In a preferred embodiment, when selecting such distinct probe sets to be used together, the sets can be configured relative to one another to provide optimized results (e.g., accuracy). That is, the sets are preferably not devised in isolation but rather in view of one another such that the multiple interrogations of the data by the distinct probe sets can minimize ambiguity during decoding of the data.

Probe sets can also be carefully and specifically constructed so as to optimize the particular data encoding process for which the presently disclosed systems and methods are utilized. For example, specific probe sets are disclosed herein which are optimized for use with ligation-based DNA sequencing, in particular, for use with the SOLiD DNA sequencing system. While the following discussion will focus on such systems, those skilled in the art will appreciate that the presently disclosed teachings can be applied to optimize probe selection and encoding schemes for various other types of DNA sequencing systems (e.g., other ligation-based systems, polymerase-based systems, etc.).

Figure 19A:
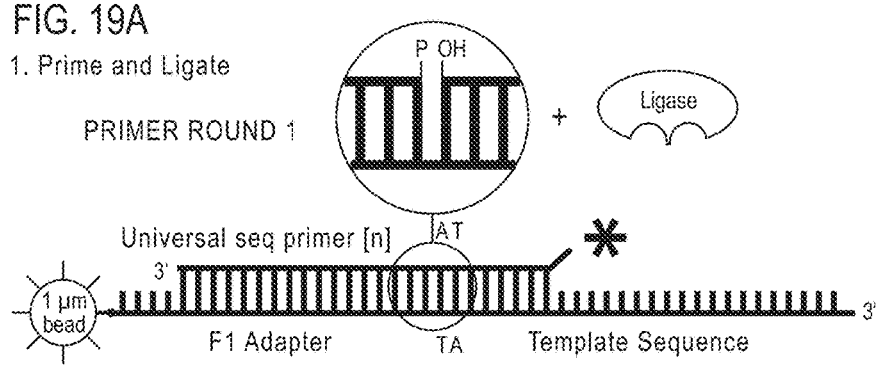
FIGS. 19A-19G is an embodiment of a ligation-based DNA sequencing process.
Figure 19B:
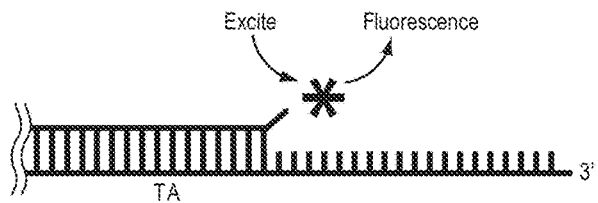
Figure 19C:
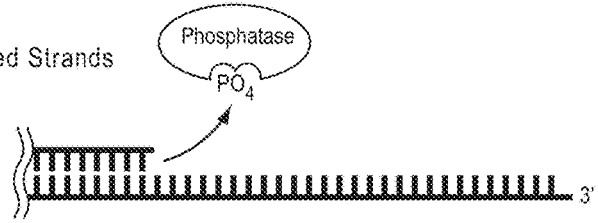
Figure 19D:
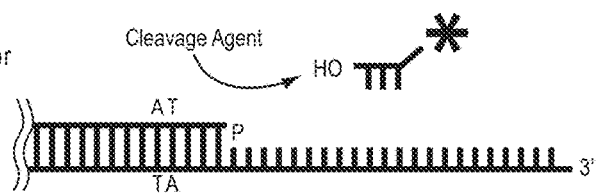

FIGS. 19A-19G provides a general overview of an embodiment of ligation-based sequencing chemistry utilized with the SOLiD system. FIG. 19A shows Primer Round 1 which includes initialization using a first initializing oligonucleotide that is hybridized to an adapter sequence (referred to above as a binding region) in the template to provide an extendable duplex. As detailed below, in some embodiments the last base of the adaptor sequence is a known value thereby providing a starting point for later base determination which takes place after all ligation cycles and rounds are complete. FIG. 19B shows excitation of the tags (e.g., fluorophores) thereby producing signal (e.g., colors) to be detected by the optical system. FIG. 19C shows a step wherein those strands which did not participate in Primer Round 1 are "capped" thereby preventing them from participating in future ligation cycles. FIG. 19D shows a cleavage step where the tag is removed thereby preparing the strand for future ligation rounds.

Figure 19E:
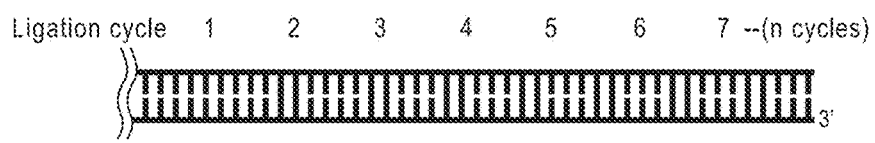
Figure 19F:
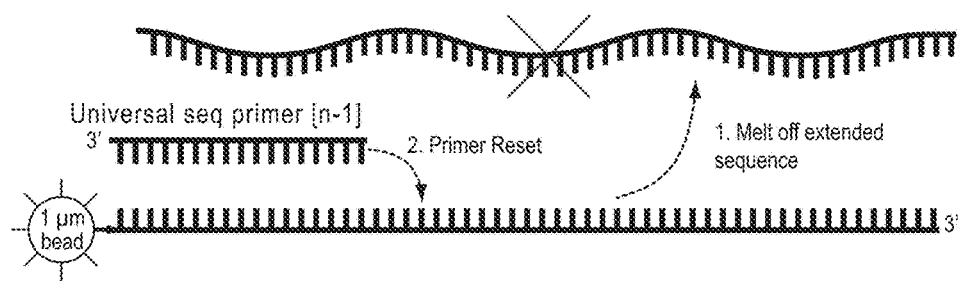
Figure 19G:
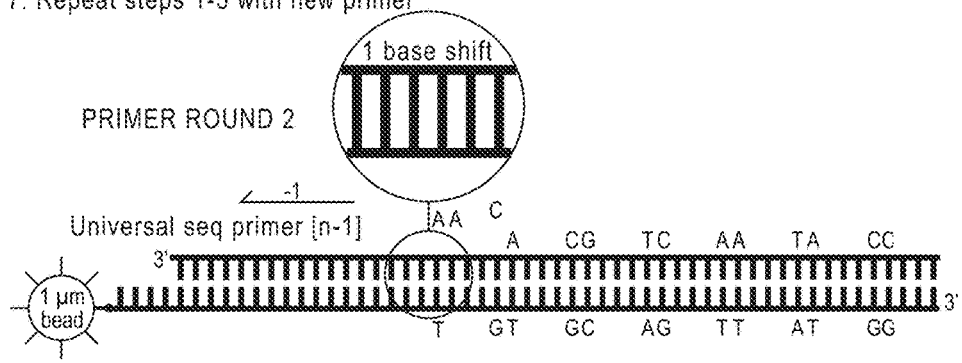

FIG. 19E shows several ligation cycles of nucleotide identification in which every various nucleotides are interrogated in order to generate signal(s). Following a desired number of cycles, the extended strand, including the first initializing oligonucleotide, is removed and a second oligonucleotide that binds to a different portion of the binding region from that at which the first initializing oligonucleotide bound, is hybridized to the template. FIG. 19F shows a second sequencing reaction, the Primer Reset, in which initialization is performed with a second initializing oligonucleotide, followed by several cycles of nucleotide interrogation. FIG. 19G then shows extension from the second initializing oligonucleotide allows interrogation of nucleotides in a different "frame" from the nucleotides interrogated in the first sequencing reaction.

As summarized above, the SOLID system enables massively parallel sequencing of clonally amplified DNA fragments linked to beads. As shown, this sequencing methodology is based on sequential ligation oligonucleotide probes labeled with one of four fluorescent dyes, Whereby each probe can assay up to 5 base positions as a time. Every window of five consecutive bases of DNA fragment is interrogated at least once (as controlled via probe cleaving, primer hybridization, and primer resets), and some windows are interrogated twice. In the later case, the first and second inspections are performed using differently labeled probe sets, carefully designed to form a redundant error correcting code. The set of all dye color measurements, each carrying information about multiple bases, is then used by specialized decoding algorithms to establish the most likely base sequence (before and after mapping), even in the presence of measurement errors.

As such, in some embodiments, the above-described ligation rounds are performed with distinct sets of probes. That is, an initial series of ligation rounds are performed offset from another. Further, these ligation rounds can be performed with specifically constructed probes such that each nucleotide is interrogated at least twice. In a preferred embodiment, the initial ligation rounds utilize di-base specific probes. That is, the probes are specific for 2 adjacent nucleotides. Thus, during the initial series of offset ligation rounds, each nucleotide will be interrogated twice: first, as the first nucleotide of a pair, and second, as the second nucleotide of a pair. These interrogations will provide two signals. The first signal generated by the first interrogation event and the second signal generated by the second interrogation event. Each of these two signals is required to determine the identity of a single base. That is, when considering 3 consecutive nucleotides, the identity of the middle nucleotide can only be determined by evaluating the first signal generated when nucleotides 1 and 2 are interrogated in view of the second signal generated when nucleotides 2 and 3 are interrogated.

The system can also employ at least one additional round of ligation which interrogates the same data as was interrogated during the initial ligation rounds. However, this additional ligation round can utilize probes of a distinct probe set thereby providing two signals for the same data thereby providing redundant encoded data.

FIG. 20A-FIG. 20C provides three examples of di-base specific probes capable of being used in the above-described DNA ligation-based sequencing. These encoding schemes, similar to the 5-base probes discussed above, are generated by use of distinct generator vectors in addition to Galois field GF(4) look-up table 307, multiplication table 309, and summation table 311. That is, FIG. 20A provides a first 2-base encoding scheme 301 utilizing generator vector G=(1 1), and the Color=Base1+Base2. FIG. 20B provides another embodiment of a 2-base encoding scheme 303 where the generator vector is represented as G=(1 2) and the Color=Base1+2×Base2. FIG. 20C provides yet another embodiment of a 2-base encoding scheme 305 where the generator vector is represented as G=(1 3) and the Color=Base1+3×Base 2. For each, "0" represents Blue, "1" represents Green, "2" represents Yellow, and "3" represents Red. Those skilled in the art will appreciate that various other such schemes are within the spirit and scope of the present disclosure.

Figure 21:
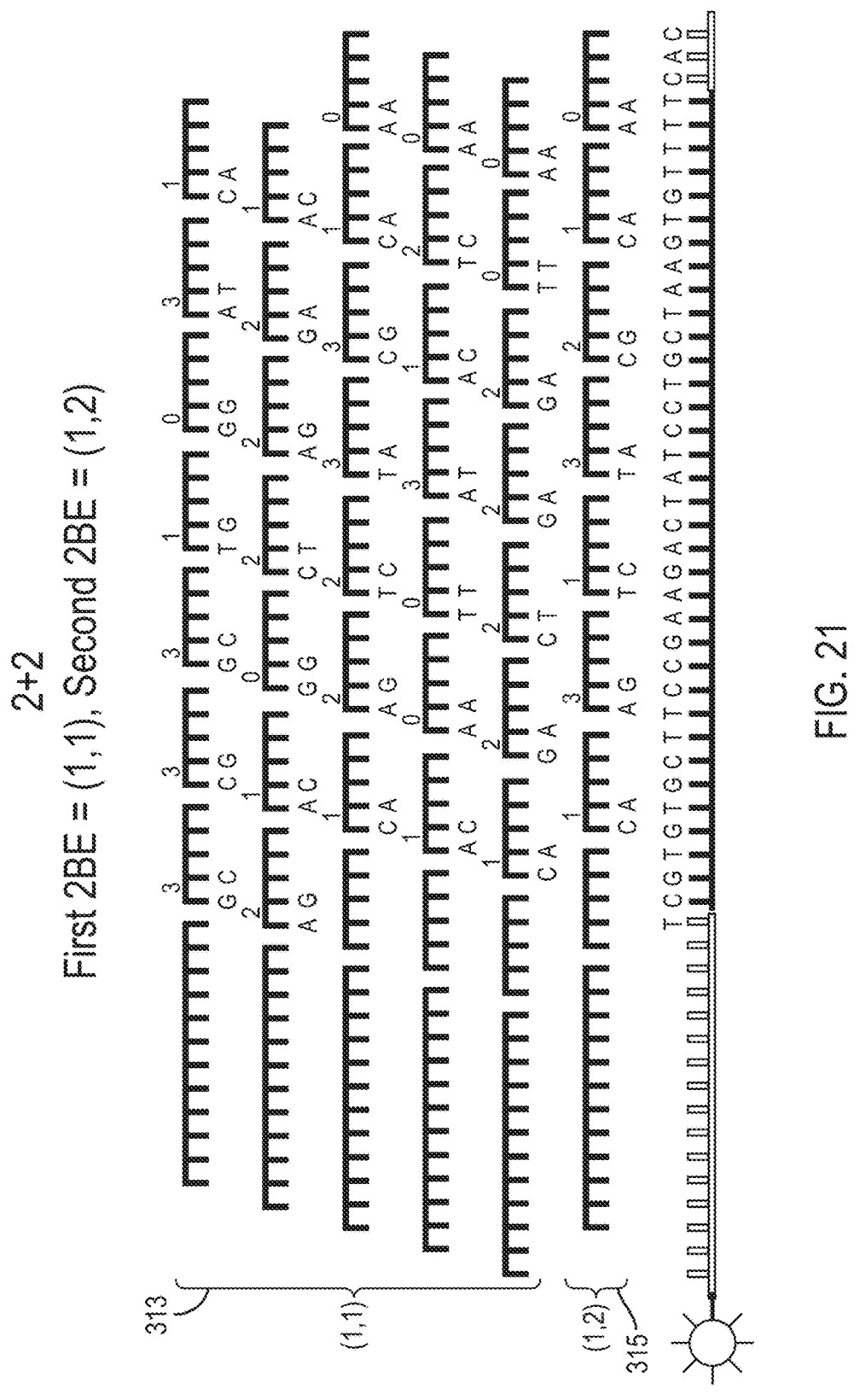

FIG. 21 provides an example of ligation-based DNA sequencing utilizing the probe sets prepared in accordance with FIG. 20A and FIG. 20B. That is, as shown, the first 5 ligation rounds, designated as 313, are performed with probe set 1 which includes di-base specific probes prepared in accordance with the teaching of FIG. 20A (probe set identified as (1, 1) in accordance with the generator vector). Note that each of these rounds is performed at a 1-base offset relative to a following round such that each base is interrogated twice. In reviewing FIG. 21 (as well as FIGS. 22 and 24), note that symbol "0" corresponds to Blue, symbol "1" corresponds to Green, symbol "2" corresponds to Yellow, and symbol "3" corresponding to Red.

A $6^{th}$ ligation round, designated as 315, is performed with probes of probe set 2 which includes probes prepared in accordance with the teachings of FIG. 20B (probe set 2 identified as (1, 2)). Note that this second probe set provides a second interrogation of nucleotides which have already been interrogated by the first probe set. However, making reference to FIGS. 20A and 20B, probe set 2 will give a different signal (e.g., color) for the same interrogation event as compared to probe set 1. In a preferred embodiment, probe set 1 and probe set 2 are selected in view of one another so as to provide optimized system accuracy.

Figure 22:
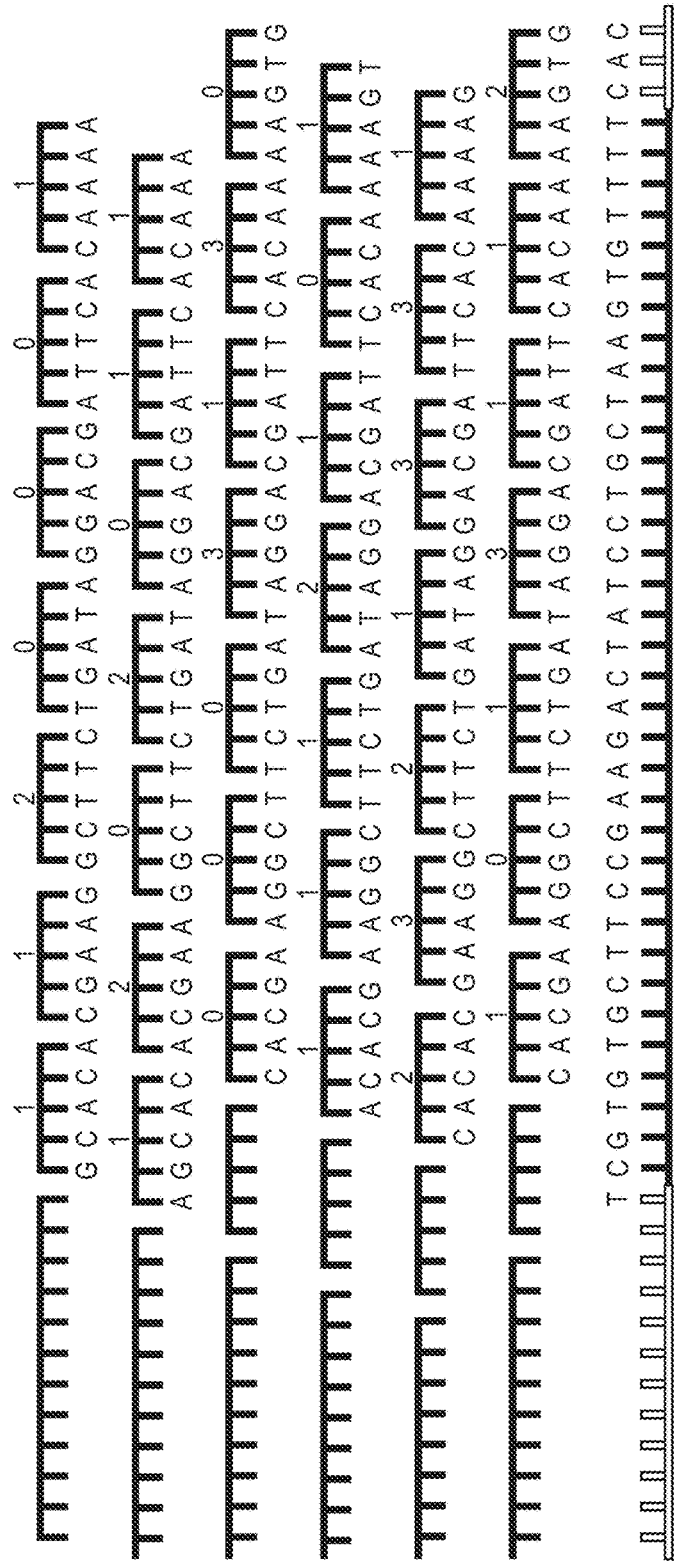
FIG. 22 is another representation of multiple rounds of ligation-based sequencing being performed with distinct probe sets, and includes SEQ ID NO: 3 (first row), SEQ ID NO: 4 (second row), SEQ ID NO: 5 (third and sixth rows), SEQ ID NO: 6 (fourth row), SEQ ID NO: 7 (fifth row), and SEQ ID NO: 2 (seventh row)

FIG. 22 provides another example which illustrates that various combinations of first and second probe sets are within the spirit and scope of the present disclosure. That is, FIG. 22 provides an example where ligation rounds 1-5 are performed with a 5-base specific probe, and ligation round 6 is performed with a distinct set of 5-base specific probes. In accordance with the teachings of FIG. 15A, such distinct 5-base specific probes can be prepared by careful selection and optimization of generator vectors. Those skilled in the art will appreciate that any such combination of distinct probe sets, use of more than two distinct probe sets, etc. are within the spirit and scope of the present disclosure.

Figure 23:
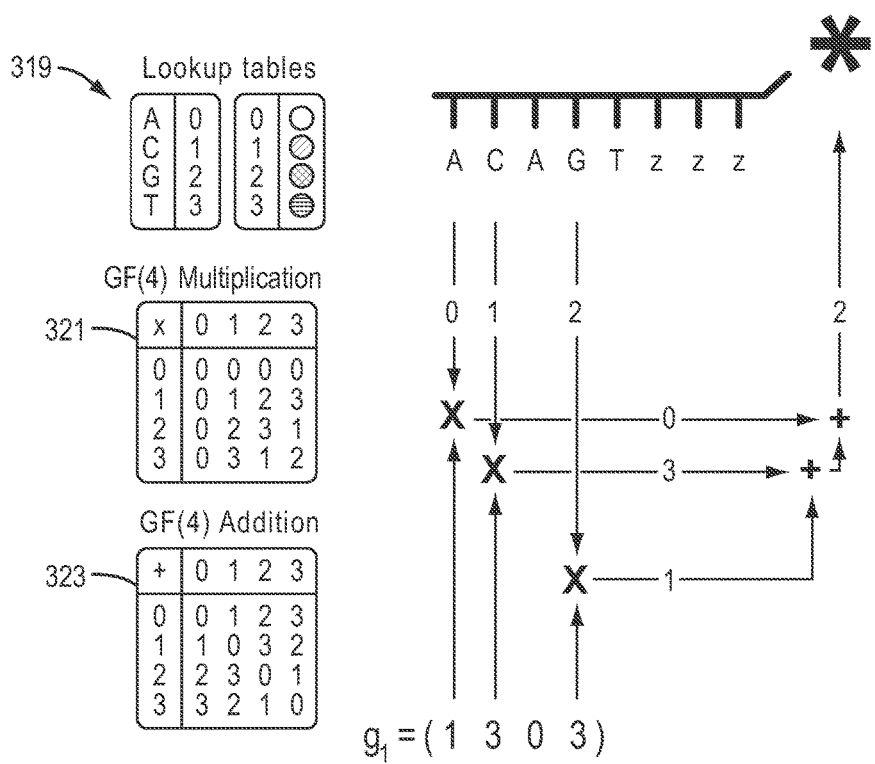
FIG. 23 is another example of an interrogating probe configured to interrogate four nucleotides.

In a preferred embodiment, the presently disclosed system can be employed during DNA sequencing utilizing 5 offset ligation rounds with the di-base specific probe prepared in accordance with the teachings of FIG. 20A (probe set (1, 1)) and a $6^{th}$ ligation round utilizing a 4-base specific probe set. FIG. 23 provides a preferred embodiment of such a 4-base specific probe. Like above, various generator vectors can be utilized in this embodiment. In a preferred embodiment, the generator vector is G=(1 3 0 3) which is utilized with Galois field GF(4) look-up table 319, multiplication table 321, and summation table 323. As shown, the probe sequence of ACAGT can correspond to a value of 2 which corresponds to a specific tag or color. Note that probe set (1, 3, 0, 3) has a special property that the color does not depend on base position 3 because of the 0 at the position 3

Figure 24:
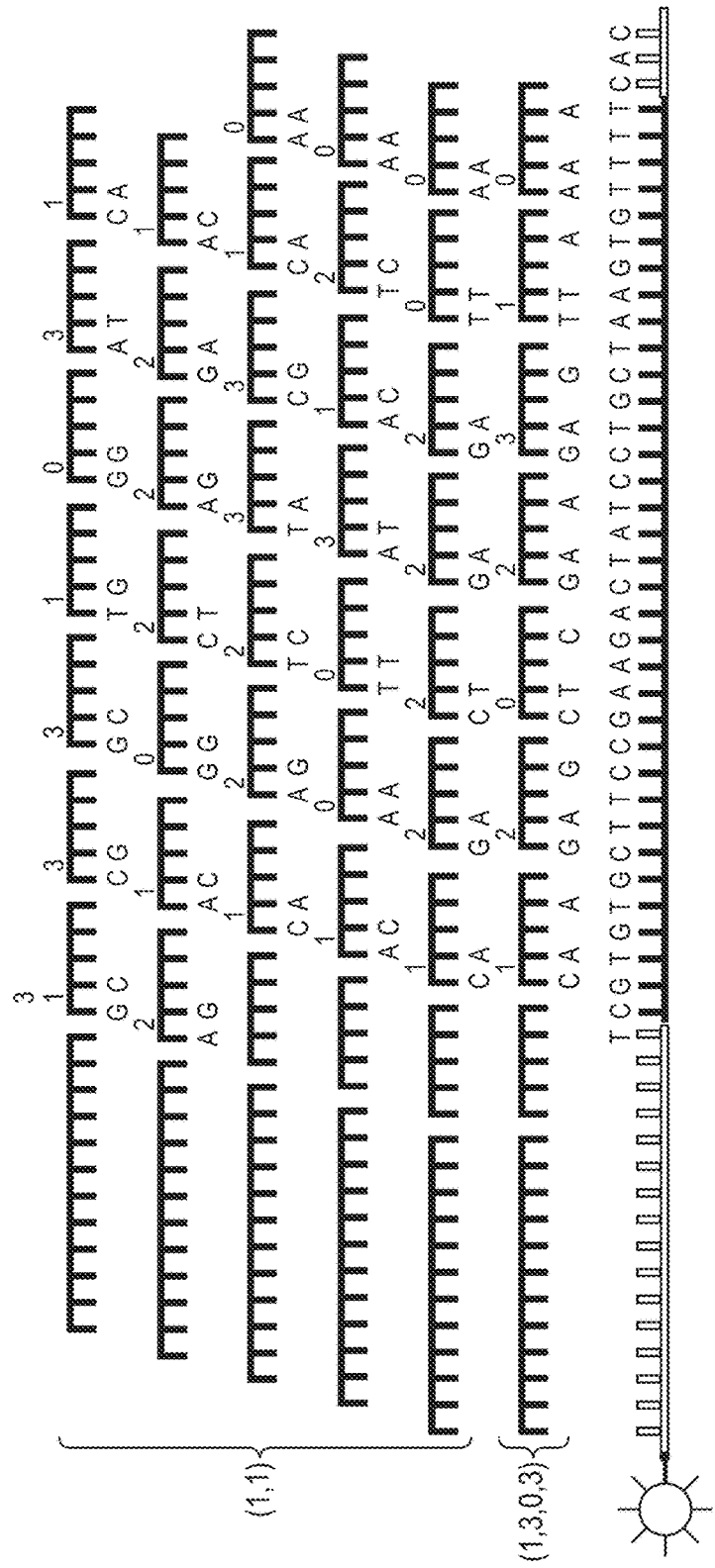
FIG. 24 is a representation of a preferred embodiment of ligation-based sequencing utilizing a di-base specific probe and a 4-base specific probe, and includes SEQ ID NO: 2.

FIG. 24 provides a representation of this preferred embodiment utilizing probe set 1=(1, 1) and probe set 2=(1, 3, 0, 3). This encoding scheme can be referred to as ("2+4" encoding). Table 2 provides the preferred labeling scheme for 2+4 encoding:

|  | Sequences detected by labeled probes (Note 1: the probes themselves have reverse-complementary sequences) (Note 2: Star denotes any base) | | | |
|---|---|---|---|---|
| Probe label | FAM (0) | Cy3 (1) | TXR (2) | Cy5 (3) |
| Probe set 1 | AA*** | AC*** | AG*** | AT*** |
|  | CC*** | CA*** | GA*** | TA*** |
|  | GG*** | GT*** | CT*** | CG*** |
|  | TT*** | TG*** | TC*** | GC*** |
| Probe set 2 | AA*C* | AA*T* | AA*G* | AA*A* |
|  | AC*A* | AC*G* | AC*T* | AC*C* |
|  | AG*T* | AG*C* | AG*A* | AG*G* |
|  | AT*G* | AT*A* | AT*C* | AT*T* |
|  | CA*T* | CA*C* | CA*A* | CA*G* |
|  | CC*G* | CC*A* | CC*C* | CC*T* |
|  | CG*C* | CG*T* | CG*G* | CG*A* |
|  | CT*A* | CT*G* | CT*T* | CT*C* |
|  | GA*G* | GA*A* | GA*C* | GA*T* |
|  | GC*T* | GC*C* | GC*A* | GC*G* |
|  | GG*A* | GG*G* | GG*T* | GG*C* |
|  | GT*C* | GT*T* | GT*G* | GT*A* |
|  | TA*A* | TA*G* | TA*T* | TA*C* |
|  | TC*C* | TC*T* | TC*G* | TC*A* |
|  | TG*G* | TG*A* | TG*C* | TG*T* |
|  | TT*T* | TT*C* | TT*A* | TT*G* |

Figure 25:
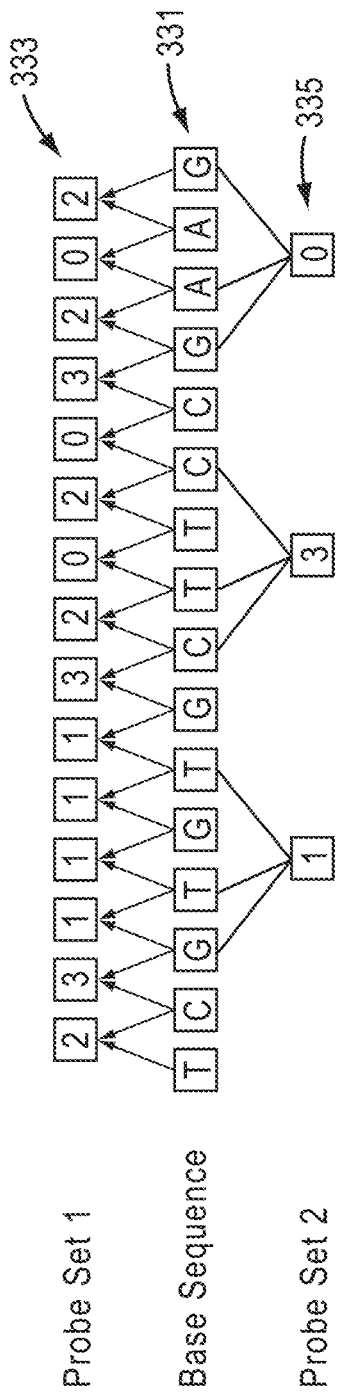
FIG. 25 is a representation of redundancy incorporated into the encoded data resulting from the ligation steps depicted in FIG. 24, and includes SEQ ID NO: 8.

FIG. 25 provides another depiction of redundancy introduced by the above-described 2+4 encoding scheme. That is, the Base Sequence 331 is provided with signals provided by the initial rounds of ligation 333 provided above the sequence, while the signal provided by the $6^{th}$ round of ligation 335 provided below the sequence. As shown, the initial offset ligation rounds provide signals 333 based on di-base readings; thus, the signal appears to fall between each nucleotide pair. That is, looking at the first two nucleotides of the sequence, T and C, a signal, depicted as 2 which could be considered to correspond with a color (e.g., Yellow). Redundancy is introduced because this signal is insufficient to identify either of the bases. Rather, the system requires the second and third nucleotides, C and G, to be interrogated by a second di-base probe which generates a second signal, shown as 3 (e.g., Red). In view of these two readings and the probe chart above, the system can determine the identity of the second nucleotide, C.

FIG. 25 also depicts the additional layer of redundancy and enhanced accuracy which is provided by interrogating data a second time with at least one distinct probe set so as to generate a second signal 335 which serves to introduce additional redundancy into the encoded data. That is, as shown below the Base Sequence 331, the second distinct probe set, in this case the (1, 3, 0, 3) 4-base specific probe set, an additional signal 335 is provided between, as shown herein, the $4^{th}$ and $5^{th}$ nucleotide, the $9^{th}$ and $10^{th}$ nucleotide, and the $14^{th}$ and $15^{th}$ nucleotide. More specifically, the present example shows that the second probe set provides additional signals 1, 3, 0, between the $4^{th}$ and $5^{th}$ nucleotides, $9^{th}$ and $10^{th}$ nucleotides, and the $14^{th}$ and $15^{th}$ nucleotides, respectively.

Figure 26:
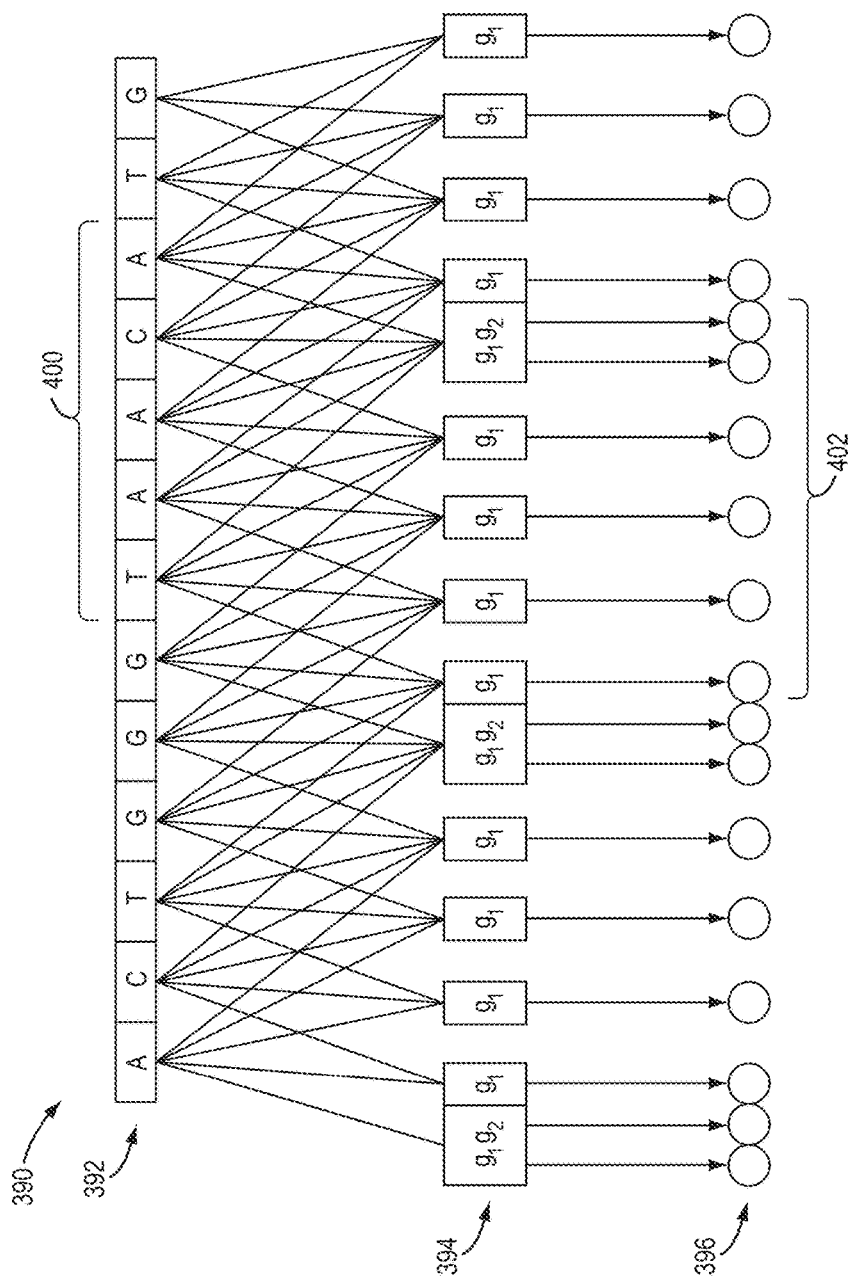
FIG. 26 is a representation of an example of a measurement that can include redundancy introduced to data via error-correcting code schemes such as convolutional codes and punctured convolutional codes, and includes SEQ ID NO: 9.

FIG. 26 depicts another embodiment of a coding configuration 390 similar to the example shown in FIG. 11. In FIG. 26, however, coding of a base sequence 392 is depicted as being mediated by the two generator vectors 394 (g1 and g2) so as to yield a code sequence 396. Thus, an example 5-symbol window 400 yielding a 6-symbol code 402 can be considered to be a punctured convolutional coding scheme.

Punctured convolutional coding can represent a situation where certain coded symbols resulting from a combination of two or more convolutional codings are unused. In the context of the example coding configuration 390 shown in FIG. 26, symbols that would correspond to rounds 1 to 4 with the generator vector $g_2$ (which would be overall rounds 7 to 10 if performed) can be viewed as being unused. Thus, of the possible 10 symbols of code in window 402, symbols at positions 2, 4, 6, and 8 can be considered to be "punctured."

Figure 27:
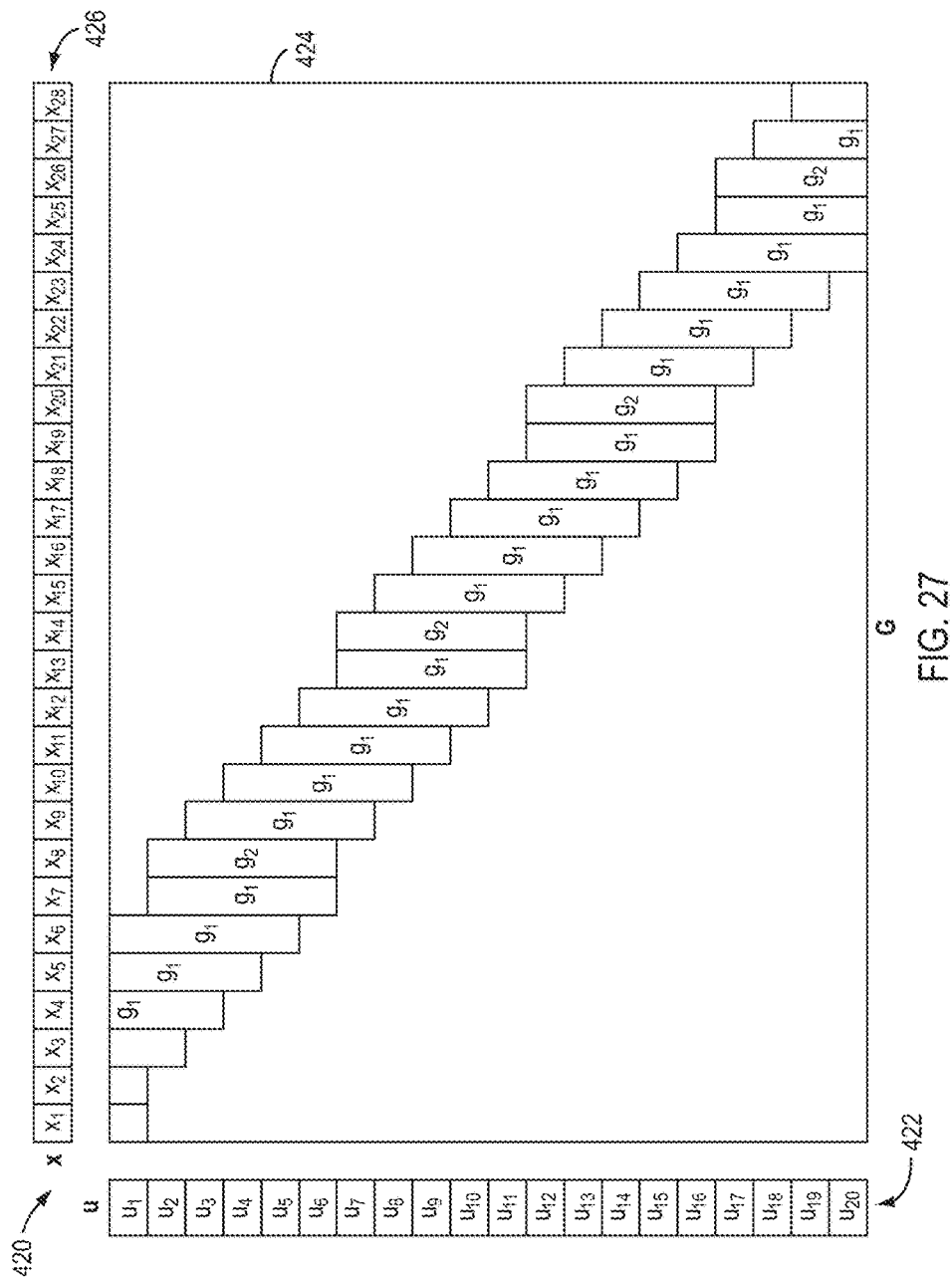
FIG. 27 is an example of how the punctured convolutional coding scheme of FIG. 26 can be implemented to introduce redundancy while measuring a lengthy sequence of nucleotides.

FIG. 27 shows another perspective 420 of the punctured convolutional coding scheme of FIG. 26. In certain situations, a sequence of nucleotides being analyzed can be considered to be an example of an information sequence u (422); and a codeword x (426) can result from coding of u. An encoding operation can be represented as x=uG, where G represents a generator matrix 424 that yields, for example, a rate 5/6 code. By implementing appropriate selection of generator vectors $g_1$ and $g_2$ as part of the generator matrix, encoding such as that shown in FIG. 27 can be performed by sequencing systems such as SOLiD System.

Figure 28:
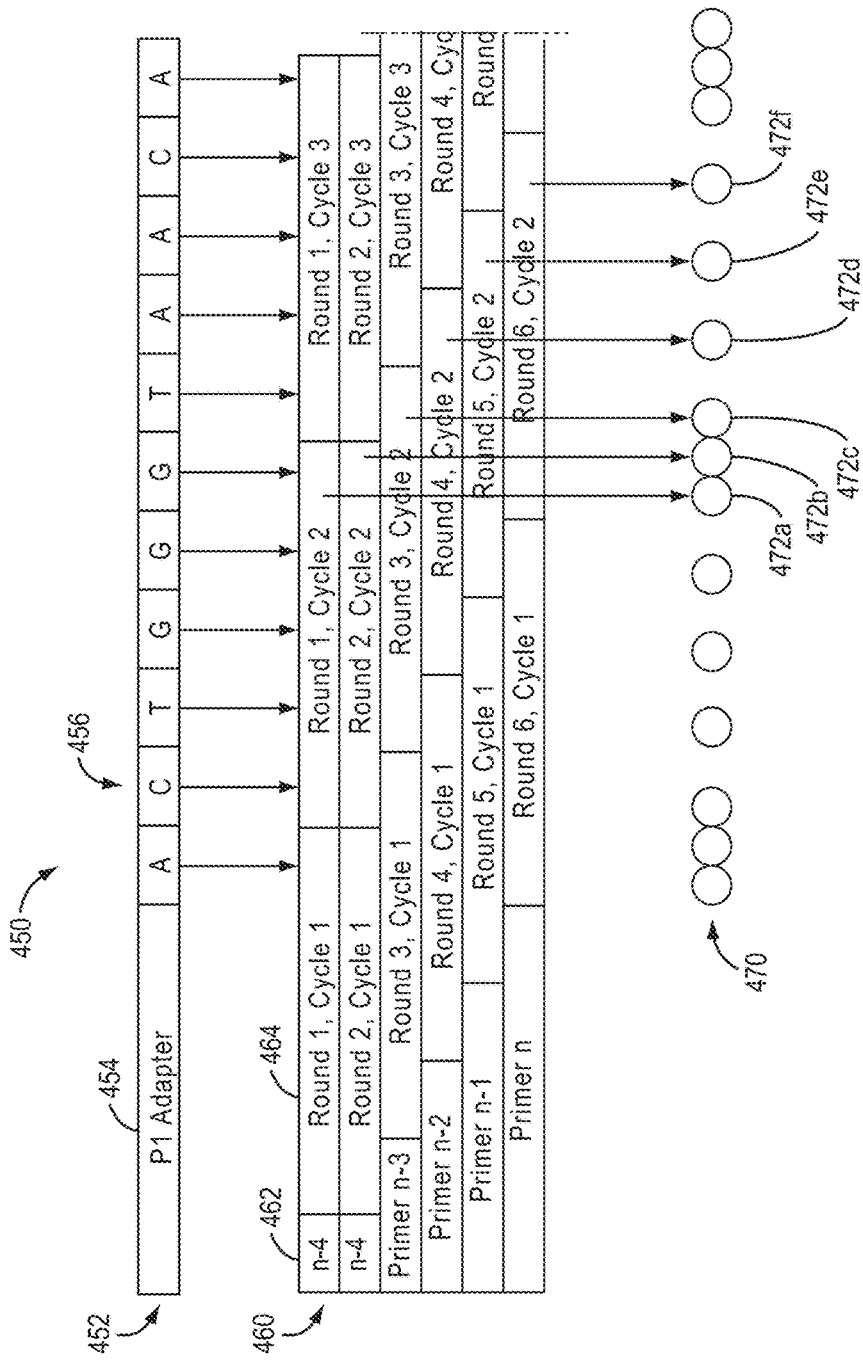
FIG. 28 is another representation of an embodiment of the presently disclosed encoding scheme being applied to a ligation-based sequencing process, and includes SEQ ID NO: 10.

FIG. 28 shows another example of a ligation-based sequencing operation. It will be understood that ligation based coverage of a template sequence can facilitate error correcting coding, but is not a requirement for the purpose of introducing redundancy. In the context of SOLiD System, a sequencing configuration 450 can include a template strand 452 having a base sequence 456 to be identified attached to a P1 adapter 454. Such a strand can be anchored to a substrate such as a bead (not shown).

In FIG. 28, the example rounds 460 of measurements are depicted as being facilitated by primer offsets 462 and two groups of probes. For the purpose of description of FIG. 28, five symbols of the ligation cycles are shown. It will be understood that one or more universal symbols (not shown) can be present in such probes.

Round 1 is shown to be performed at an offset value of n−4, where n=5, and the interrogation can be performed via one of the two groups of probes (e.g., $g_2$ generated probes). As shown, Round 1 can include a number of ligation cycles needed to cover the length of the template sequence 456.

As shown, Round 2 can be performed at the same offset value (n−4) as that for Round 1, and the interrogation can be performed via the other of the two groups of probes (e.g., $g_1$ generated probes). As shown, Round 2 can also include a number of ligation cycles needed to cover the length of the template sequence 456. In certain embodiments, Rounds 1 and 2 can be performed in a similar manner except the difference in probes used.

As shown, Round 3 can be performed at an offset value of n−3, and the interrogation can be performed via $g_1$ generated probes during a number of ligation cycles. Round 4 can be performed at an offset value of n−2, and the interrogation can be performed via $g_1$ generated probes during a number of ligation cycles. Round 5 can be performed at an offset value of n−1, and the interrogation can be performed via $g_1$ generated probes during a number of ligation cycles. Round 6 can be performed at an offset value of n, and the interrogation can be performed via $g_i$ generated probes during a number of ligation cycles.

As shown, ligation Cycle 2 of Round 1 yields a coded color depicted as 472*a*. Cycle 2 of Round 2 yields a coded color depicted as 472*b*. Continuing, Cycle 2 of Round 3 yields a code 472*c*, Cycle 2 of Round 4 yields a code 472*d*, Cycle 2 of Round 5 yields a code 472*e*, and Cycle 2 of Round 6 yields a code 472*f*. Such rounds and ligation cycles can yield a color sequence 470 having redundant information suitable for detection and correction of errors.

Referring back to FIG. 1A, the presently disclosed system further includes an ECC Decoder 14 configured to receive the above-described encoded data and decode such data while identifying and correcting errors without the need to repeat any measurements.

The ECC Decoder 14 can utilize any of a number or combination of algorithms capable of generating corrected data from the above-described encoding scheme. For example, the algorithm can be based on the BCJR Algorithm (Bahl, Cocke, Jelinek, Raviv, "Optimal decoding of linear codes for minimizing symbol error rate," IEEE Transactions on Information Theory, March 1974), the Viterbi Algorithm (Viterbi, "Error bounds for convolutional codes and an asymptotically optimum decoding algorithm," IEEE Transactions on Information Theory, April 1967), the Soft Output Viterbi Algorithm (A Viterbi algorithm with soft-decision outputs and its applications," Proceedings IEEE Conference on Global Communications (GLOBECOM 1989), November 1989), Sequential Algorithms, such as: ZJ-Algorithm, Fano Algorithm, M-Algorithm, T-Algorithm, A*-Algorithm (Anderson, Mohan, "Sequential coding algorithms: a survey and cost analysis," IEEE Transactions on Information Theory, February 1984), and Soft Output Sequential Algorithms, such as: LISS, BEAST, M*-BCJR, the entirety of each of these references being incorporated herein by reference thereto. Those skilled in the art will appreciate that various other such algorithms or combinations of algorithms are within the spirit and scope of the present disclosure.

Figures 29, 30:
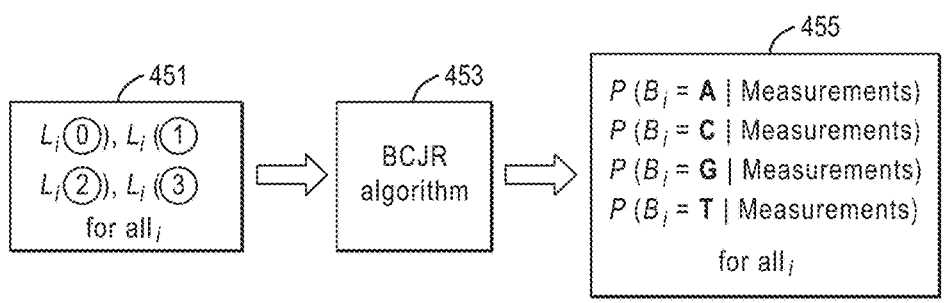
FIG. 29 is a representation of a potential output of an embodiment of the presently disclosed system.
FIG. 30 is a representation of an embodiment of encoded data being inputted into an algorithm, and the resulting output.

In a preferred embodiment, the system utilizes the BCJR algorithm. The BCJR algorithm, as depicted in FIG. 29, provides Bayesian inference of base probabilities. Bayesian inference is a method of statistical inference in which some kind of evidence or observations are used to calculate the probability that a hypothesis may be true, or else to update its previously-calculated probability. The term "Bayesian" comes from its use of the Bayes' theorem in the calculation process In practical usage, "Bayesian inference" refers to the use of a prior probability over hypotheses to determine the likelihood of a particular hypothesis given some observed evidence; that is, the likelihood that a particular hypothesis is true given some observed evidence (the so-called posterior probability of the hypothesis) comes from a combination of the inherent likelihood (or prior probability) of the hypothesis and the compatibility of the observed evidence with the hypothesis (or likelihood of the evidence, in a technical sense). Bayesian inference is opposed to frequentist inference, which makes use only of the likelihood of the evidence (in the technical sense), discounting the prior probability of the hypothesis.

Referring again to FIG. 29, the BCJR algorithm seeks to determine 4 probabilities at each base position. That is, the algorithm is configured to determine the probability that the base at position i is A, the probability that the base at position i is C, the probability that the base at position i is G, and the probability that the base at position i is T. This determination is made at each base position. As detailed below, redundancy introduced into the encoded color data allows for the probability determination to take into account various readings, Thus, each result is based on multiple signals or measurements.

FIG. 30 provides another representation of the function of the BCJR algorithm, That is, the BCJR algorithm 453 is configured to receive color likelihoods 451 for all base positions (i.e., all i positions), and convert such likelihoods into base probabilities 455 for all base positions. As described above, due to the intricacies involved with encoding data, such as for example, in the context of DNA sequencing, exact signal determinations (e.g., color calls) may not be possible but rather the system may provide a series of signal likelihoods indicative of the actual signal. As detailed below, the algorithm can be configured to efficiently solve this problem by utilizing previous measurements as well as breaking the problem into easier, more manageable problems.

Figure 31:
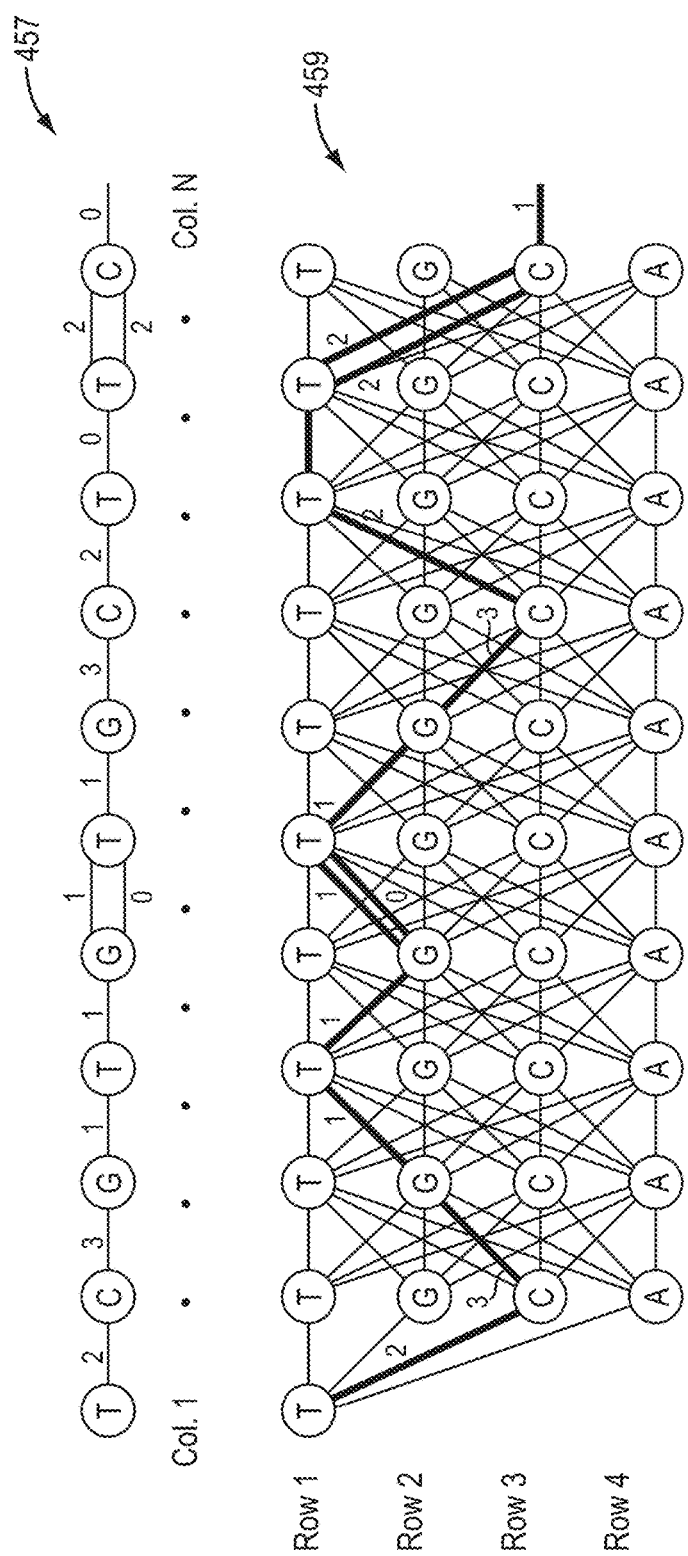
FIG. 31 is a representation of an embodiment of data processing by an algorithm of the presently disclosed system, and includes SEQ ID NO: 11.

In the context of DNA sequencing, referring to FIG. 31, the BCJR algorithm can be thought of as establishing a grid 459 having 4 rows with each row corresponding to each possible base (T, G, C, A), and having N columns corresponding to the encoded data points (e.g., the number of color likelihood signals to be evaluated). The algorithm can then be considered to work through the grid 459 by evaluating each possible path in an effort to maximize the probability of each path based on the color likelihood data determined above. That is, the true base sequence of T-C-G-T- . . . 457 is shown above the grid wherein each base is connected by the most likely color. That is, yellow (designated as "2") was determined to be the most likely color derived between the initial 2 nucleotides, T and C.

In reviewing FIGS. 31-37B, please note that the signals are depicted as numbers but could be considered colors. For example, "0" corresponds to Blue, "1" corresponds to Green, "2" corresponds to Yellow, and "3" corresponding to Red. Also note, as depicted in FIG. 31, the double-band positioned between the $5^{th}$ and $6^{th}$ nucleotides represents a double interrogation event wherein the first band corresponds to a first signal generated by probes of a first probe set (e.g., a di-base specific probe) and the second band corresponds to a second signal generated by probes of a second probe set (e.g., a 4-base specific probe). At this step, the BCJR algorithm considers the probability of both signals when maximizing probability across the grid.

Figure 32:
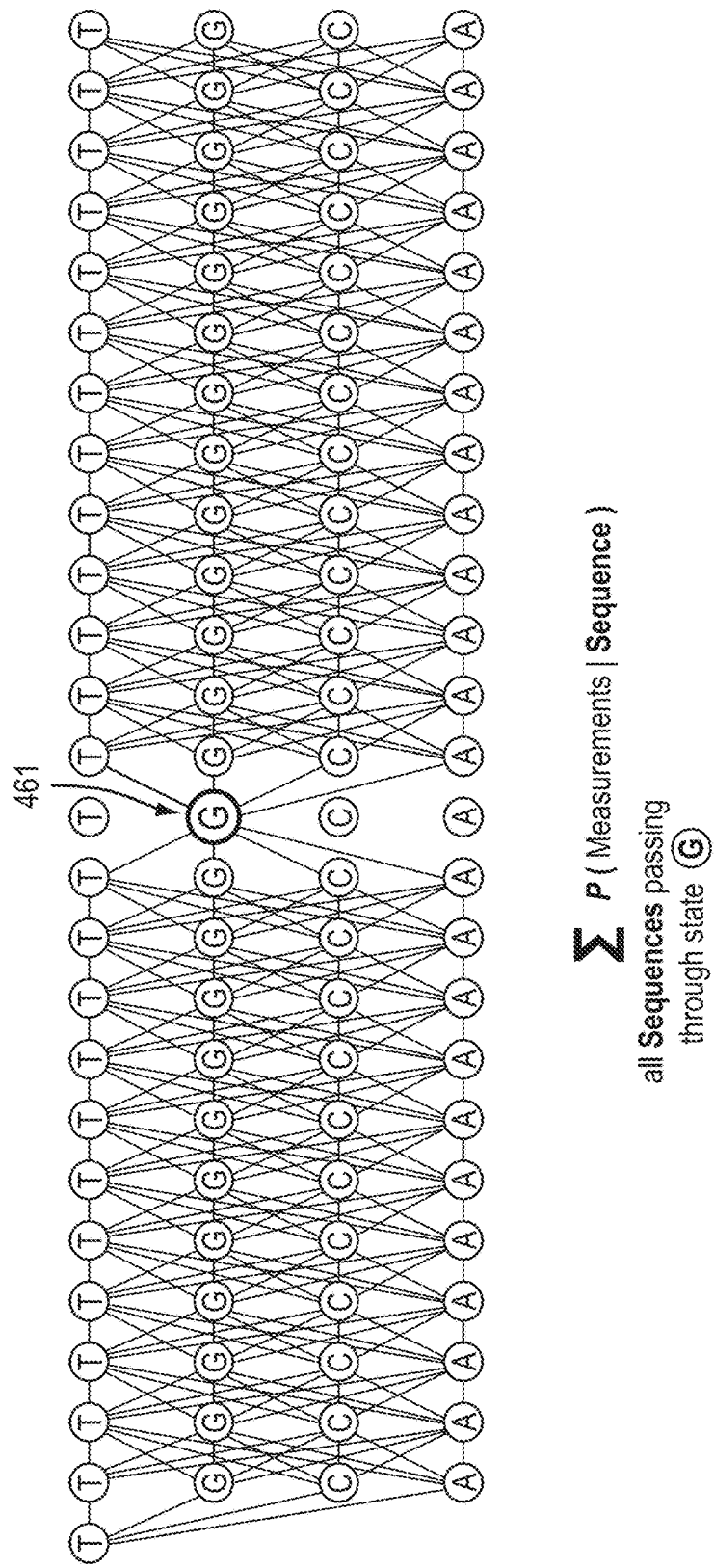
FIG. 32 is another representation of data processing by an embodiment of an algorithm of the system, and includes SEQ ID NO: 12.
Figure 33:
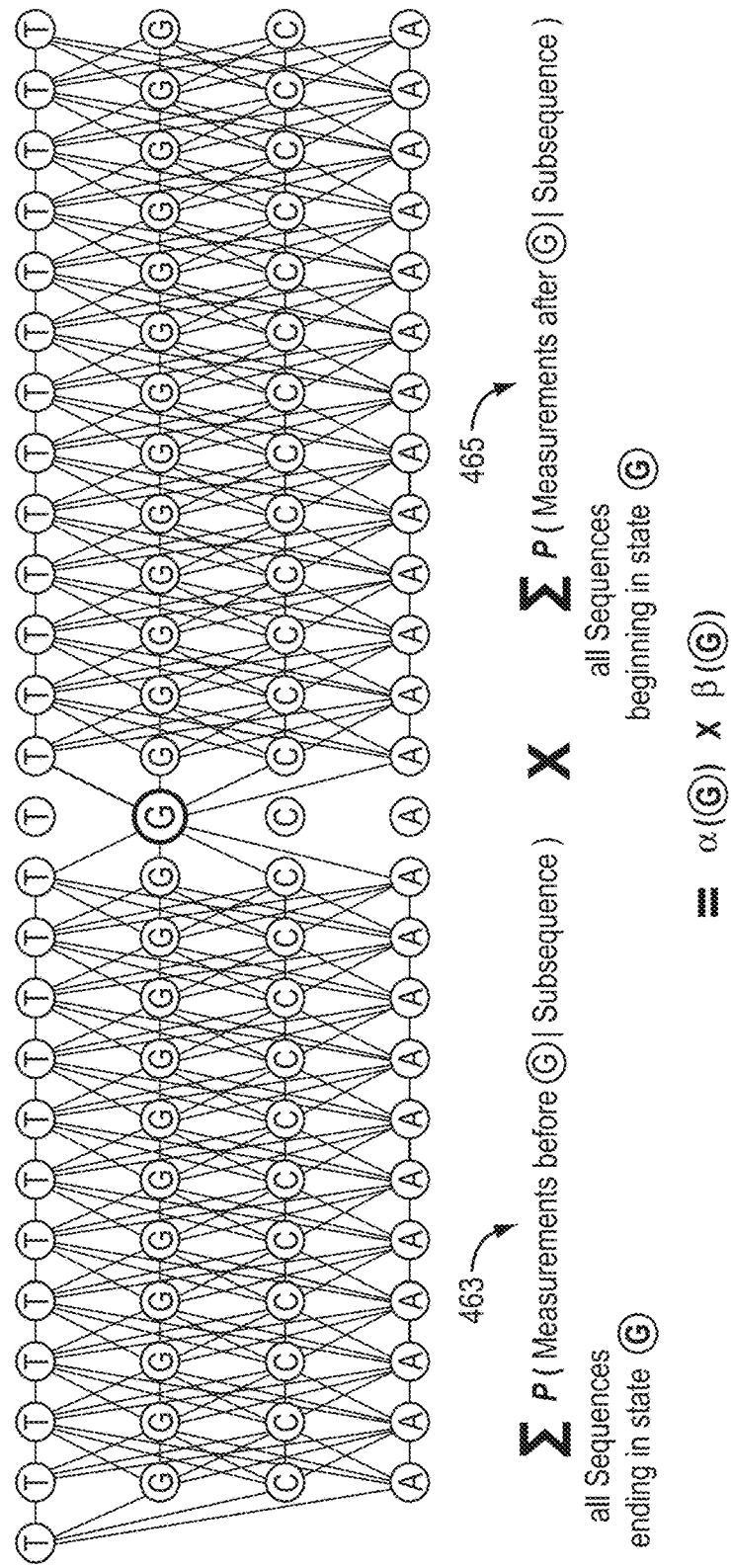
FIG. 33 is another representation of data processing by an embodiment of an algorithm of the system, and includes SEQ ID NO: 12.

FIGS. 32 and 33 depict additional benefits of the BCJR algorithm. Namely, the algorithm is configured such that initial measurements do not need to be repeated when evaluating later base probabilities. For example, as shown in FIG. 32, the algorithm can determine probabilities up to a certain intermediate position (or "state") in the grid and then start a "new" measurement from this position. For example, as shown, the algorithm can maximize probabilities up to intermediate position "G" 461. Then, as depicted in FIG. 33, position "G" 461 can then be designated as a starting point for a second set of calculations and the final result can be determined by summing those probabilities from the far left of the grid to the G position 461 (463) and the sum of those probabilities starting with the G position 461 and moving to the end of the graph (465). Thus, the BCJR algorithm does not have to start at nucleotide 1 every time the algorithm seeks to maximize the probability of a particular path which includes a later obtained color-likelihood.

Figure 34:
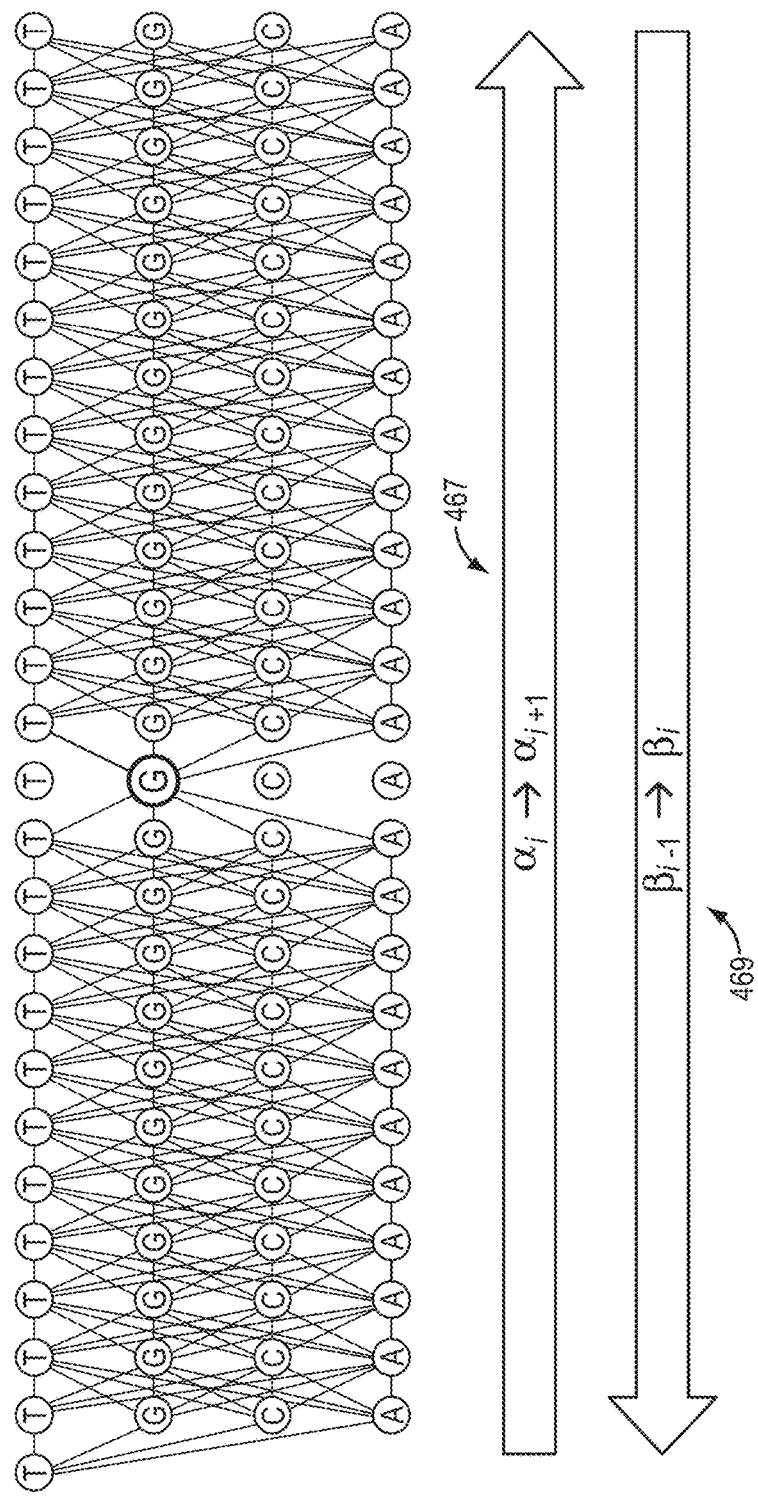
FIG. 34 is another representation of data processing by an embodiment of an algorithm of the system, and includes SEQ ID NO: 13 (traversing the figure from left to right) and SEQ ID NO: 14 (traversing the figure from right to left)

FIG. 34 depicts another advantage of the BCJR algorithm. As shown, in addition to (conceptually) starting from the far left of the grid and moving left to right, the algorithm can also be configured to start at the far right of the grid (e.g., the end of the sequence) and move right to left. In contrast to moving left to right, where the first base is typically known, moving right to left requires additional steps where each of A T C G must be considered to be the first base. The ability to evaluate the data from left to right and right to left further provides for efficient data analysis. Thus, any sum can be determined at any position by adding the sum determined from moving left to right 467 and the sum determined from moving right to left 469.

Figure 36A:
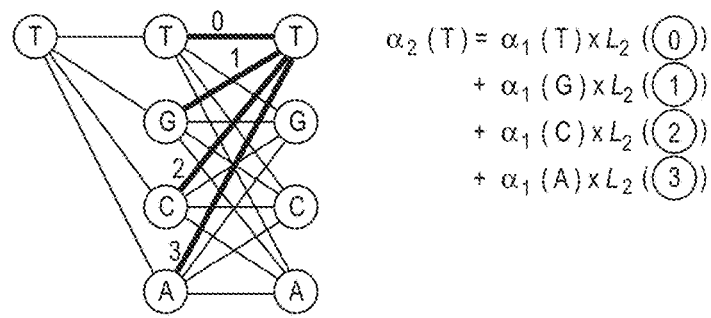
FIGS. 36A-36B are various representations of steps performed by an embodiment of an algorithm of the system.

FIGS. 35A-35E depicts some embodiments wherein the BCJR algorithm works from left to right across the grid in maximizing base call probabilities. That is, FIG. 35A shows that the first base is known because, in some DNA sequencing systems, the first base can represent the last base of the adaptor sequencing prior to the beginning of the unknown template. In this example, this base is taken to be T. FIGS. 35B-35E depicts the algorithm evaluating the probability that the identity of the second base is T (FIG. 35B), G (FIG. 35C), C (FIG. 35D), and A (FIG. 35E). However, in view of the redundancy introduced in the encoding scheme, the first color likelihood does not provide enough information to accurately identify the second base. Rather, the second base can only be identified after the algorithm has also maximized the various probabilities of second base based on the color-likelihoods of the signal generated between the $2^{nd}$ and $3^{rd}$ bases (as shown in FIG. 36A).

Figure 36B:
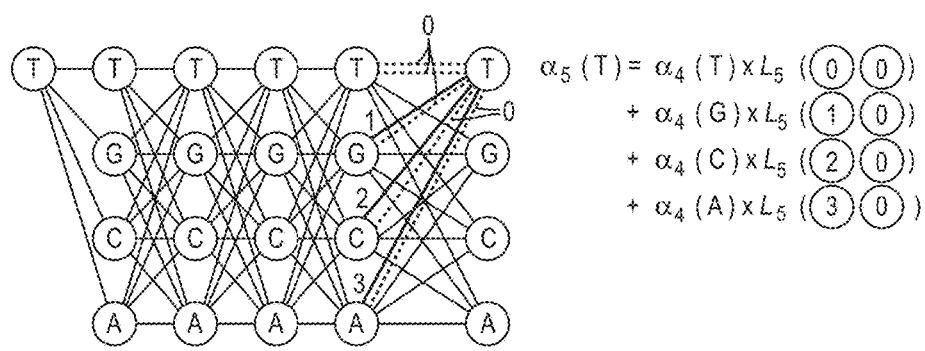

As such, the algorithm determines a base probability for $b_n$ based on color likelihoods between $b_{n-1}$ and $b_n$ and between $b_n$ and $b_{n+1}$. The multiple interrogations of a single base is provided by the redundancy introduced by multiple ligation rounds with offset primers. Additionally, as shown in FIG. 36B, another layer of redundancy is provided by the $6^{th}$ primer round with probes of a distinct probe set. As shown, the BJGR algorithm also maximizes each of the probe sets during these "double band" steps.

Figure 37A:
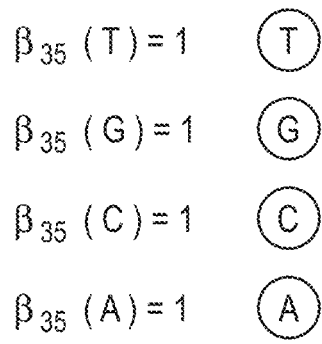
FIGS. 37A-37B are representations of steps performed by an embodiment of an algorithm of the system.
Figure 37B:
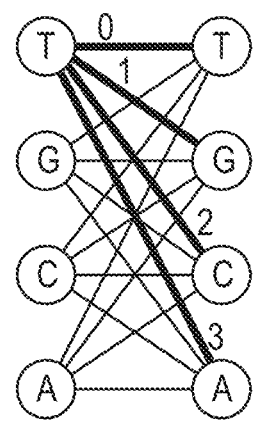

As indicated above, the BCJR algorithm can also evaluate data from the far right of the graph and move towards the beginning. FIGS. 37A and 37B provide representations of how these steps are initialized and carried out. For example, FIG. 37A shows that, as opposed to moving left to right where the first base is typically known, moving from right to left requires that the algorithm consider possibilities where any of A, T, C, or G could be the "most probable" final base. Next, as shown in FIG. 37B, all possible second (next to last) base positions are evaluated relative to all possible final base possibilities.

Figure 38A:
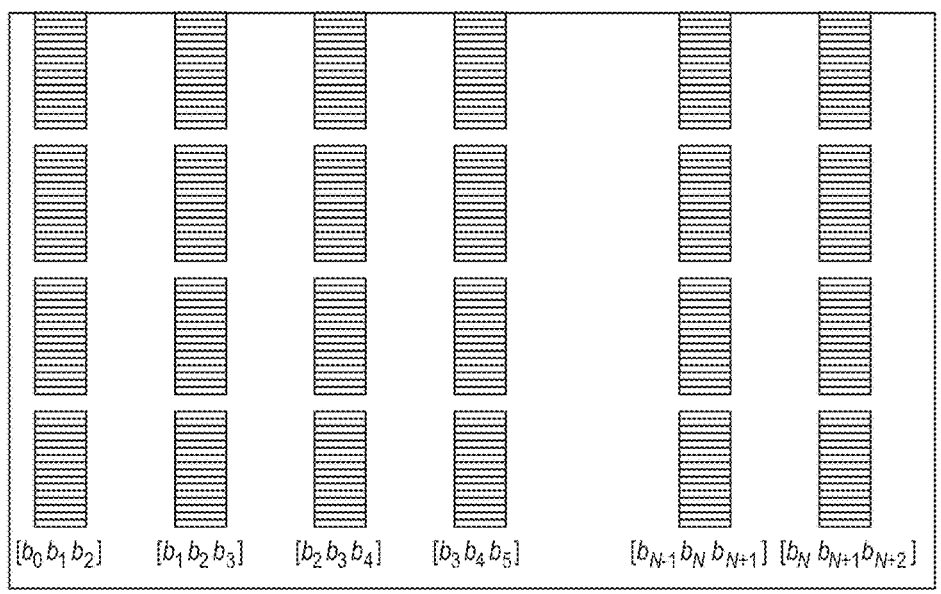
FIGS. 38A-38C are state graphs resulting from a sequencing process utilizing an embodiment of the presently disclosed 2+4 encoding scheme.
Figure 38B:
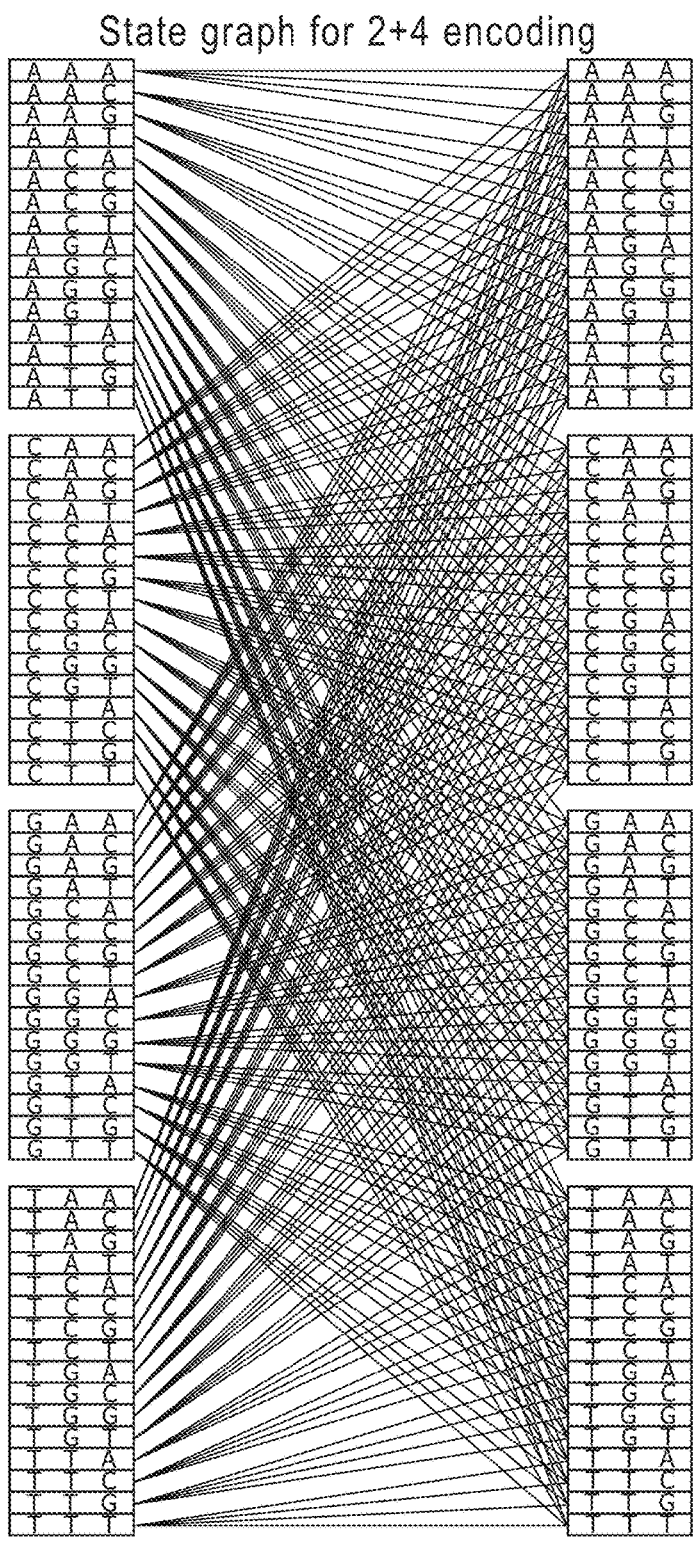
Figure 38C:
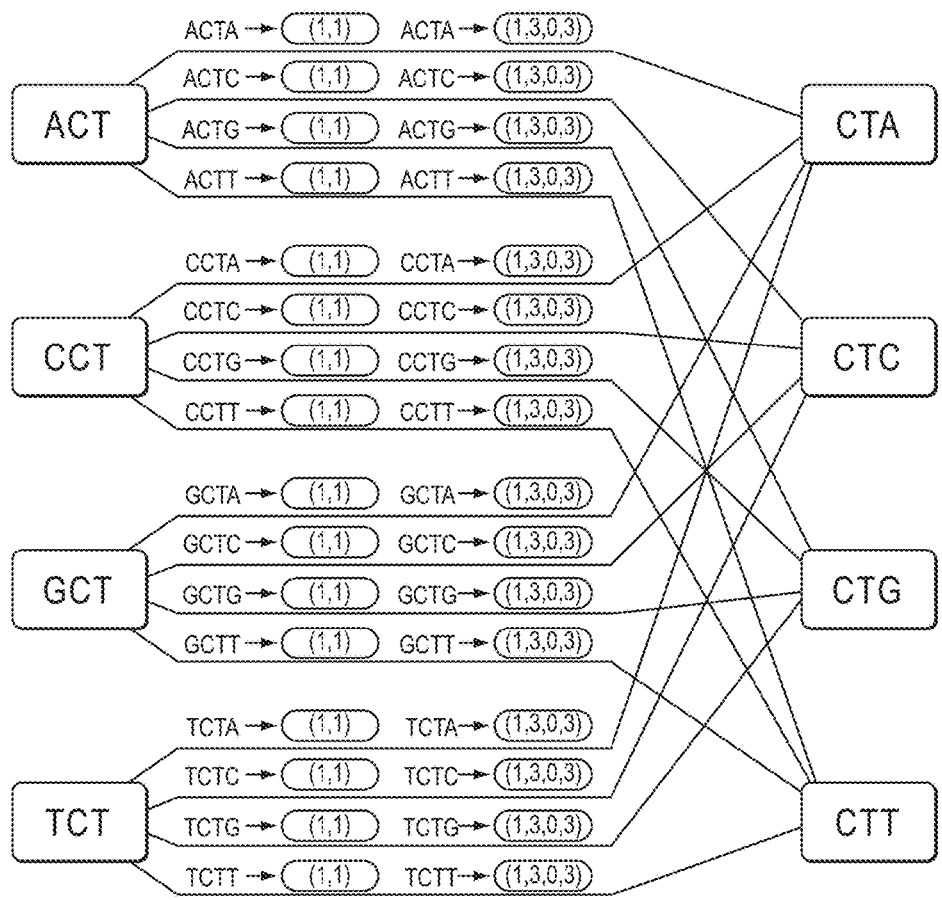

FIGS. 38A-38C provide additional representations of the system's decoder utilizing 2+4 encoding (i.e., 5 ligation rounds utilizing primer offsets and di-base codes from probe family 1 in addition to a 6th ligation round at a previously interrogate primer offset with probes of a second probe family). FIG. 38A provides a state graph wherein base b0 is the last base of the adaptor sequence. Bases b1-bn are unknown and must be determined from color measurements. As shown, the graph consists of N sections.

FIG. 38B provides one section N of the state graph of FIG. 38A. At the beginning and end of each section there are 64 states, corresponding to base triplets. Each starting state connects to 4 ending states with a branch. A branch corresponding to a quadruplet of bases $[b_i, b_{i+1}, b_{i+2}, b_{i+3}]$, when it connects state $[b_i, b_{i+1}, b_{i+2}]$ to state $[b_{i+1}, b_{i+2}, b_{i+3}]$.

FIG. 38C shows a subsection of one section of the state graph. As shown, a branch that corresponds to quadruplet of bases $[b_i, b_{i+1}, b_{i+2}, b_{i+3}]$, has an expected color in (1,1) probe set and an expected color in the (1,3,0,3) probe set. As detailed above, the expected colors are used to assign a metric to the branch, based on how well do measurements support that particular branch. Note, the measurements for the (1,3,0,3) probe set are only available in every fifth graph section.

Figure 39:
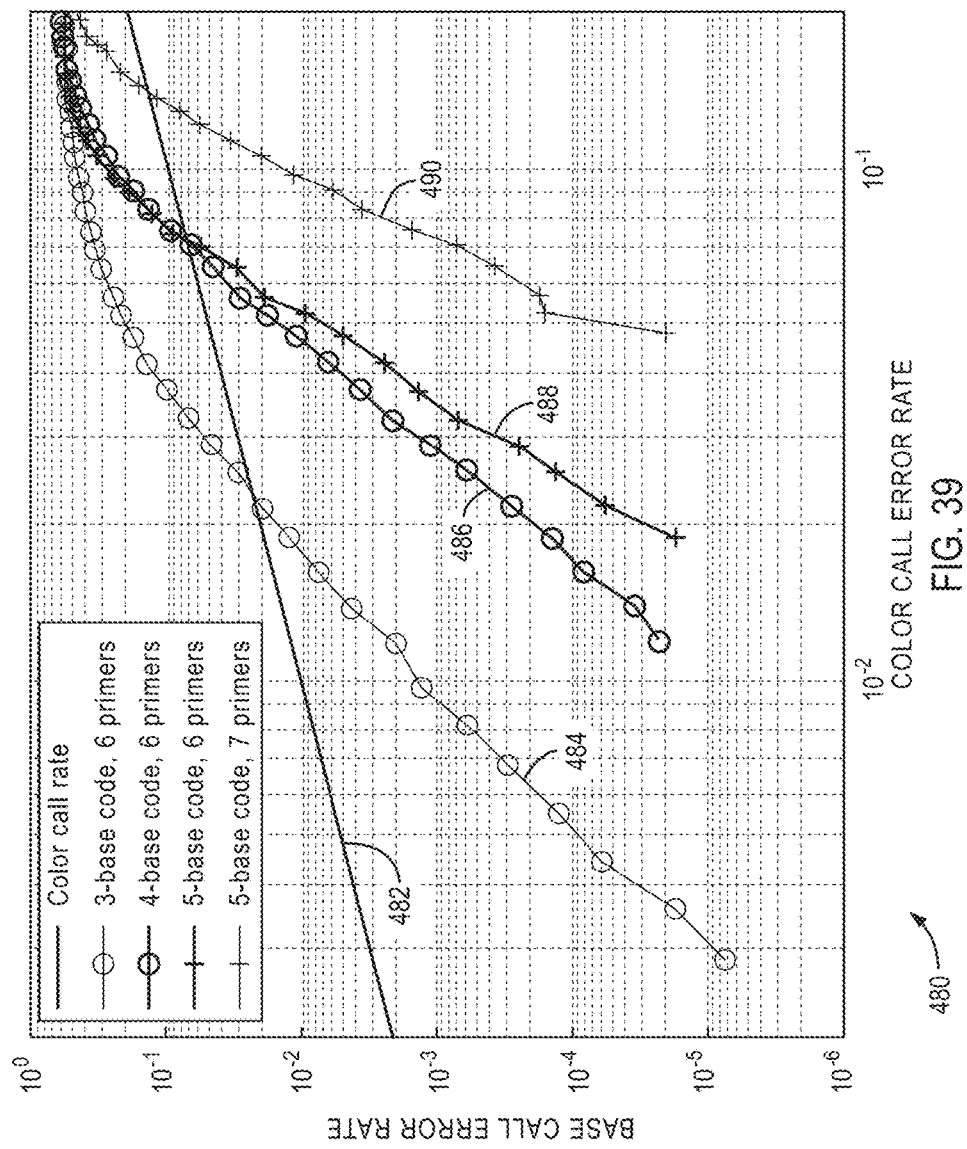
FIG. 39 is a graph which shows examples of the presently disclosed system performance that can be expected for variations of the example coding scheme of FIG. 28.

FIG. 39 shows error correction performance curves 480 for various K-base codes and primer rounds in ligation-based measurement system model. The curves 480 are plotted with base call error rate on the vertical axis and color call error rate on the horizontal axis. Data for such curves can be generated via the example feedback system described herein in reference to FIG. 22.

In FIG. 39, the four example curves represent error correction performances for the configurations listed in Table 1. More particularly, curve 488 represents the 5-base code and 6-primer-rounds configuration described in reference to FIG. 21. Curve 484 represents the 3-base code and 6-primer-rounds configuration; curve 486 represents the 4-base code and 6-primer-rounds configuration; and curve 490 represents the 5-base code and 7-primer-rounds configuration.

Also shown in FIG. 39 is a reference curve 482 where coding and decoding are not performed. For such a curve, a color call error translates directly into a base call error; and thus provides a good performance reference with respect to detection of color call errors and correcting such error to what the base call should be. As shown, the error corrected curves perform substantially better than the uncorrected curve 482 when the color call error rate is relatively low. When the color call error rate is relatively high, the corrected curves perform worse. It is believed that such an effect is likely due to a fact that coding (and in particular with large Hamming distance coding) for error correction has a tendency to spread out the likelihood of errors. With such spreading, correction of such errors can benefit significantly when the likelihood of error is relatively low. On the other hand, spreading out of relatively high error rates can result in the correction making the errors worse.

In certain embodiments, and as apparent in FIG. 39, coding for error correction can be implemented in situations where the expected color call rate is relatively low. Further, the value for K (number of symbols in the code) can be selected based on the expected color call rate. Also, in the context of the two 5-base codes 488 and 490, the 7-primer-round case (490) displays significantly better performance than the 6-primer-round case (488). As described herein, such performance enhancement can be weighed against other factors.

As described herein, encoding of data can be achieved via configuring of the probes in certain manners. Introduction of redundancy to the encoded data can be achieved via, for example, performing additional measurements. Because encoding and redundancy-introduction are integral parts of the probes and measurements, decoding and resulting error detection and correction steps do not necessarily require a reference sequence. Such decoding can be performed simply based on the encoding process.

Figure 40:
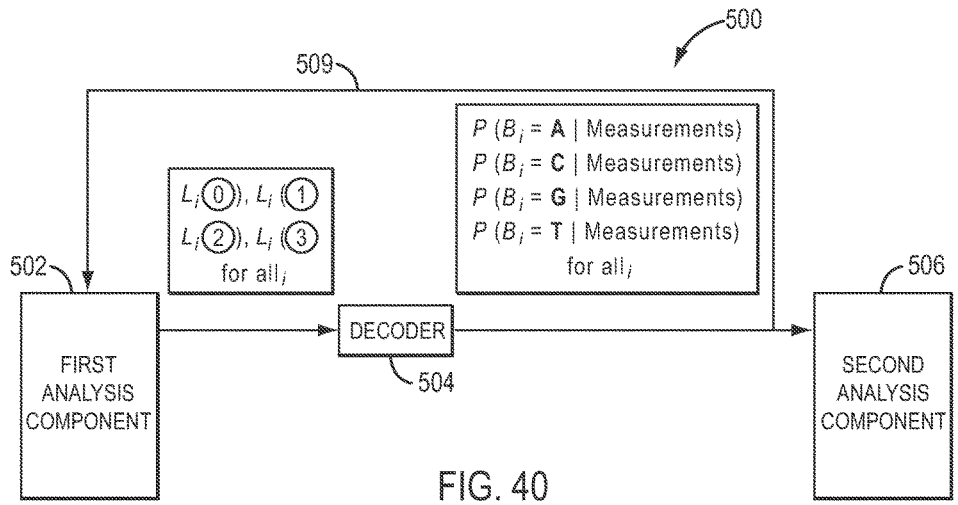
FIG. 40 is a block diagram of some embodiments where one or more features of the presently disclosed system can be incorporated into an existing sequencing system.

FIG. 40 shows another example of how such decoding step can be integrated into sequencing systems such as the SOLiD System. A decoding configuration 500 can include a decoder 504 that receives input data from a first analysis component 502. Such an input data can include color likelihoods of the detected dyes. The decoder 504 can decode the encoded sequence of color likelihoods and generate base probabilities, and such base probabilities can be provided to a second analysis component 506 for further analysis.

In certain embodiments, such base probabilities can also be provided back to the first analysis component (via arrow 509). If the probabilities are such that the decoder considers the result erroneous, the feedback 509 can allow correction of the color likelihood sequence by the first analysis component 502. Again, such determination of base probability error/ambiguity and any correction/resolution to the color likelihoods do not require reliance on any reference other than knowledge of the encoding scheme.

Figure 41:
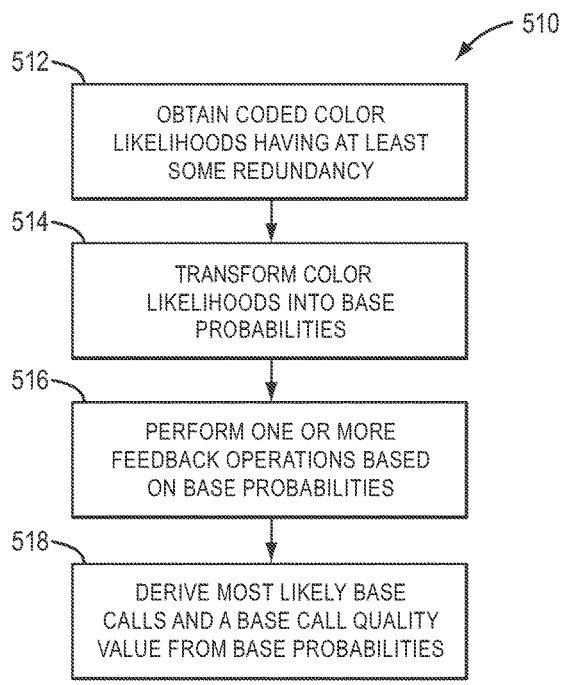
FIG. 41 is a flow-chart which shows a process that can be implemented to facilitate the example configuration of FIG. 40.

FIG. 41 shows a process 510 that can be implemented to provide the decoding feedback functionality as described in reference to FIG. 23. In a process block 512, coded sequence of color likelihoods can be obtained. As described herein, such coded sequence can include at least some redundant information. In a process block 514, the sequence of color likelihoods can be decoded. In a process block 516, the process can include performing one or more feedback operations based on base probabilities. In a process block 518, the process can include deriving most likely base calls and a base quality value from base probabilities.

The presently disclosed system and methods can include various other embodiments capable of contributing to improved polynucleotide sequencing accuracy. As described above, ultra-high throughput next generation sequencing (NGS) technologies, such as the SOLiD platform, provide the ability to sequence genomes quickly and cheaply. NGS systems typically read many more DNA fragments and produce shorter read lengths than traditional sequencing systems. Because it is generally considered impractical to generate de novo assembly from short reads if the error rate is greater than about one percent, NGS is mostly used for genome re-sequencing, e.g., finding SNPs and other differences in a human sample compared to the reference.

Short read NGS technologies coupled with error correction techniques can allow de novo assembly of previously unknown genomes. In one embodiment, one such error correction technique is based on an alignment of multiple reads without explicit pair-wise comparison. Repeating units of k nucleotides from portions of reads are used for fast hash-based alignment.

In the error correction technique, a set of reads, R, is corrected. If a particular k-mer appears at least m times in R, then the particular k-mer is included into a set of frequent k-mers called a spectrum. Error correction is performed by first examining all reads in the set R for k-mers that are close to being error-free k-mers. An error-free k-mer is defined as a k-mer having the exact sequence of nucleotides found in the particular k-mer from the spectrum. An error-free k-mer is also called a solid k-mer. An error-free or solid read is defined as a read that include only solid k-mers. Each read in the set R is examined to determine if by mutating a few nucleotides in the read an error-free k-mer can be formed from a k-mer that is close to being error-free. If a mutation is found that results in producing an error-free k-mer, the mutation is made and the read is error corrected. A mutation is made by substituting a nucleotide with one of three other possible nucleotides.

In certain embodiments, spectral alignment error correction (SAEC) is used to decrease the color call rate of an NGS system. Some NGS systems, such as the SOLiD™ platform, use two base encoding, as described above. Applying error correction to the color calling in a two base encoding system is more advantageous that applying error correction to a one base system. For example, a one color difference in a two base encoding system is almost always an error, while a one base difference in a one base system is often a duplication in the genome.

Figure 42:
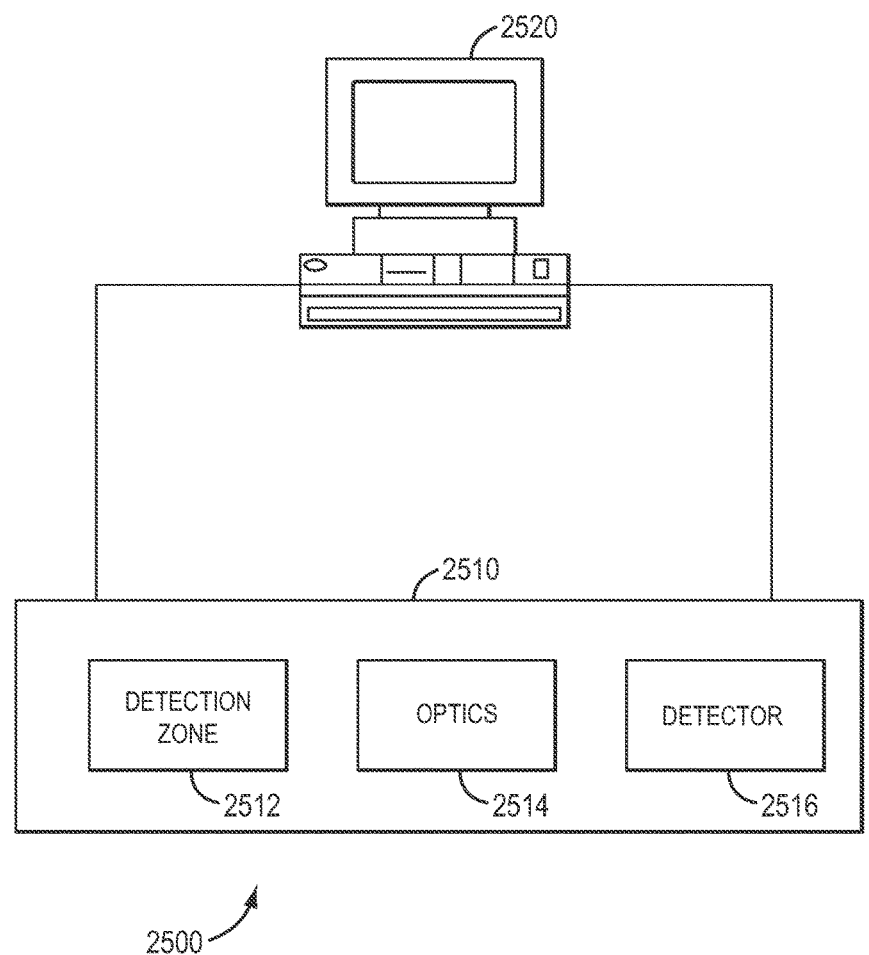
FIG. 42 is a schematic diagram of some embodiments of a system for error correcting DNA sample reads using spectral alignment error correction.

FIG. 42 is schematic diagram of a system 2500 for error correcting DNA sample reads using SAEC, in accordance with certain embodiments. System 2500 includes DNA sequencer 2510 and processor 2520. DNA sequencer 2510 can include, but is not limited to including, detection zone 2512, optics 2514, and detector 2516. DNA sequencer 2510 can be, but is not limited to, an NGS system such as the SOLiD™ platform. Processor 2520 can be, but is not limited to, a computer, microprocessor, or any device capable of sending and receiving control signals and data from DNA sequencer 2510 and processing data.

DNA sequencer 2510 and processor 2520 perform SEAC on color call DNA sample reads. In the context of certain fluorescence-based sequencing processes, a color call DNA sample read is a sequence fluorescence colors that represent the sequence of the DNA produced by DNA sequencer 2510. DNA sequencer 2510 analyzes a plurality of DNA samples and produces a plurality of reads from the plurality of DNA samples. Processor 2520 is in communication with the DNA sequencer 2510 and performs a number of steps.

Processor 2520 obtains the plurality of reads from the DNA sequencer. Processor 2520 then examines the plurality of reads for a sequence of consecutive color calls of length k that appear in the plurality of reads at least m times. As described above, if a particular sequence of consecutive color calls of length k, a k-mer, appears at least m times in the plurality of reads, the k-mer is said to belong to a spectrum. As a result, processor 2520 examines the plurality of reads for spectrum construction.

Finally, a spectrum is constructed, processor 2520 attempts error correction. In other words, if a spectrum is found, processor 2520 attempts error correction. Processor 2520 analyzes each read of the plurality of reads. For each read, processor 2520 examines each k-mer that does not belong to the spectrum and tries to mutate the color call in it. Color calls are examined based on their quality values. Processor 2520 starts with a color call with the lowest quality value and selects each succeeding or next color call corresponding to an increasing quality value, for example. Processor 2520 changes or corrects each color call it examines if the change produces a corrected sequence of length k that includes the changed color call and matches the sequence of consecutive color calls of length k in the spectrum. In other words, processor 2520 attempts to substitute color calls in k-mers of reads that almost match the k-mer of the spectrum, in order to maximize the number of k-mers that exactly match the k-mer of the spectrum.

In certain embodiments, the spectral parameters k and m are optimized using experimental data. For example, applying SAEC to bacterial genomes results in an optimal value of 17 for k. An optimal value for m is dependent on the coverage. For example, a coverage of 600 times results in an optimal value for m of 8, while a coverage of 300 times results in an optimal value for m of 5.

In certain embodiments, a probabilistic heuristic can be used to determine spectral parameters. For example, a probabilistic heuristic can be used to determine the optimal k-mer size. Also, a numerical analysis method can be used to find the most optimal division between a set of trustable and non-trustable k-mers in the spectrum. For example, for a given estimate of genome size, L, the number of correct k-mers cannot be larger than L. If both strands of DNA are considered, then the number of correct k-mers cannot be larger than 2*L. It is assumed that L is estimated with an accuracy of +/−20%, therefore, the top 2*L(1+/−0.2) high frequency k-mers are targeted for trustable values. If on the segment 2*L*0.8 to 2*L*1.2, for example, there is a k-mer frequency point, such that there is an exponential increase in the number of k-mers with lower frequency, then this point is an optimal division between sets of trustable and non-trustable k-mers.

In certain embodiments, DNA sequencer 2510 is a two base encoded DNA sequencer. As described above, SAEC is particularly advantageous for DNA sequencers that provide two base encoding, such as the SOLiD™ platform.

In certain embodiments, processor 2520 does not change the color call if an adjacent color call was previously changed. To prevent overcorrection and generation of chimeric reads, correction in two adjacent positions is avoided.

In certain embodiments, processor 2520 examines the plurality of reads for a sequence of consecutive color calls of length k that appear in the plurality of reads at least m times such that the sequence includes color calls having quality values above a threshold value. In other words, quality values are used to calculate the spectrum so that systematic errors, or errors that are frequent in the same position, do not go into the spectrum.

In certain embodiments, multiple rounds of error correction are used to decrease error rates. For example, processor 2520 examines the plurality of once corrected reads for a second sequence of consecutive color calls of length k that appear in the plurality of reads at least m times. If the second sequence of consecutive color calls of length k appears in the plurality of reads at least m times, processor 2520 attempts error correction. In other words, after a second spectrum is constructed, processor 2520 attempts error correction. Processor 2520 analyzes each read of the plurality of reads. For each read, processor 2520 examines each k-mer that does not belong to the spectrum and tries to mutate each color call in it. Color calls are examined based on their quality values. Processor 2520 starts with a color call with the lowest quality value and selects each succeeding next color call according to an increasing quality value, for example. Processor 2520 changes or corrects each color call it examines if the change produces a second corrected sequence of length k that includes the changed color call and matches the second sequence of consecutive color calls of length k used to define the second spectrum.

In certain embodiments, color calls are examined based on their number of spectral votes in addition to their quality values. A color call receives a spectral vote if a mutation in that color call makes a seed belong to the spectrum. A seed is a portion of a spectrum, for example. When spectral votes are used, processor 2520 starts with a color call with the lowest quality value and most spectral votes and selects each succeeding next color call according to an increasing quality value and decreasing spectral vote count.

In certain embodiments, processor 2520 combines spectral votes with the probability of error associated with quality values and corrects most likely errors, thus avoiding overcorrection. For example, for a certain mutation with v votes in the read position and with quality value q, an adjusted number of votes is equal to $v*(1+10*P_{error}(q))$. $P_{error}$ is the probability of error in a position with quality value q.

Figure 43:
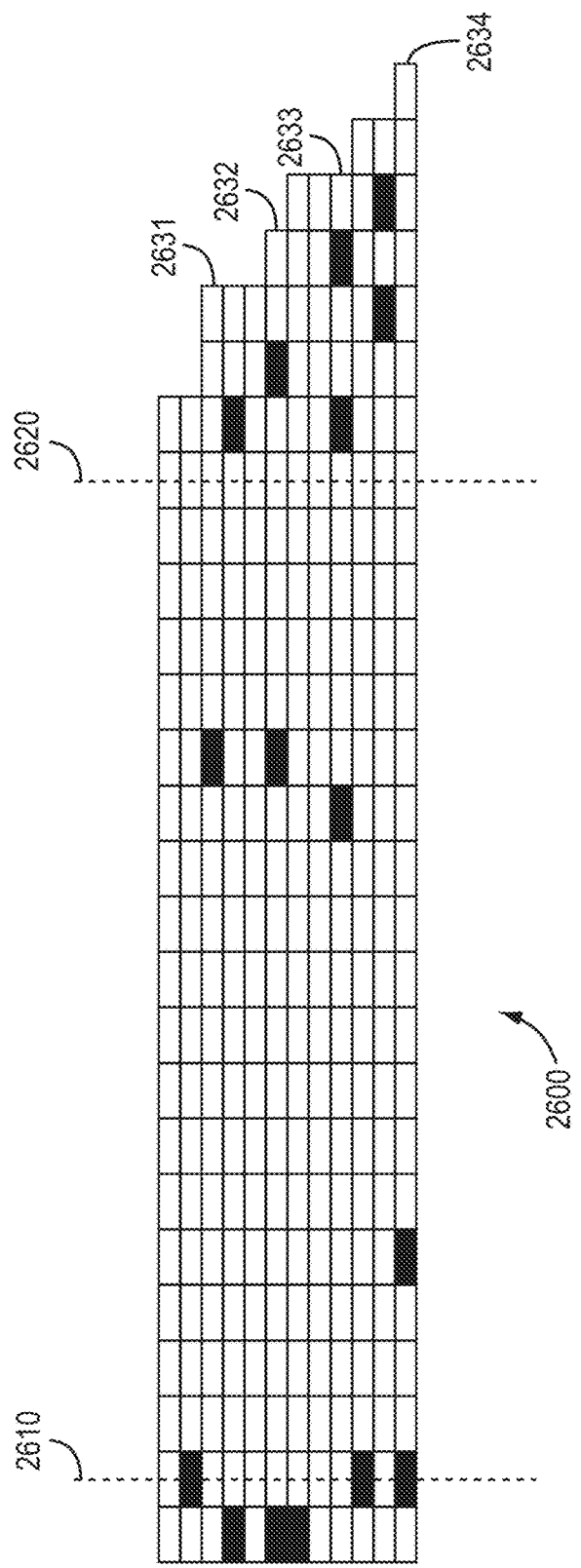
FIG. 43 is a representation of an exemplary portion of an alignment of DNA color call reads, in accordance with some embodiments.

FIG. 43 is an exemplary portion of an alignment 2600 of DNA color call reads, in accordance with certain embodiments. Alignment 2600 includes twelve color call reads. Between dashed line 2610 and dashed line 2620 a sequence of consecutive color calls of length 17 appears in the twelve reads 8 times. This sequence is shown in alignment 2600 as a sequence of 17 consecutive white color calls. The twelve reads that include this 17-mer sequence belong to a 17-mer spectrum. The remaining four reads in alignment 2600, read 2631, read 2632, read 2633, and read 2634, each include one black color call between dashed line 2610 and dashed line 2620. In certain embodiments, SAEC is used to change the one black color call in read 2631, read 2632, read 2633, and read 2634 to a white color call.

Figure 44:
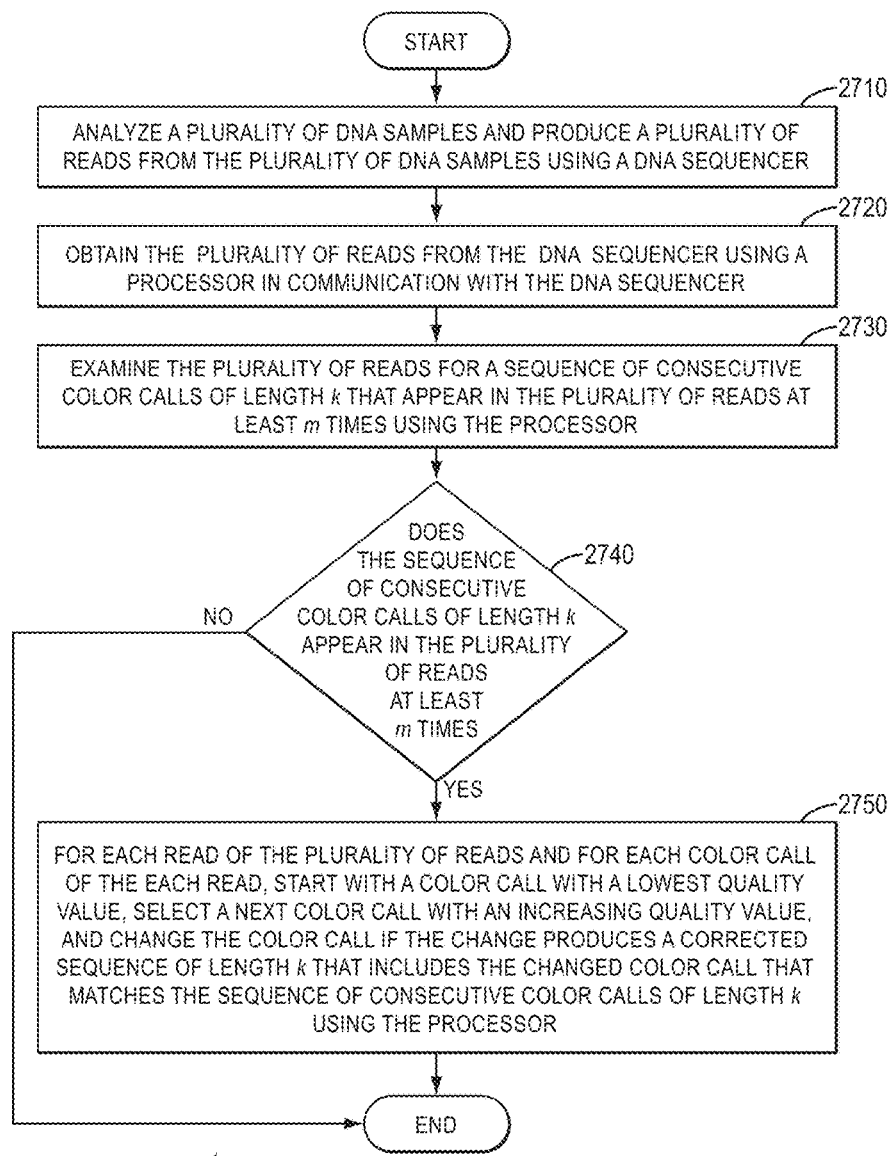
FIG. 44 is a flow-chart showing a method for error correcting DNA sample reads using spectral alignment error correction, in accordance with certain embodiments.

FIG. 44 is a flowchart showing a method 2700 for error correcting DNA sample reads using SAEC, in accordance with certain embodiments.

In step 2710 of method 2700, a plurality of DNA samples is analyzed and a plurality of reads from the plurality of DNA samples is produced using a DNA sequencer.

In step 2720, the plurality of reads from the DNA sequence is obtained using a processor in communication with the DNA sequencer.

In step 2730, the plurality of reads is examined for a sequence of consecutive color calls of length k that appear in the plurality of reads at least m times using the processor.

In step 2740, it is determined if the sequence of consecutive color calls of length k appears in the plurality of reads at least m times.

In step 2750, if the sequence of consecutive color calls of length k appears in the plurality of reads at least m times, for each read of the plurality of reads and for each color call of the each read, a color call with a lowest quality value is selected as the starting color call, a next color call is selected that has a corresponding increasing quality value, and each color call that is selected is changed if the change produces a corrected sequence of length k that includes the changed color call and matches the sequence of consecutive color calls of length k using the processor.

In certain embodiments, a computer program product includes a tangible computer-readable storage medium whose contents include a program with instructions being executed on a processor so as to perform a method for error correcting DNA sample reads using SAEC. This method is performed by a system of distinct software modules.

Figure 45:
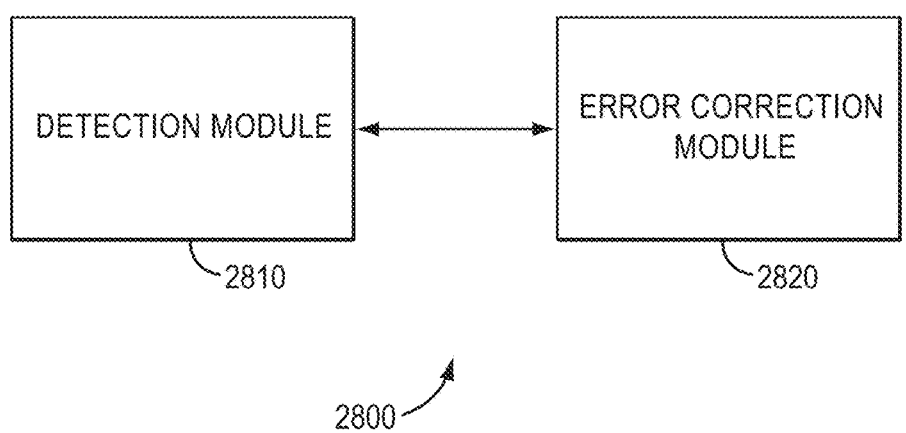
FIG. 45 is a schematic diagram of a system of distinct software modules that performs a method for error correcting DNA sample reads using spectral alignment error correction, in accordance with certain embodiments.

FIG. 45 is a schematic diagram of a system 2800 of distinct software modules that performs a method for error correcting DNA sample reads using SAEC, in accordance with certain embodiments. System 2800 includes detection module 2810 and error correction module 2820. Detection module 2810 and error correction module 2820 perform a number of steps.

Detection module 2810 obtains a plurality of reads from a DNA sequencer that analyzes a plurality of DNA samples and produces the plurality of reads from the plurality of DNA samples.

Error correction module 2820 examines the plurality of reads for a sequence of consecutive color calls of length k that appear in the plurality of reads at least m times.

If the sequence of consecutive color calls of length k appears in the plurality of reads at least m times, for each read of the plurality of reads and for each color call of the each read, error correction module 2820 starts with a color call with a lowest quality value, selects a next color call with an increasing quality value, and changes each color call, if the change produces a corrected sequence of length k that includes the changed color call and matches the sequence of consecutive color calls of length k.

In some embodiments, a system for error correcting polynucleotide (e.g., DNA) sample reads using spectral alignment error correction is provided. The system can include a sequencer (e.g., a two-base encoded sequencer) that analyzes a plurality of polynucleotide samples and produces a plurality of reads from the plurality of DNA samples. The system can also include a processor in communication with the DNA sequencer that can obtain the plurality of reads from the DNA sequencer, examine the plurality of reads for a sequence of consecutive color calls (or likelihoods) of length k (e.g., 17) that appear in the plurality of reads at least m times, and if the sequence of consecutive color calls of length k appears in the plurality of reads at least m times, can perform further analysis. For example, for each read of the plurality of reads and for each color likelihood of the each read the processor can start with a color likelihood with a lowest quality value, select a next color likelihood with an increasing quality value, and change each color likelihood if the change produces a corrected sequence of length k comprising each color call that matches the sequence of consecutive color calls of length k.

In some embodiments, the processor can start with a color call having a highest number of spectral votes in addition to a lowest quality value and select a next color call with a decreasing number of spectral votes in addition to an increasing quality value. In some embodiments, the processor does not change each color call if an adjacent color call was previously changed. In some embodiments, the sequence of consecutive color calls of length k can includes color calls having quality values above a threshold value.

In some embodiments, the processor can be configured to examine the plurality of reads for a second sequence of consecutive color calls of length k that appear in the plurality of reads at least m times. Further, if the second sequence of consecutive color calls of length k appears in the plurality of reads at least m times, for each read of the plurality of reads and for each color call of the each read the processor starts with a color call with a lowest quality value. The processor can also select a next color call with an increasing quality value, and change each color call if the change produces a second corrected sequence of length k comprising each color call that matches the second sequence of consecutive color calls of length k.

Various methods for error correcting polynucleotide sample reads using spectral alignment error correction are also provided herein. The method can include, for example, analyzing a plurality of polynucleotide (e.g., DNA) samples and producing a plurality of reads from the plurality of samples using a sequencer. The method can also include obtaining the plurality of reads from the DNA sequencer using a processor in communication with the DNA sequencer and examining the plurality of reads for a sequence of consecutive color calls of length k that appear in the plurality of reads at least m times using the processor. In some embodiments, if the sequence of consecutive color calls of length k appears in the plurality of reads at least m times, for each read of the plurality of reads and for each color call of the each read starting with a color call with a lowest quality value, the method includes selecting a next color call with an increasing quality value, and changing each color call if the change produces a corrected sequence of length k comprising each color call that matches the sequence of consecutive color calls of length k using the processor.

Various embodiments of a computer program product are also disclosed herein. For example, the computer program product can include a tangible computer-readable storage medium whose contents include a program with instructions being executed on a processor so as to perform a method for error correcting DNA sample reads using spectral alignment error correction. Various embodiments of such a method are disclosed herein. For example, the method can include providing a system having distinct software modules, and wherein the distinct software modules comprise a detection module and an error correction module. The method can also include obtaining a plurality of reads from a sequencer that analyzes a plurality of polynucleotide (e.g., DNA) samples and produces the plurality of reads from the plurality of DNA samples using a detection module. The method can also include examining the plurality of reads for a sequence of consecutive color calls of length k that appear in the plurality of reads at least m times using the error correction module. In some embodiments, if the sequence of consecutive color calls of length k appears in the plurality of reads at least m times, for each read of the plurality of reads and for each color call of the each read starting with a color call with a lowest quality value, the method can include selecting a next color call with an increasing quality value, and changing each color call if the change produces a corrected sequence of length k having each color call that matches the sequence of consecutive color calls of length k using the error correction module.

Although the above-disclosed embodiments have shown, described, and pointed out the fundamental novel features of the invention as applied to the above-disclosed embodiments, it should be understood that various omissions, substitutions, and changes in the form of the detail of the devices, systems, and/or methods shown may be made by those skilled in the art without departing from the scope of the invention. Consequently, the scope of the invention should not be limited to the foregoing description, but should be defined by the appended claims.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

What is claimed is:

1. A method for configuring a detectable probe for sequencing a polynucleotide, comprising:

arranging, using a processor, a number K of bases, each base being one of nucleotides A, C, G, and T;

determining a number X of rounds of interrogation, a number N of different types of detectable labels in a set of detectable labels, a number S of offsets of the detectable probe relative to the polynucleotide, and a number of M measurable characteristics, wherein a combination of X, N, S and M meet a redundancy condition;

assigning one or more detectable labels of the set of detectable labels to said arrangement of bases to form a labeled arrangement of bases, wherein said labeled arrangement of bases provides a configuration for the detectable probe; and using the detectable probe during a sequencing operation performed on the polynucleotide to generate a set of measurements corresponding to the combination of X, N, S and M.

2. The method of claim 1, wherein the assigning step assigns one detectable label to said arrangement of bases.

3. The method of claim 1, wherein the set of detectable labels comprises four or more different dyes.

4. The method of claim 2, wherein said one detectable label comprises one of four different dyes.

5. The method of claim 4, wherein said assigning of said label to said arrangement of bases further comprises:

transforming said arrangement of bases to a numerical representation based on a map associating the bases A, C, G, and T with numerical values;

multiplying the numerical representation and a generator vector based on a Galois field GF(4) multiplication table to form members of a product sequence;

adding the members of the product sequence based on a Galois field GF(4) addition table to form a sum; and mapping the sum to one of said four dyes based on a color assignment map to select the dye for said arrangement of bases to form the labeled arrangement of bases.

6. The method of claim 5, wherein said generator vector comprises one of a number of unique codes.

7. The method of claim 5, wherein said arrangement of bases comprises 3 bases, and said generator vector comprises one of 256 unique 3-base codes.

8. The method of claim 5, wherein said arrangement of bases comprises 4 bases, and said generator vector comprises one of 4096 unique 4-base codes.

9. The method of claim 5, wherein said arrangement of bases comprises 5 bases, and said generator vector comprises one of 65536 unique 5-base codes.

10. The method of claim 5, further comprising selecting the generator vector based at least in part on a relatively large Hamming distance among codes generated by the generator vector.

11. The method of claim 5, further comprising:

multiplying the numerical representation and a second generator vector based on the Galois field GF(4) multiplication table to form members of a second product sequence;

adding the members of the second product sequence based on the Galois field GF(4) addition table to form a second sum; and mapping the second sum to one of said four dyes based on the color assignment map to select the dye for said arrangement of bases to form a second labeled arrangement of bases, wherein the second labeled arrangement of bases provides a configuration for a second detectable probe.

12. The method of claim 1, wherein the redundancy condition is met when $N^M > 4^K$ and M is equal to $K*(X/S)$.

13. The method of claim 11, further comprising using the second detectable probe in at least one round in the number X of rounds of interrogation.

* * * * *